(12) United States Patent
Ritchey et al.

(10) Patent No.: US 11,716,444 B2
(45) Date of Patent: Aug. 1, 2023

(54) HUMAN-LIKE EMULATION ENTERPRISE SYSTEM AND METHOD

(71) Applicants: Kurtis John Ritchey, Leavenworth, KS (US); Kenneth Ira Ritchey, Leavenworth, KS (US)

(72) Inventors: Kurtis John Ritchey, Leavenworth, KS (US); Kenneth Ira Ritchey, Leavenworth, KS (US)

( * ) Notice: Subject to any disclaimer, the term of this patent is extended or adjusted under 35 U.S.C. 154(b) by 0 days.

(21) Appl. No.: 17/069,542

(22) Filed: Oct. 13, 2020

(65) Prior Publication Data

US 2021/0105435 A1  Apr. 8, 2021

(51) Int. Cl.
*G06F 9/44* (2018.01)
*H04N 7/14* (2006.01)
(Continued)

(52) U.S. Cl.
CPC ......... *H04N 7/142* (2013.01); *G02B 27/0093* (2013.01); *G02B 27/0172* (2013.01);
(Continued)

(58) Field of Classification Search
CPC ............... H04N 7/142; H04N 5/23238; H04N 21/4305; H04N 5/23218; H04N 5/2251; H04N 5/2254; H04N 7/15; H04N 5/2259; H04N 2007/145; H04N 5/2256; H04N 7/147; H04N 7/157; H04N 5/225; G10L 15/26; G02B 27/0093; G02B 27/0172; G02B 27/0176; G02B 27/0179; G02B 2027/0178; G02B 27/017; G02B 2027/0123; G02B 2027/0156; G02B 2027/0138; G02B 2027/014; G02B 2027/0187; G06F 3/013; G06F 3/015; G06F 3/012; G06F 1/163; G06N 10/00; G06N 3/084; G06N 3/0635; G06N 3/0454; G06N 3/049; G06N 3/088; G06Q 10/06; G06Q 10/067; G09G 3/003; A61B 5/6803; A61B 5/686; A61B 5/369; A61B 5/4064; A61B 5/0022; A61B 5/0024; A61B 5/0059; A61B 5/0064; A61B 5/0077; A61B 5/1114; A61B 5/245; A61B 5/745; A61B 6/501; A61B 2560/0242; A61B 5/7264; A61B 5/7246;
(Continued)

(56) References Cited

U.S. PATENT DOCUMENTS 11,055,356 B2 * 7/2021 Ritchey ................ G02B 27/017
11,538,587 B2 * 12/2022 Bill ........................ G16H 20/60
(Continued)

*Primary Examiner* — Howard D Brown, Jr.

(57) ABSTRACT

An enterprise system and method for maintaining and transitioning humans to a human-like self-reliant entity is presented. Said system including at least one a biological, biomechatronic, and mechatronic entity with a biological or artificial neural network to at least one transform or maintain. Embodiments are provided to assist in the transition of human between a biological state to a bio-mechatronic and mechatronic entity. Said entity's biological, biomechatronic, and mechatronic subsystems are configured to communicate and interact with one another in order for said enterprise system to manage, configure, maintain, and sustain said entity throughout the entity's life-cycle. Subsystem embodiments and components supported by the enterprise system are presented.

20 Claims, 20 Drawing Sheets

(51) Int. Cl.

| | | |
|---|---|---|
| *H04N 21/43* | (2011.01) | |
| *G10L 15/26* | (2006.01) | |
| *G02B 27/00* | (2006.01) | |
| *G02B 27/01* | (2006.01) | |
| *G06F 3/01* | (2006.01) | |
| *H04N 7/15* | (2006.01) | |
| *H04N 23/50* | (2023.01) | |
| *H04N 23/55* | (2023.01) | |
| *H04N 23/58* | (2023.01) | |
| *H04N 23/61* | (2023.01) | |
| *H04N 23/698* | (2023.01) | |

(52) U.S. Cl.
CPC ..... *G02B 27/0176* (2013.01); *G02B 27/0179* (2013.01); *G06F 3/013* (2013.01); *G06F 3/015* (2013.01); *G10L 15/26* (2013.01); *H04N 7/15* (2013.01); *H04N 21/4305* (2013.01); *H04N 23/50* (2023.01); *H04N 23/55* (2023.01); *H04N 23/58* (2023.01); *H04N 23/61* (2023.01); *H04N 23/698* (2023.01); *G02B 27/017* (2013.01); *G02B 2027/014* (2013.01); *G02B 2027/0123* (2013.01); *G02B 2027/0138* (2013.01); *G02B 2027/0156* (2013.01); *G02B 2027/0178* (2013.01); *G02B 2027/0187* (2013.01); *H04N 2007/145* (2013.01)

(58) Field of Classification Search
CPC .... G01R 33/4806; G01R 33/24; G03B 37/00; G16H 40/63
See application file for complete search history.

(56) References Cited

U.S. PATENT DOCUMENTS

| | | | |
|---|---|---|---|
| 2003/0233250 A1* | 12/2003 | Joffe | G16H 15/00 705/2 |
| 2005/0114829 A1* | 5/2005 | Robin | G06Q 10/06 717/101 |
| 2012/0113209 A1* | 5/2012 | Ritchey | G06F 3/015 348/14.02 |
| 2013/0063550 A1* | 3/2013 | Ritchey | G03H 1/2294 345/207 |
| 2020/0218767 A1* | 7/2020 | Ritchey | G09G 5/14 |
| 2021/0105435 A1* | 4/2021 | Ritchey | G06F 3/013 |

* cited by examiner

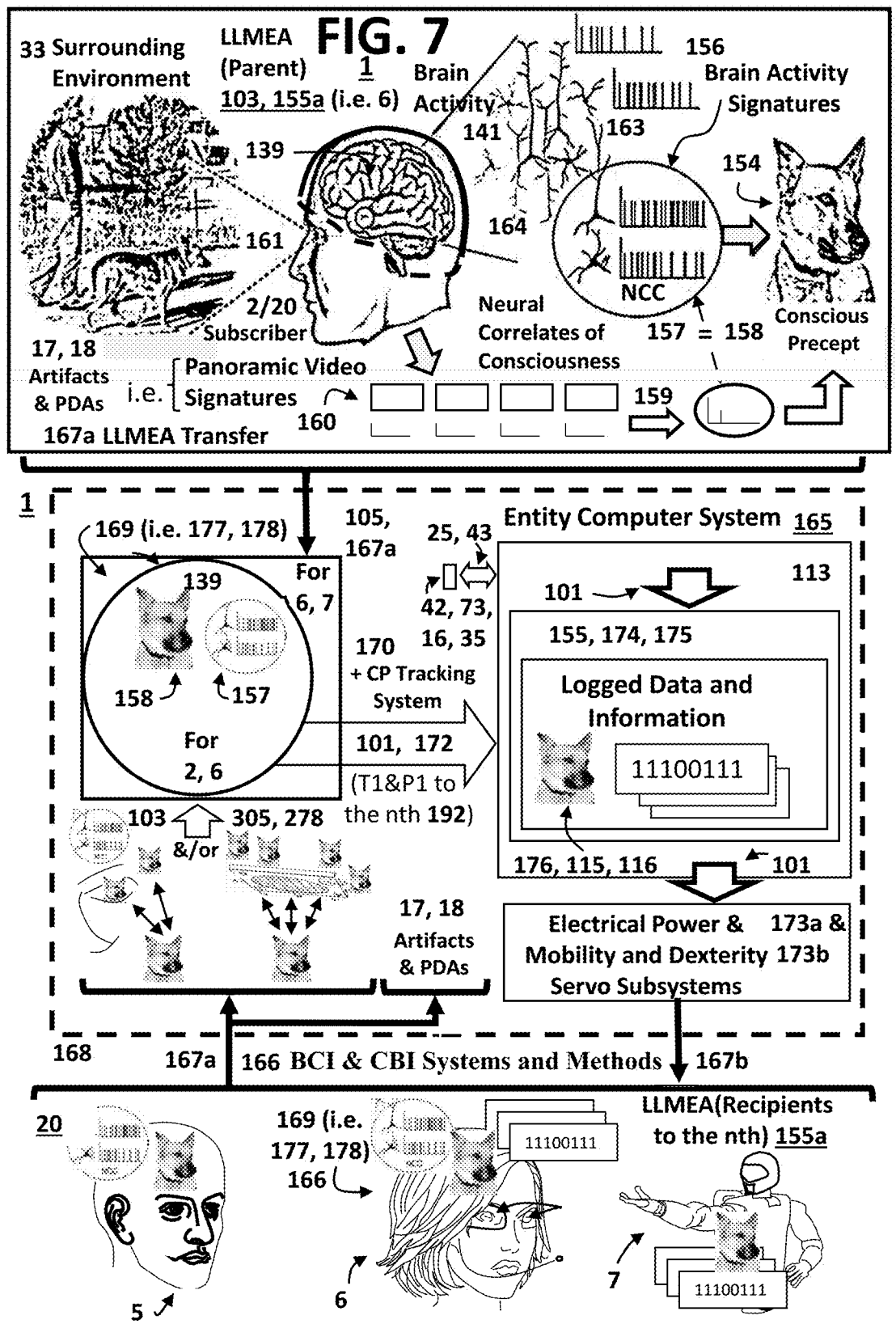

177, 236
6a, 97a 178, 236
6b, 97b 260, 264, 284, 273

ELECTRO-OPTIC IMAGE SENSING INWARD 249, 260
264

DISPLAY ILLUMINATING OUTWARD 249, 260
264

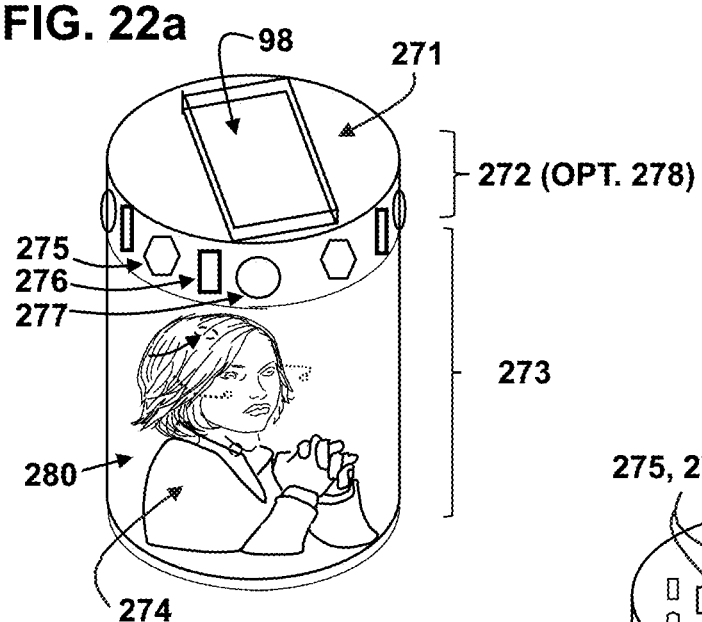
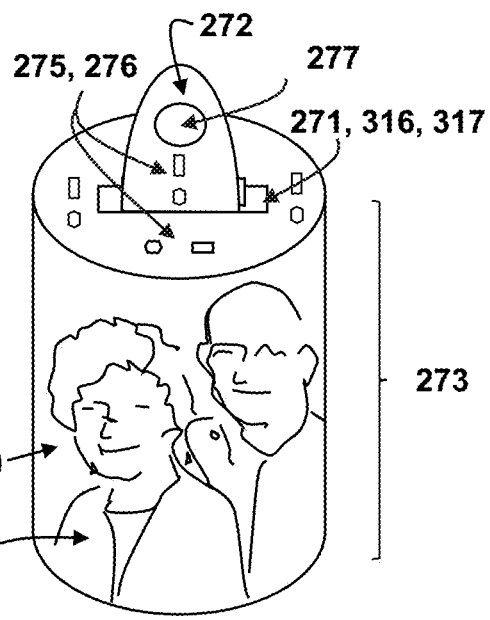
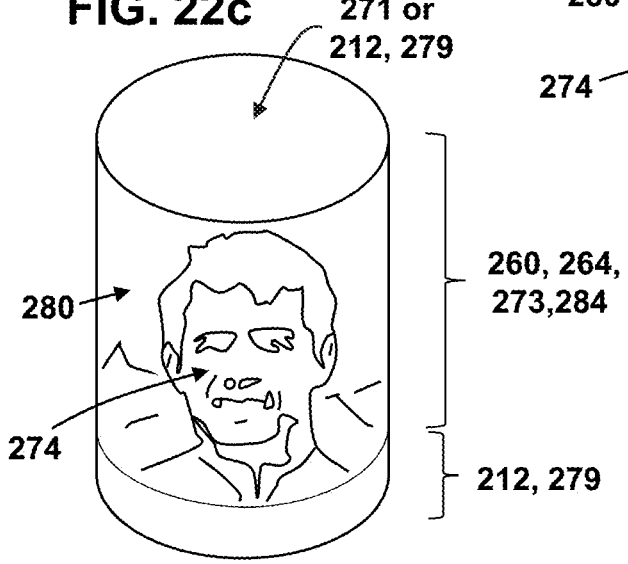

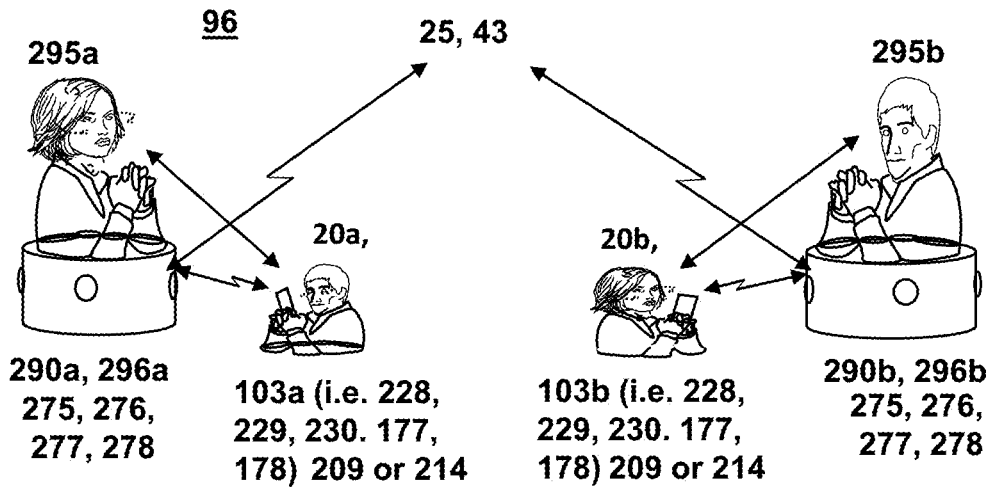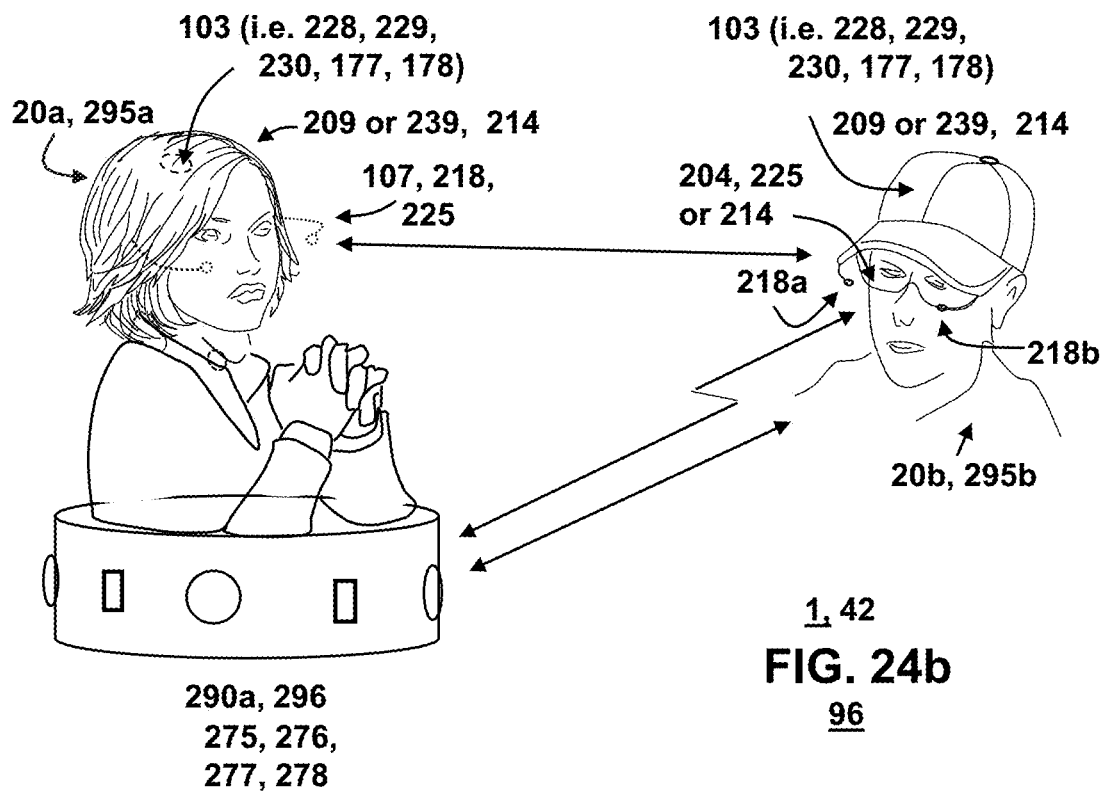

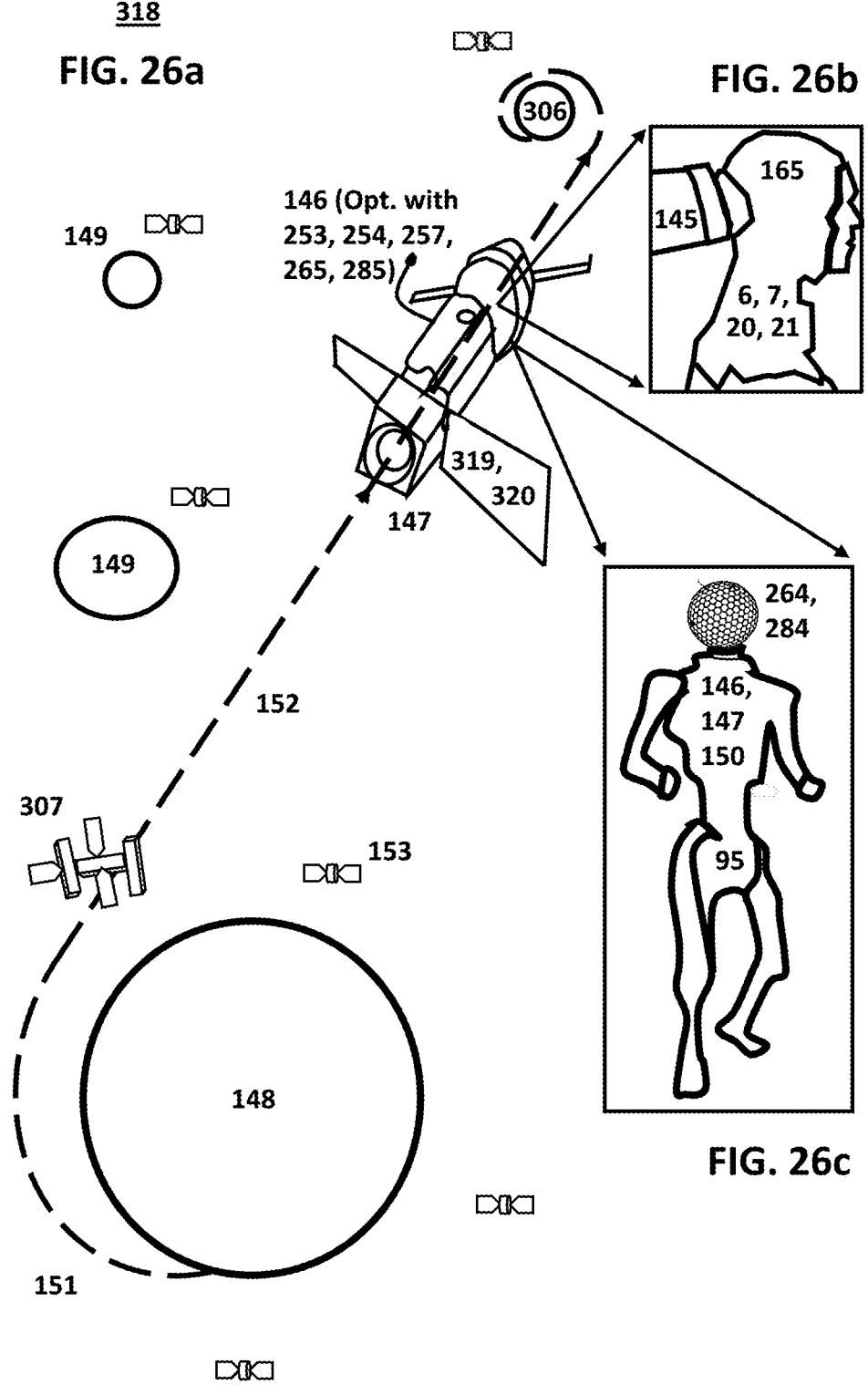

HUMAN-LIKE EMULATION ENTERPRISE SYSTEM AND METHOD

RELATED APPLICATIONS

This continuation-in-part application is related to and claims the benefit of application Ser. No. 11/354,779 filed on 15 Feb. 2006 entitled "Dynamic Interactive Region-Of-Interest Panoramic/Three-Dimensional Immersive Communication System and Method" (abandoned); application Ser. No. 11/830,637 filed on 30 Jul. 2007 entitled "Panoramic Image-Based Virtual Reality/Telepresence Audio-Visual System and Method" (abandoned); application Ser. No. 12/266,308 filed on Nov. 6, 2008 entitled "Panoramic Adapter System and Method with Spherical Field-Of-View Coverage" (abandoned); U.S. patent application Ser. No. 13/507,190 (granted as U.S. Pat. No. 9,101,279 B2) filed on 11 Jun. 2012 entitled "Mobile User Borne Brain Activity Data And Surrounding Environment Data Correlation System"; U.S. patent application Ser. No. 13/294,986 (granted as U.S. Pat. No. 9,344,612 B2) filed on 11 Nov. 2011 entitled "Non-Interference Field-Of-View Support Apparatus For A Panoramic Facial Sensor"; U.S. patent application Ser. No. 14/788,437 (granted as U.S. Pat. No. 9,451,899 B2) filed on 30 Jun. 2015 entitled "Mobile User Borne Brain Activity Data and Surrounding Environment Data Correlation System"; and U.S. patent application Ser. No. 15/152,214 filed on 11 May 2016 entitled "Non-interference Field-Of-View Support Apparatus For A Panoramic Sensor" (granted as U.S. Pat. No. 10,447,966 B2); U.S. patent application Ser. No. 15/258,336 filed on 7 Sep. 2016 entitled "Mobile User Born Brain Activity Data And Surrounding Environment Data Correlation System" (granted as U.S. Pat. No. 11,055,356 B2); Continuation-in-Part (CIP) U.S. patent application Ser. No. 16/601,010, filed on 14 Oct. 2019 entitled "Human-like Emulation Enterprise System and Method" (granted as U.S. Pat. No. 11,287,847 B2); U.S. Design patent application (Ser. No. 29/754,671) filed on 13 Oct. 2020 entitled "Virtual Video Assistant for a Surrounding Environment" (granted as U.S. D977,448 S); U.S. Design patent application (Ser. No. 29/861,253) filed on 28 Nov. 2022 entitled "Low Profile User Interface for a Surrounding Environment" (pending). The instant application is being examined and Applicants respectfully requests benefit under the first inventor to file (FTF) and first to invent (FTI) provisions of the AIA and pre-AIA 35. U.S.C 102 and 103 status of the above applications and patents filed after Mar. 16, 2013. The above applications and patents are hereby incorporated by reference in their entireties into the present application.

FIELD OF INVENTION

This invention relates to a human-like emulation enterprise system and method for building, maintaining, and transferring perceptions between a human biological and a related human-like bio-mechanical and mechanical system. For instance, recent improvements in enterprise architecture, business systems, artificial neural network mimicking systems, nano technology, metamaterials, 3d printing, 5G computing, quantum safe computing, and fusion reactor electrical power generation systems are incorporated into the present invention. Additionally, the fields of neurology, biology, biometric sensor engineering, prosthetic devices, implants, augmented cognition, whole brain emulation, computer science, artificial intelligence, machine learning, deep learning, statistical analysis, fast fusion computer processing, panoramic imaging, surround audio, sub-vocalization, computer simulation, geospatial information, telecommunications, Internet search engines and social media, robotics, body modification, body worn, surgically implanted, and body mounted devices are relevant to the present invention.

BACKGROUND OF THE INVENTION

A human-like emulation enterprise system and method for building, maintaining, and transferring perceptions between a human biological and related human-like bio-mechanical and mechanical systems that facilitate human-like life extension that mimics the human biological parent has not been designed. Instead, only components that could be used to form an enterprise have been developed. Additionally, a number of technologies that enable an enterprise have not been incorporated into an enterprise system and method for building, maintaining, and transferring perceptions between a human biological and related human-like bio-mechatronic and mechatronic systems that facilitates human-like life extension that mimics the human biological parent. For instance, recent improvements in enterprise architecture, brain activity sensing systems, artificial neural network mimicking systems, 3d printing, Nano technology, 5G computing, quantum safe computing, and fusion electrical power generation systems have not been incorporated into a human-like emulation enterprise.

SUMMARY OF THE INVENTION

A human-like emulation enterprise system and method that maintains and transitions humans to a supplementary adaptable sentient human-like self-reliant entity is claimed. Said system includes at least one a biological, bio-mechatronic, and mechatronic entity with at least one natural or artificial neural network to maintain. Embodiments of the instant invention claimed assist in the transition of humans between a biological, bio-mechatronic, and mechatronic entity and vice versa. Said entity biological, bio-mechatronic, and mechatronic subsystems are configured to communicate and interact with one another for said enterprise system to manage, configure, maintain, and sustain said entity throughout its collective life-cycle. Also claimed are embodiments with human-like general intelligence, super-intelligence, general physical, and super-physical capabilities. Enterprise system solutions claimed address system and design engineering, personal, cultural, societal, political, economic, geospatial, injustice, inequality, and environmental issues.

OBJECT OF THE INVENTION

It is therefore an objective of the present invention to develop a family of related personal assistant methods and systems that contribute to an Neural Correlates of Consciousness (NCC) relational database of information, knowledge, and artifacts that define and enable an entity's biological, bio-mechatronic, and mechatronic survival and operation in various environments needed to perform various tasks. In the present invention relational data base derived from brain activity sensing and processing can be considered an artifact or a collection of artifacts. The relational database derived and updated in a biological system, a biomechatronic system, a mechatronic entity or personal digital assistant can produce artifacts. For example, brain activity sensing system data of a subscriber, video footage of what subscriber is seeing, or processed data that comprises subscriber's relational database are artifacts. The personal complexities of a specific person may be replicated so that a biological, bio-mechatronic, or mechatronic entity may replicate that person. In one objective embodiment the recipient biological system can operate as a personal assistant. In another objective embodiment the user to continue as an emulation of the parent user after his or her natural biological death. An object of the present invention is to allow the reconstitution of a like injured, degraded, or destroyed biological, bio-mechatronic, or mechatronic system. And to provide a standard for human interaction and communication between a single or plural number of humans and machines that are biological, bio-mechatronic, or mechatronic systems.

Given the above it is also an objective of the present invention to provide a human-like entity that will overcome human limitations such as expensive heath care, criminality, resource requirements, environmental footprint, inherent physical constraints, and cognitive limitations. And finally, an objective is to consider the limitations the present invention with respect to privacy concerns, computer technology shortcomings, and consider human-like entities with artificial intelligence impact on humanity.

BRIEF DESCRIPTION OF DRAWINGS

FIG. 7 is a schematic diagram that illustrates systems and methods that data and information logged and derived from the internal physiological sensor systems, including the human neural system, and the external surround environment and peripheral sensing systems processed by the present invention that may be input into a recipient being, machine, or bio-mechanical system to facilitate enhancement, transcendence, replacement, or substitution of at least some portion of a recipient being, or bio-mechanical, mechanical system in accordance with the present invention.

FIG. 8a is a top side view of a MRI-based tractographic reconstruction of neural connections in the brain recorded by a Diffuse Tensor Imaging (DTI) to illustrate neural brain activity.

FIG. 8b is a greatly enlarged view of neurons firing and electro-chemical pathway currents activated in the brain by using calcium oscillation.

FIG. 9a provides a diagrammatic representation of the front view of a composite frame of undistorted panoramic imagery taken at Time 1 at a given location by the panoramic spherical field-of-view (FOV) surround video camera system of subject matter that corresponds to neural activity related to a conscious percept in the brain shown in FIG. 9b.

FIG. 9b is a diagrammatic representation of brain imagery representing subject matter that may be logged into the host computer system that correlates with panoramic imagery shown in FIGS. 9a and 8a-8b.

FIG. 9c is a diagrammatic representation of voxel brain imagery representing subject matter that may be logged into the host computer system that correlates with panoramic imagery shown in FIGS. 9a and 8a-8b.

FIG. 22a is a perspective view of a Personal Digital Assistant (PDA) with 360 FOV image capture and display coverage and 360 directional audio coverage and includes an inductive cellphone charging system on the top of the PDA.

FIG. 22b is a perspective view of an alternate arrangement for a PDA with 360 FOV image capture and display coverage and 360 directional audio coverage and includes an inductive charging.

FIG. 22c is a perspective view of another alternative arrangement for a PDA with 360 FOV image capture and display coverage and 360 directional audio coverage.

FIG. 24a is a perspective view of a 360-degree projection holographic PDA image capture and display system.

FIG. 24b is an enlarged perspective view of a 360-degree projection holographic capture and display system shown in FIG. 24a.

FIG. 26a is a diagram that illustrates the benefit of a human-like robot in space suited for the hostile environment of space supported by the Enterprise Architecture according to the present invention.

FIG. 26b illustrates the benefits of an artifact device, PDA 95-99 or human-like mechatronic 7 system that can survive in deep space in accordance with and supported by the Enterprise Architecture according to the present invention.

FIG. 26c is a Spaceship that the human-like robot plugs into for data and information, C3I, and electrical power.

DETAILED DESCRIPTION OF THE INVENTION

Figure 1:
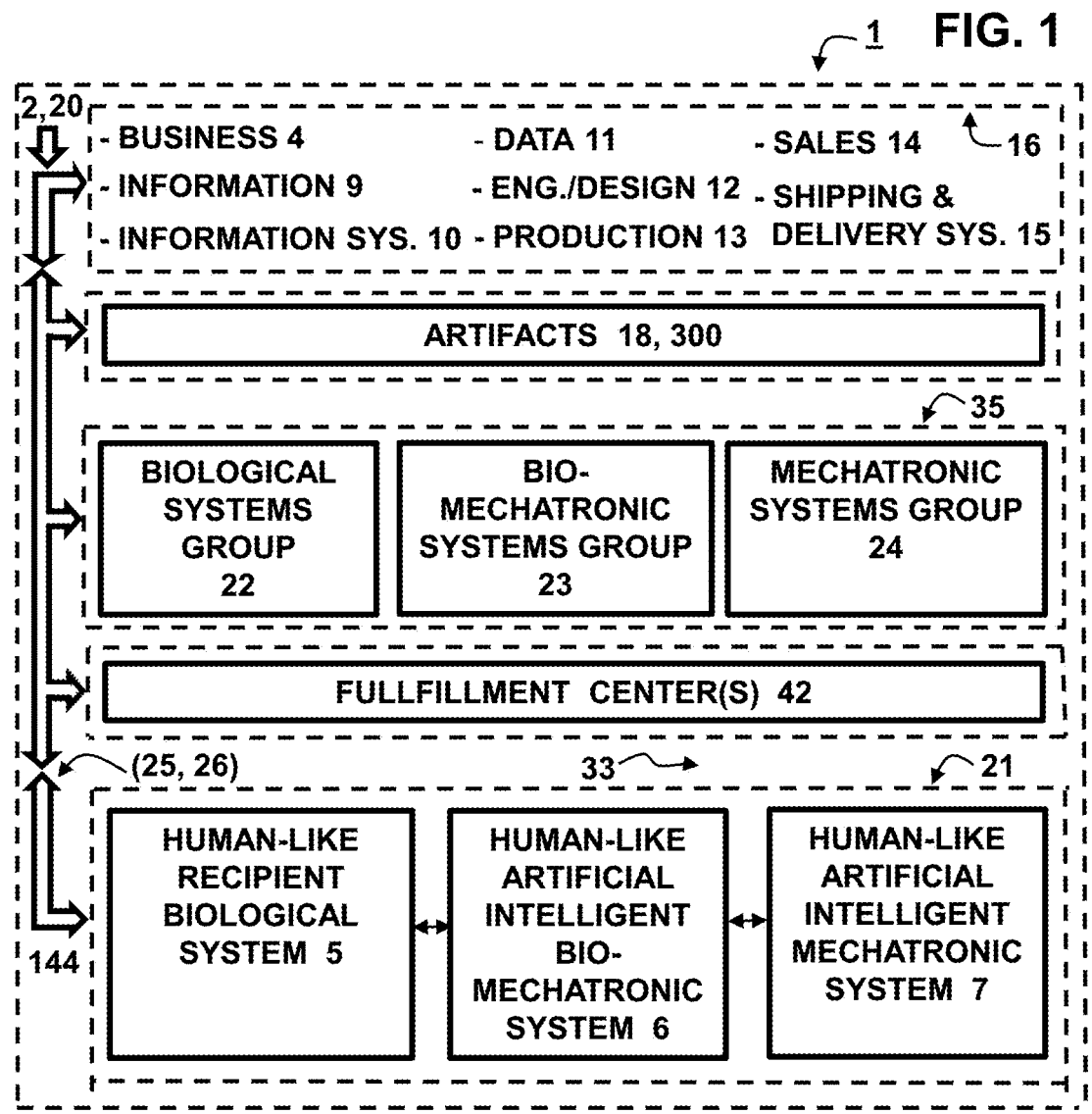
FIG. 1 is an Enterprise Architecture diagram of a human biological, bio-mechatronic, and mechatronic transformation system and method.

The following detailed description is provided to demonstrate the incorporation of the aforesaid Field Of Invention technologies into a design for an enterprise 1 system and method for constructing, maintaining and a transitioning a human 2 to and from a supplementary adaptable sentient human-like self-reliant entity 21. Hence, the first sections below discuss the enterprise system architecture, and then the second sections disclose devices, components, and methods comprising the parent human biological 2 being and related successor human-like biological 5, bio-mechatronic 6, and mechatronic 7 systems operated upon as part of the enterprise system to produce a family of compatible recurrent capable biological, bio-mechatronic, and mechatronic systems that emulate at least one specific person or derivation of a person.

Various embodiments of the present invention will now be described more fully with reference to the accompanying drawings, in which some, but not all embodiments of the invention are shown. Indeed, this invention may be embodied in many different forms and should not be construed as limited to the embodiments set forth herein. Rather, these embodiments are provided so that this disclosure will satisfy applicable legal requirements. When the words "may", "can", "might", "optional", "alternative", or the like are used, they mean that the associated feature or description is not a necessary, critical or required aspect of the broadest disclosed inventions, even though they may be desirable or preferred in certain instances. Also, please note that within the context of the specification the term "user", "subscriber," or the like is used to denote a user wearing or comprising a portable portion of the invention. And that a user or subscriber, or the like comprising the invention may be referred to interchangeably as a being, human-like entity, specimen, person, machine, mechanical, mechatronic, bio-mechanical bio-mechatronic, system, or recipient in various context of the present invention.

In the detailed description, reference is made to the accompanying drawings, which form a part hereof. In the drawings, similar symbols typically identify similar components, unless context dictates otherwise. In many instances in the drawings a group of numbers representing elements in the drawings are referenced to the specification. The reason that many numbers are referenced is to express that a single system represented by a single number includes related sub-components and sub-systems represented by the additional related numbers. For example, a biomechatronic entity 6 includes a human-like entity computer system 165 that comprises several key subsystems, modules, and components such as a brain activity sensing system 103 and artificial neural network system 196 that is responsive to host computer system 113 which includes a and mobility and dexterity system 254 an electrical power system 255, and entity support structure 256. Because of this the notation by a drawing of the biomechanical entity might be denoted as the group of numbers 6, 103, 113, 196, 254, 255, 256 with an arrow pointing from the group of numbers to the biomechanical entity shown in the drawing to express that these elements are included as part of entity 6. The illustrative embodiments described in the detailed description, drawings, and claims are not meant to be limiting. The term biomechanical and biomechatronic systems may be used interchangeably in the current application. Other embodiments may be utilized, and other changes may be made, without departing from the spirit or scope of the subject matter presented here. Those having skill in the art will recognize that the state of the art has progressed to the point where there is little distinction left between hardware, software, and/or firmware implementations of aspects of systems; the use of hardware, software, and/or firmware is generally a design choice representing cost versus efficiency tradeoffs. Those having skill in the art will appreciate that there are various logging and memory enhancement embodiments of the present invention by which processes and/or systems and/or other technologies described herein can be implemented (e.g., hardware, software, and/or firmware), and that the preferred vehicle will vary with the context in which the processes and/or systems and/or other technologies are incorporated. Those skilled in the art will recognize that optical aspects of implementations may employ business practices and automated business processes, cryptographic security systems, optically oriented hardware, software, and or a firmware solution to manipulate an image within the invention (i.e., removal of image distortion). Hence, many different types of wide angle and panoramic camera systems, sensor packages, brain activity sensor and physiological sensing systems, wireless communication devices, correlation systems, storage systems, force feedback, robotics, 3d printer systems, and graphic user interfaces may be incorporated without departing from the scope of the invention. There are several possible embodiments of the logging and memory enhancement system of the present invention by which the processes and/or devices and/or other technologies described herein may be effected, none of which is inherently superior to the other in that any logging and memory enhancement system to be utilized is a choice dependent upon the context in which the logging and memory enhancement system will be deployed and the specific concerns (e.g. portability, flexibility, or predictability) of the implementer, any of which may vary. Additionally, it will be apparent to those skilled in the art that various components and arrangements may be exercised in part or in whole to some extent without departing from the spirit of the invention.

In some implementations described herein, logic and similar implementations may include software or other control structures suitable to operation. Electronic circuitry, for example, may manifest one or more paths of electrical current constructed and arranged to implement various logic functions as described herein. Electronics within the invention may be in the form of an integrated circuit (IC), large scale integrated circuit (LSIC), very large-scale integrated circuit (VLSIC), printed circuit board (PCB), or motherboard. Components of the logging and memory enhancement system may communicate directly (i.e., over wire or fiber optics) or via wireless technologies (i.e., radio frequency, using WIFI and Bluetooth technology) known in the art, and may be supported outside or inside the human body, machine, or a combination thereof. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively, or additionally, in some variants, an implementation may include special-purpose hardware, software, firmware components, and/or general-purpose components executing or otherwise invoking special purpose components. For instance, in the present invention personal electronic devices (PEDs), like smartphones, are a derivation of a host computer, and are referred to interchangeably depending on the context of the discussion. Specifications or other implementations may be transmitted by one or more instances of tangible transmission media as described herein, optionally by packet transmission or otherwise by passing through distributed media at various times. Alternatively, or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode (s) of expression, such as algorithms). Alternatively, or additionally, some or all of the logical expression may be manifested as a Verilog-type hardware description or other circuitry model before physical implementation in hardware, especially for basic operations or timing-critical applications. It will also be understood by those skilled in the art that the use of the term "brain activity sensing system" refers to any mobile device worn by or implanted by a user. And that any imaging or data system or device that identifies neural activity in the brain of the user that provides imagery or data of the spatial location and time of neural activity in the brain for the purposes of generating Conscious Perceptions or Neural Correlates of Consciousness (NCC) refers to all possible types of devices that achieve and provide that result (i.e., to include fMRI, ultrasound, fNIR, red light, IMR, EEG, holographic, AMR, electrophysiology, and other like types and subsets of brain activity sensing systems 103, 169). Those skilled in the art will also realize that developing a relational database derived from correlating neural activity with conscious perceptions may be referred to in various terms but is equivalent to the current invention if executed similarly, whether or not it is called a NCC database. Also, those skilled in the art will recognize how to obtain, configure, and optimize suitable transmission or computational elements, material supplies, actuators, or other common structures in light of these teachings. In a general sense, those skilled in the art will recognize that the various embodiments described herein can be implemented, individually and/or collectively, by various types of electromechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electromechanical system" includes, but is not limited to, electrical circuitry operably coupled with a transducer (e.g., an actuator, a motor, a piezoelectric crystal, a Micro Electro Mechanical System (MEMS), synaptic, memristor, and neuromorphic computing and chips, etc.), electrical circuitry having at least one discrete electrical circuit, electrical circuitry having at least one integrated circuit, electrical circuitry having at least one application specific integrated circuit, electrical circuitry forming a general purpose computing device configured by a computer program. In the embodiments host, being, user, person, recipient, subject, system, or machine may be used interchangeably and refers to a thing or object on or into which the portable interactive data logging and memory enhancement system is situated or connected.

While line drawings are predominantly shown in the present invention to illustrate its workings and design, it should be noted that images of hardware, software, and firmware in the real world and the actual components comprising system 165 may be substituted with compatible systems and components without changing the scope of the invention. For instance, horizontal sectional line drawings representing latitudinal cross sections of the human brain are shown that graphically represent an fMRI, fNRI, AMR, EEG, ultrasound, holographic imaging, scan, regions, neurons, activity and connections in the brain. And for instance, it will be understood by those skilled in the art that related subject matter external and internal to the body that represents a given subject may be illustrated in the drawings as line as photos, line drawings, or numbers representing the same subject to help describe the invention. It will be understood well known to those skilled in the art that two-dimensional images (i.e., spectrum image, voxel-based brain image, brain network image, etc.) or three-dimensional perspective images (i.e., spectrum image, voxel-based brain image, brain network image, etc.) may be substituted to represent the same subject as a line drawing without deviating from the spirit of the invention. And line drawings representing subjects such as people and things can be replaced with images and photos of the actual subject without changing the disclosure of the present invention and without changing the scope and spirit of the invention.

Furthermore, all graphic representations used as examples herein are purely coincidental, fictitious, and any resemblance to actual people or places is unintentional and incidental and solely meant to illustrate the workings of the present invention. And any prior art, names of individuals, companies, logos, trademarks referenced in the present invention are meant to be used solely for a teaching tool and are solely owned by their agent and not claimed in any way by the present inventor, as they are being used solely for educational and demonstrational purposes.

In the present application the "Detailed Description" and corresponding "Drawings" are divided into three interrelated sections to facilitate understanding and for organizational purposes. Sheets 1-3 and 9 that correspond to FIGS. 1, 2, 3, and 19 show a system for managing and enabling embodiments of devices supported by the Human Emulation Enterprise System. Sheets 4-9 that correspond to FIGS. 4-10b illustrate the wide-ranging technical methods and systems of logging/collecting user data that facilitates the emulation of the user in a PDA device or and human-like bio-mechatronic and mechatronic entity within the context of the Business Architecture 4 of the Human Emulation Enterprise System. While Sheets 10-18, and 20 correspond to FIGS. 11-24b and FIGS. 26a-26c respectively to illustrate specific devices and system embodiments for logging/collecting user data that facilitates the emulation of the user in a PDA device and human-like bio-mechatronic and mechatronic entity within the context and scale of the Business Architecture that enables the Human Emulation Enterprise System. Significant improvements to related art cited and adopted in full in the present art are incorporated by reference in their entireties into the present application. The differences and improvements to the related art disclosed in the present application constitutes some patently new subject matter. Additionally, the enterprise method described in the present invention provides a novel transformative method that brings into play a separate class (i.e., 705, 707, or 717) and subclass that constitutes new subject matter that enables a level of human transformation heretofore not disclosed.

As depicted in FIG. 1, the first step in building an enterprise is to establish a business architecture 4. In accordance with the present invention the business architecture in a human-like emulation enterprise 1 is built around providing customers with hardware, software, and firmware that collect, build, maintain, and transfer perceptions between a biological system 2/5, bio-mechanical system 6, and mechanical system 7. To build this the enterprise into an enduring capability devices and components that sense the user and recipient biological, bio-mechanical, and mechanical system are constructed and the data derived from those devices and components are managed and operated upon using the enterprise system. The devices and components that sense the user may be alternatively constructed to be mobile and non-mobile, wired or wireless. Arrows, prentices, and lines indicate the dependencies and flow of the basic elements that comprise the enterprise architecture diagram shown in the FIG. 1.

Still referring to FIG. 1, the business architecture 4 of the enterprise 1 oversees and includes a business architecture 4, information architecture 9, information systems architecture 10, data architecture 11, engineering/design architecture 12, production architecture 13, sales and marketing architecture 14, and shipping and delivery systems architecture 15. The enterprise 1 architecture's 16 are tailored to deriving, transforming, and maintaining a shared relational computer database 37 that is adaptable to support a parent human biological 2, a successor human-like biological system 5, a bio-mechatronic 6 system, and a mechatronic 7 system subscriber 20 that operates by using at least one natural or artificial neural network to survive within at least one surrounding environments 33. To this objective, the system orchestrates the enterprise over 5G telecommunications systems and networks 25 and over shipping and delivery systems 26 to interact with a human being 2, recipient 5, subscribers 20, and venders 29, to manage hardware 38, software 39, and firmware 40 research, development, and manufacturing. Work groups 35 that include a biological systems group 22, a bio-mechatronics systems group 23, and a mechatronic systems group 24 within the enterprise 1 are managed by the business architecture 4. The business architecture 4 of the enterprise 1 oversees and includes at least one fulfillment center 42. Because subscribers are trusting the enterprise with their personal information, and very existence in some instances, the use of quantum safe encryption systems are incorporated and are of critical importance across the enterprise.

Quantum computing, quantum encryption, lattice-based cryptography, and crypto currency technologies are adopted by reference as business technologies of a type that may be used in the business enterprise in the present invention. Quantum computing is the study of a still-hypothetical model of computation. Whereas traditional models of computing such as the Turing machine or Lambda calculus rely on "classical" representations of computational memory, a quantum computation could transform the memory into a quantum superposition of possible classical states. A quantum computer is a device that could perform such computation. Quantum cryptography is the science of exploiting quantum mechanical properties to perform cryptographic tasks. Lattice-based cryptography is the generic term for constructions of cryptographic primitives that involve lattices, either in the construction itself or in the security proof. Lattice-based constructions are currently important candidates for post-quantum cryptography. A crypto currency is a digital asset designed to work as a medium of exchange that uses strong cryptography to secure financial transactions, control the creation of additional units, and verify the transfer of assets. Collecting, maintaining, processing, and handing critical information consisting of personal information and items in the most secure manner possible by limiting access to a limited number of authorized users, creating secure backups, and storing physical and digital records and artifacts in a secure manner in secure facilities is a major objective and incorporated into the present invention.

Enterprise 1 business architectures 16, including work groups 35, shown in FIG. 1 operates to manage the artifact 18 collection, storage, processing for design, construction, testing 301, fielding, and maintenance for human-like artificial intelligent entities according to the present invention. The initial biological system 2 provides the initial data for construction of recipient biological 5, bio-mechatronic 6, and mechatronic 7 systems. The enterprise may include performing maintenance, collection, and storage, processing for design, construction, testing 301, and fielding of PDA's. Personal digital assistant 99 systems and devices associated with the enterprise that collect data on biological, bio-mechatronic, and mechatronic systems may be operated upon to develop and produce at least one independent self-reliant biological, bio-mechatronic, and mechatronic entity derived from artifacts. Personal digital Assistant 17 such those described in FIGS. 22a-26c include head mounted systems, smart and virtual speakers, and help robots 95 may be used to collect data that is incorporated into building and independent self-reliant human-like entity 21 that mimics a parent or child biological, bio-mechatronic, and mechatronic being. Still referring to FIG. 1, the delivery systems architecture includes at least one a telecommunication system and logistics system for interacting with the subscriber and user of the enterprise in accordance with the present invention. The enterprise business, information, information systems, data, and delivery systems architecture is preferably connected to a conventional telecommunication system and network. The telecommunications system and network that the enterprise integrated with may be linked to cloud-based applications 27, cognitive agents 302, internet search engines and social media sites 31 that the enterprise and associated public, subscribers, PDA's 30, 300 and entities may operate across. The arrows at the left of the chart illustrate the telecommunications and logistics system over which the users of the enterprise may interact.

Figure 2:
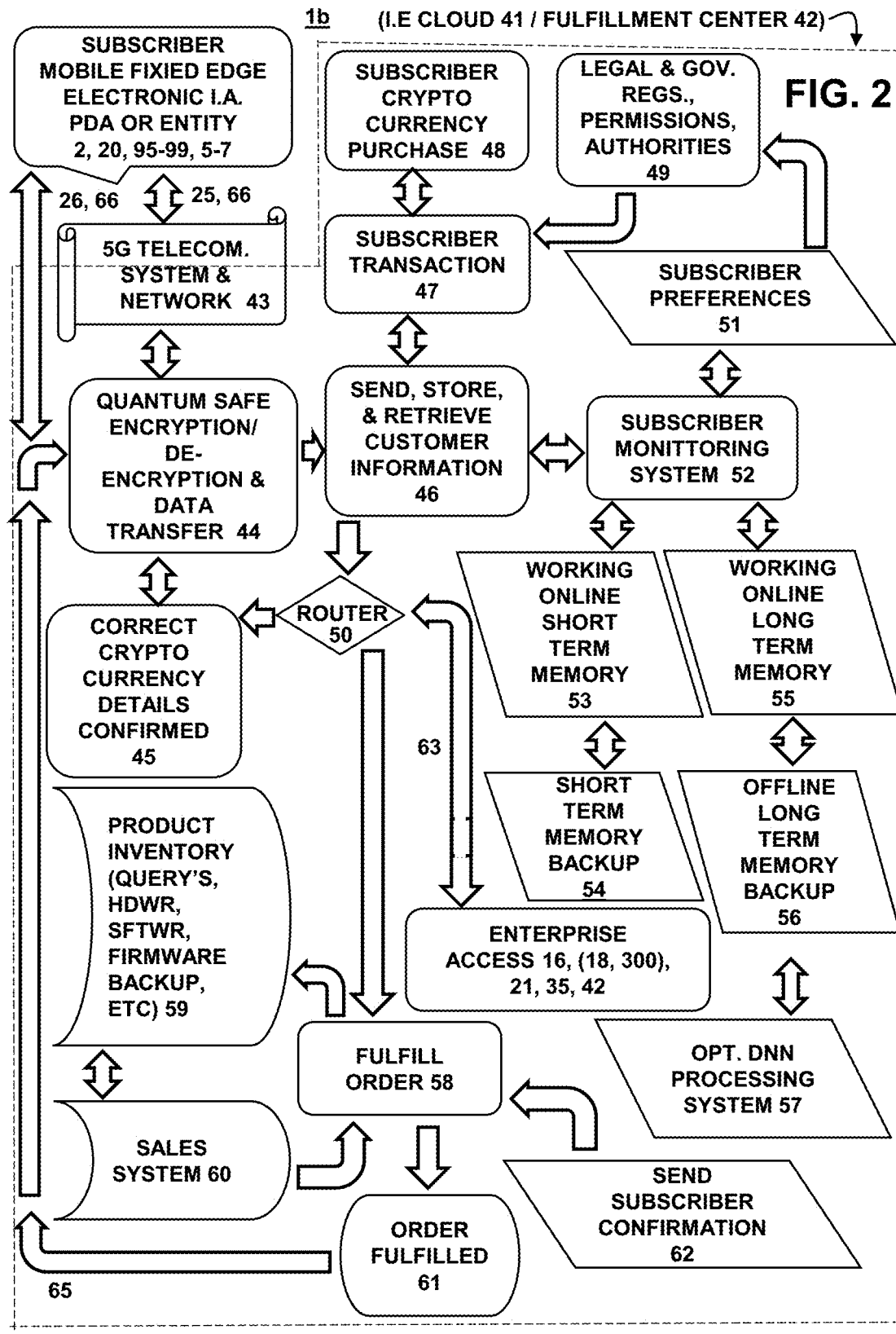
FIG. 2 is a workflow diagram of the human biological, bio-mechatronic, and mechatronic transformation system and method.

FIG. 2 is a workflow diagram that illustrates a human emulation enterprise system and method according to the present invention. The diagram shows the steps and functions within the enterprise process and workflow which may be translated into algorithms ordered in a sequence to achieve human emulation enterprise architecture objectives. The steps are modeled as choices and solutions with inputs and outputs and data stores available for modeling the things that are consumed, produced and stored, retrieved, and maintained in the process. It will be realized by those skilled in the art that functional practices and units of the fulfillment center may be located in one location or separately to reflect best business practices.

For example, in FIG. 2 a parent human being 2 subscriber 20 to the enterprise 1 may use the enterprise architectures 16 to request that his or her brain activity and surrounding data be recorded and correlated into a relational database. The request might come into an enterprise 1 fulfillment center 42 from a subscriber using the internet 19 to conduct a transaction with the fulfillment center. With the parent human being's 2 permission the enterprise would monitor the parent human being's 2 mobile devices and PDA activity and collects sufficient data to build a relational database the mimics the parent human being's 2 perceptions. A Turing Test is a method of inquiry in artificial intelligence (AI) for determining whether a computer is capable of thinking like the parent human being 2. The relational database could use a personalized Turing Test with some personal questions on history to validate the NCC relational database built reflect the memory of the subscriber's perceptions and actions to a certain level. For instance, subscriber can require and acceptance test of his or her historical relational database prior to or once it is put into a simulation or recipient entity that mimics the subscriber to be sure his or her real memory match up with and meets a certain threshold that mimics the subscriber. Only then might the parent human being's 2 subscriber 20 agree to be mimicked in simulation, virtual assistant, or entity 6 or 7. If subscriber 20 observes discrepancies in how he or she is emulated, then at least one subscriber 20, parent human being's, successor being 5, or entity 6 and 7's concern may be addressed. For example, to correct discrepancies in emulation the subscriber's emulation could undergo additional training or adjustments, or the dissonance explained away as part of normal memory loss prior to the relational databased being constructed. The database may undergo a test 301 in a human-like robot 95 like a subscriber 20 selects or in a virtual computer simulation 304 to ensure that the correlated database defines the perceptions of the subscriber 20. Testing out the level of recipient's relational database construct, memory, capabilities, and appearance in various simulated environments is provided in the present invention. Alternatively, the database could be encrypted and sent back to the subscriber for loading on the subscriber's personal server or put onto a storage device and placed in a safety deposit box in his or her bank for storage. Alternatively, the enterprise might license an online application so the subscriber 20 could construct their own correlated database at home or by logging into certain applications on the cloud 41. In this manner an NCC database that mimicked the subscriber's perceptions and actions could be built and her PDA's 95-99 (including wearables), artifacts 18, and help robots 95 that provide information used by a subscriber 20 in order that a such that a human-like robot that mimic's themselves could be built. Then at the request, when a part of or the whole of the subscriber's biological body died, subscriber 20 could have their stored relational database 100 installed into a human-like robot that mimic's themselves and go on with their life as a transformed self-reliant entity. A paradigm shift in how humans define death caused by the present invention is that death may be defined differently. A beneficiary of life insurance or an annuity may be implemented by the subscriber 20 enabling their transformation into a recipient entity 5, or entity 6 or 7. The following applications and patents that are of a type that are adopted as enabling an enterprise are hereby incorporated by reference in their entireties into the present application: Ref. US20160042315A1 Kelli Dawn Field-Darragh Nordstrom, Inc., Priority Mar. 14, 2013 • Filed Oct. 19, 2015, Published Feb. 11, 2016, "System and methods for order fulfillment, inventory management, and providing personalized services to customers"; US 200701685481 A1 entitled "Method and System for Performing Multi-Cluster Applications-Specific Routing" by Atogi et al., issued 19 Jul. 2007; Pat. WO2017097190A1 entitled "Cloud robotics system, implementation method, robot, and robot cloud platform", by (not listed 2015 Dec. 8 (Priority to CN201510894329.1A)

Still referring to FIG. 2, because subscribers are trusting the enterprise with their personal information, and very existence in some instances, the use of quantum safe and safe encryption systems are incorporated and are of critical importance across the enterprise. Quantum computing, quantum encryption, lattice-based cryptography, and crypto currency technologies are adopted by reference as business technologies of a type that may be used in the business enterprise in the present invention. Quantum computing is the study of a still-hypothetical model of computation. Whereas traditional models of computing such as the Turing machine or Lambda calculus rely on "classical" representations of computational memory, a quantum computation could transform the memory into a quantum superposition of possible classical states. A quantum computer is a device that could perform such computation. Quantum cryptography is the science of exploiting quantum mechanical properties to perform cryptographic tasks. Lattice-based cryptography is the generic term for constructions of cryptographic primitives that involve lattices, either in the construction itself or in the security proof. Lattice-based constructions are currently important candidates for post-quantum cryptography. A crypto currency is a digital asset designed to work as a medium of exchange that uses strong cryptography to secure financial transactions, control the creation of additional units, and verify the transfer of assets. Collecting, maintaining, processing, and handing critical information consisting of personal information and items in the most secure manner possible by limiting access to a limited number of authorized users, creating secure backups, and storing physical and digital records and artifacts in a secure manner in secure facilities is a major objective and incorporated into the present invention.

For example, in FIG. 2, a subscriber 20 may access the enterprise 1 cloud 41 network of remote Internet service provider computers and servers on the Internet to access a fulfillment center 42 computer server 73 to access other programs or devices called "clients" using a compatible user mobile and/or fixed edge electronic device or system 43. For example, using a subscriber mobile device, that is 5G capable 209, a subscriber at the edge of a 5G telecommunication system logs into the enterprise architecture 16 information systems architecture 10. The fulfillment center 42 is capable and compatible with the subscriber's electronic device 64, PDA 300, or system 2/5, 6, or 7 referenced in FIG. 1, and the enterprise information architecture 9 system with quantum safe encryption/de-encryption and data transfer 44 over a 5G telecommunication system and network 43. Upon logging in correct crypto currency details are confirmed 45 customer intent to send, store, and receive information 46 is determined. Subscriber transaction 47, subscriber crypto currency 48, legal and government regulations, permissions, and authorities 49 are determined, subscriber preferences 51 are determined, and subscriber monitoring system 52 online short-term memory 53 and working online long-term memory queries 55 requests and backup short term 54 and backup long term storage requests 56 are processed. Additionally, and optionally, long term system working Deep Neural Network (DNN) 57 processing systems may operate in the background to analyze difficult problems. Artificial Intelligence may be used to operate on problems and may be incorporated at any point to analyze data at any appropriate point to solve problems throughout the workflow (indicated by arrows) diagram. Computer processing may be incorporated at any appropriate point to solve problems throughout the workflow diagram. At least one computer router 50 and conventional server 73 system are used to route digital data to the appropriate computer system for automated processing or for manual assistance from an operator at the cloud fulfilment center. Typically, the enterprise 1 fulfillment center business architectures 16, including the work groups 35, are connected together via enterprise access 63 network that runs within and from the fulfillment center 42 though a router 50 that connects to the telecommunication systems and network 25, 26. Order fulfillment 58 involving product inventory 59 management, sales system 60 management, order fulfillment 61, and customer confirmation 62 actions are acted upon by the cloud fulfilment center. Arrows, rectangular shapes, and lines indicate the dependencies and flow of the basic workflow elements that comprise the enterprise architecture shown in FIG. 2. Flow arrow 65 indicates that a telecommunication system and network transmits data in and out of the fulfillment center and flow arrow 66 designates that alternatively the product is transported or shipped to the subscriber. The product shipped provided to or from the fulfilment center may be data or information, or hardware, software, or firmware to answer an enterprise associate, vender, potential customer or a subscriber's query or order.

Figure 3:
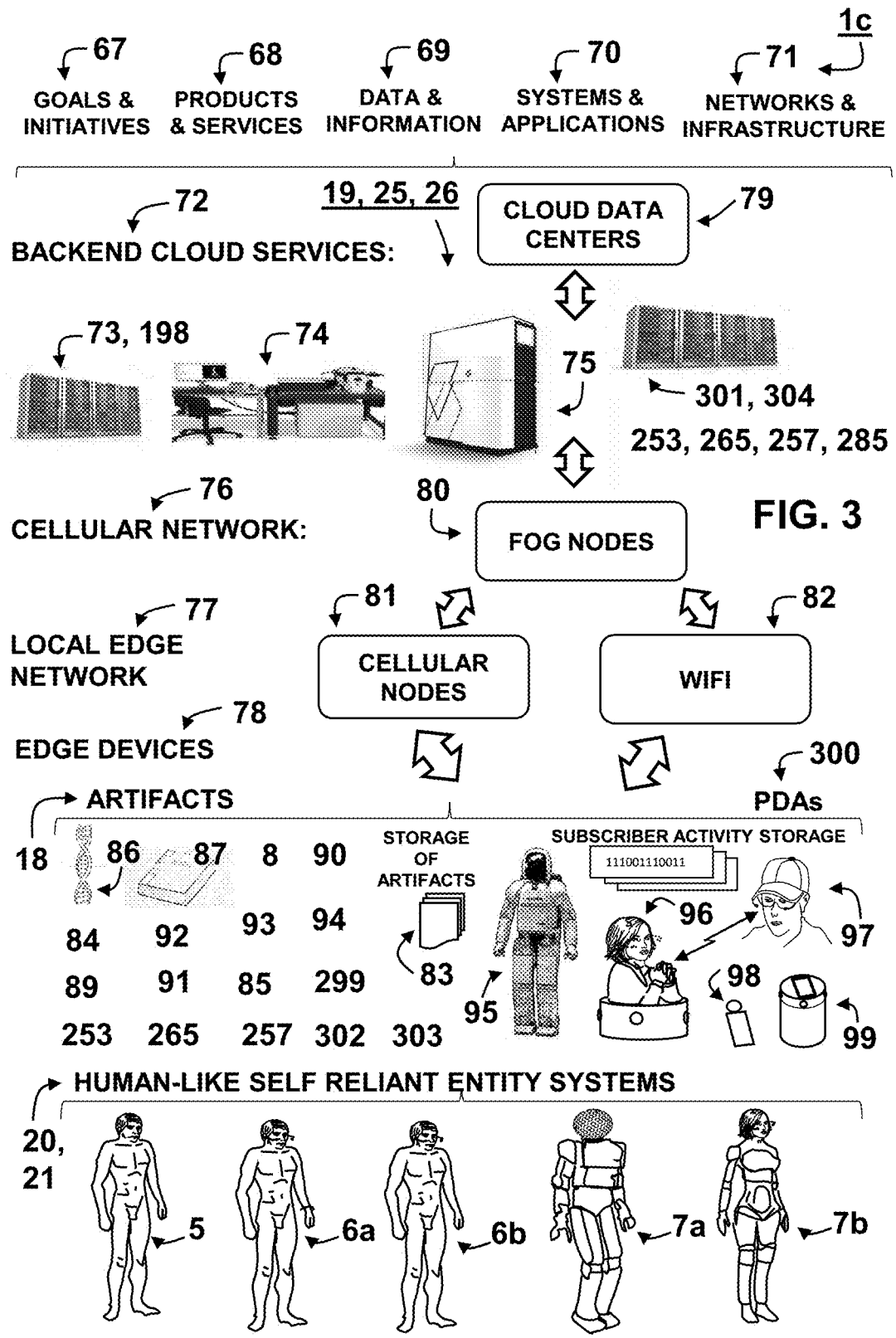
FIG. 3 is a telecommunications support diagram of the human biological, bio-mechatronic, and mechatronic transformation system and method.

FIG. 3 is a schematic diagram that illustrates the relationship and importance of the telecommunication systems and networks 25 to deliver human emulation enterprise capabilities 1c to subscribers 20. A 5G telecommunication system and network system is an example of a telecommunications system well suited and may be adapted for enabling the enterprise 1 system and architectures 16 in the present invention. For example, enterprise capabilities 1 delivered from the business architectures 16 to subscribers include achieving goals and initiatives 67, the delivery of products and services 68, use of data and information 69, use of systems and applications 70, and the utilization of networks and infrastructure 71 to manage and operate the enterprise architecture. For example, enterprise personnel manage and operate machines and equipment 3 to produce, manufacture, and deliver products to subscribers by employing the a 5G internet and/or WiFi telecommunication system in the present invention that is integrated with the business architecture in FIG. 1 and workflow illustrated in FIG. 2. Arrows, parentheses, text boxes, and lines indicate the dependencies and flow of the basic elements that comprise the enterprise architecture diagram shown in the FIG. 3.

Still referring to FIG. 3, the enterprise architecture includes backend cloud service 72 cloud data centers 79 comprising client computer server stacks to manage the data and information throughout the present inventions business enterprise architecture. For instance, computers, routers, and computer servers are incorporated into the present invention to process and store digital personal life histories from client electronic devices. Examples of client devices that subscribers use to transfer information over the web includes PDA's 17, 18, 300 (i.e., see also, FIG. 7) such as wearable's, cell phones, smart speakers, virtual speaker camera display systems, augmented reality headsets, and help-robot systems from which user and recipient NCC databases may be derived. And PDA's 17 that provide continuously coordinated updates to a person's entire ecosystem of devices, and/or provides input into a human-like emulation system 21 such as a subscriber's human-like augmented biological 5, bio-mechatronic 6 (i.e., 6a or 6b), or a mechatronic 7 system. Additionally, product fulfillment centers will require telecommunications and networks to receive orders, handle, and ship physical artifacts 18. As shown near the bottom of FIG. 3, artifacts may include storage of artifacts 83, egg and sperm 84, stem cells 85, genetic material (i.e., DNA and RNA) 86, diary 87, academic records 88, medical records 89, biometrics 90, family photographs and videos 91, cellular phone records and data 92, social media records and data 93 and other types of data, Internet search records and data 94, cognitive agents 302, computer bots 303, nanobot 298, stem cell and pregenorator cells 8, information, and things. Artifact storage may be provided to store artifacts. Artifacts and information from artifacts will be used in constructing PDA's 95-99, and entities 5, 6, 7, 20, 21.

Figure 12:
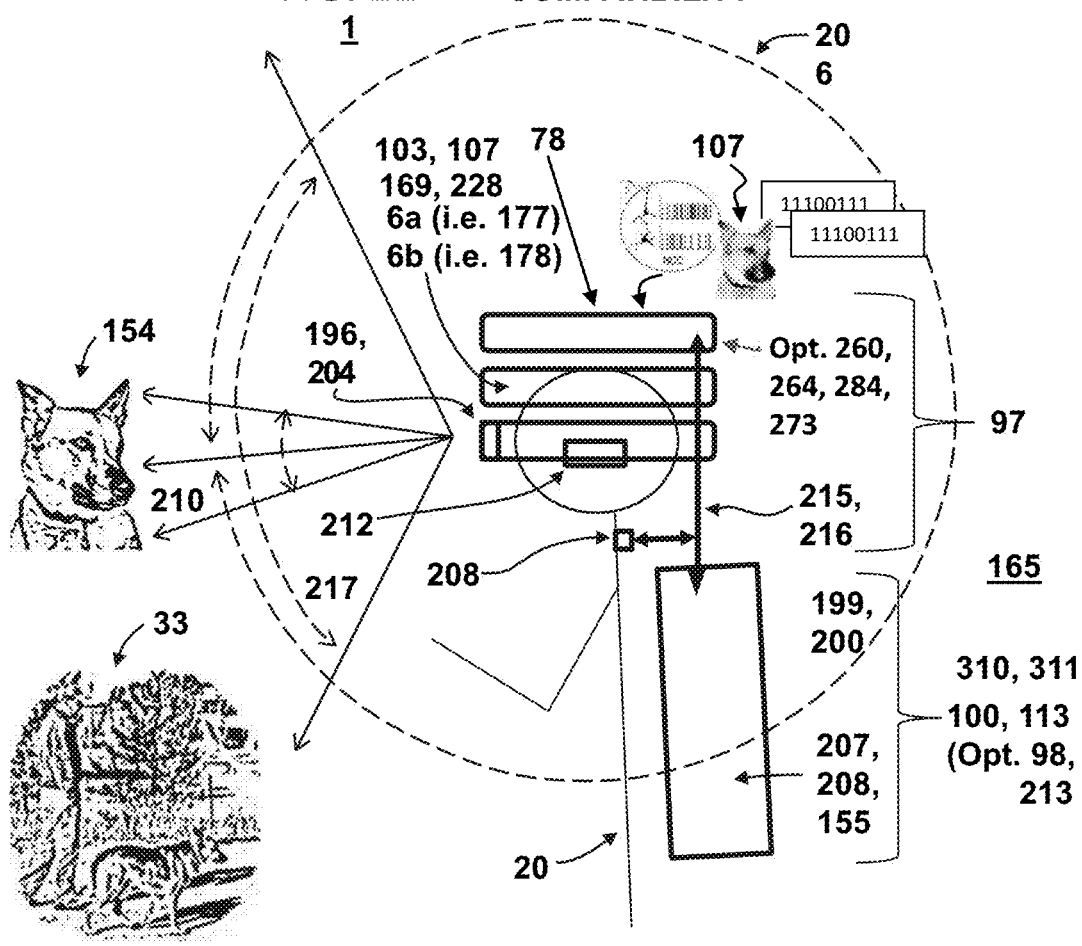
FIG. 12 is a diagrammatic side view of a host computer in a backpack cabled to headgear layout of the user born portable video logging with memory enhancement system in enabled, in accordance with, and supported by the Enterprise Architectures according to the present invention.

In FIG. 3, bilogical system 2 is a parent system with a human-like entity computer system 165, referenced in FIG. 12 and numerous other figures in the present invention, that includes a Life Logging Memory Enhancement Assistant (LLEMA) 155 system that assists in commanding and controlling bio-mechatronic entity 6a and 6b and may be operated to control and command mechatronic entity 7. Biological system 5 is a child recipient system without system 165 that receives information derived from a parent system 2 with system 165 through natural biological senses of seeing, hearing, smelling, touching, tasting. For example, biological recipient entity system 5 a may be a cloned child system 5 a of the original human being 2 into which information derived from the parent 2 is reintroduced through a child 5 a natural senses that stimulates neurogenesis and the forming of new neurons and neural connections in the brain, like progenitor cells 8 or other brain cells 191, which may be activated by presenting a CP that represent a NCC of a human clone 36 system 5 a. Loading of a cloned person may also be accomplished using this technique to refresh a human's memory (i.e., an Alzheimer patient). Still alternatively, biological recipient entity system 4, 5b may be a child recipient system without system 165 that receives information derived from a parent 2 system 165 by injecting stem cells into the child system 5 b. The stem cells may be activated and loaded with CP data that represents NCC by presenting a Conscious Perception (CP) in the real-world surrounding environment that represents a NCC that stimulate the injected stem cells 85 via biological systems natural biological senses of vision, hearing, smelling, touching, and tasting. Still optionally, biomechatronic system 6 is a child recipient system with system 165 that receives information derived from a parent system 2 with entity computer system 165. Biomechatronic system 6 includes a natural biological neural network and artificial neural network. For example, biomechatronic system 6 a, 106 includes an entity computer system 165 that includes a wearable headgear with a wearable head mounted display 239, a support apparatus 240, and a wearable non-invasive brain activity sensing 177 and/or 178 with a brain stimulation system operates to sense, log, record, process, derive, and operate upon the brain and brain data to derive NCC from CPs. An example of a wearable non-invasive brain activity sensing headgear 97 and stimulation system of a type like that used in entity 6 a is disclosed in U.S. Pat. No. 9,730,649 and other referenced related patents by Jepsen 177 and incorporated in full by reference into the present invention. A non-evasive cell phone interface that is compatible with the present embodiments of the non-evasive brain activity sensing system like Jepsen's system, and that could be targeted by evasive brain activity system, in the present invention is described in the article: "A Cell-Phone Based Brain-Computer Interface for Communication in Daily Life", Yu-Te Wang et al., University of California, San Diego Calif., March 2011, Journal of Neural Engineering, by PubMed. Alternatively, a biomechatronic system 6 b that includes an entity computer system 165 that includes a wearable headgear 97 b with an invasive brain activity sensing and stimulation system that operates to sense, log, record, process, derive, and operates to derive NCC from CPs. An example of a wearable system is disclosed in a white paper by Elon Musk & Neuralink™, entitled "An Integrated Brain-Machine Interface Platform 166 with Thousands of Channels", 16 Jul. 2019, by Neuralink™, Corporation. The Neuralink™ Platform 166 is incorporated in full by reference into the present invention as an intrusive wearable brain interface. Finally, optionally, mechatronic system 7 comprises an entity computer system 165 that includes a computer system that is mechanical and electronic in nature, incorporates at least some information derived from a parent 2 NCC and CP data, which operates to sense, log, record, process, build upon the derived NCC from CP data using mechatronic system 7 capabilities. Mechantronic system 7a portrays a mechanical looking entity 7 a that may include a nano-printed micro-bead lens 249 that serves as both an integrated visual capture and display system 260 (shown); or may be constructed as an integrated array that includes a directional speaker 276, a directional audio microphone 275 system, a 3d panoramic video sensing 160, and a (Light Imaging Detection and Ranging) LIDAR 278 system. Alternatively, mechatronic system 7 comprises animatronic features 106 that cause the entity 7 b not only to act but also to look more like a biological human 2. It will be understood by those skilled in the art that digital stimulation of neurons in the brain that represent a particular NCC can be achieved by stimulating the same biological neurons that represented the originally derived NCC in the brain that was recorded by the brain activity sensing system enabling communication between a human and a machine using technologies such as a synaptic chip. Subscriber/user/agent/recipient requests via the cloud, local enterprise fulfillment centers 42 to maintain personal emulation storage 83 on a server 73, PDA devices 95-99, and entity 5, 6, 7, 20 capabilities.

In the present invention fog computing is a system-level telecommunication system and network architecture, providing tools for distributing, orchestrating, managing, and securing resources and services across networks and between enterprise 1 supported devices 5, 6, 7, 20, 95-99 that reside at the local edge network 77 of the present invention to send, receive, and interact with edge devices 78.

Edge computer architectures place servers, applications, or small clouds at the edge. Fog computing extends cloud computing to the edge of an enterprise's network. In the present example, the telecommunications system and network incorporates fog nodes 80 to connect subscriber and fulfillment centers together by incorporating backend cloud service cloud data centers, cellular network 76 fog nodes, local edge network cellular node 81 and/or Wi-Fi 82 and edge devices 78. And artifacts 18 will likely originate with the subscriber that is going to be emulated. Fulfillment center 42 functions may be placed with backend cloud service cloud data centers, cellular network fog nodes, local edge network cellular node or Wi-Fi locations to interact with subscriber's physical artifacts, and entities. The organization herein represents an example of an organizational structure and distribution which may vary without departing from the concept and spirit of the human emulation enterprise system and method according to the present invention. Also known as edge computing or fogging, fog computing facilitates the operation of compute, storage, and networking services between end devices and cloud computing data centers. Fog computing with low latency is critical in the present invention to reacting to devices and biological beings that wear and operate life critical systems such as help robot 95, and human-like bio-mechatronic and mechatronic entities. For example, Novatex Solution's offers a telecommunications system and network of a type that is incorporated into and compatible with the present invention that offers the low latency from edge devices to backend cloud services that reduces latency. Five Gigabit (5G) Telecommunications system compatible with the present invention and adopted by reference for use include those described by Rupendra Nath Mitra, and Dharma P. Agrawal in Science Direct entitled "5G mobile technology: A survey", dated 22 Jan. 2016.

Figure 4:
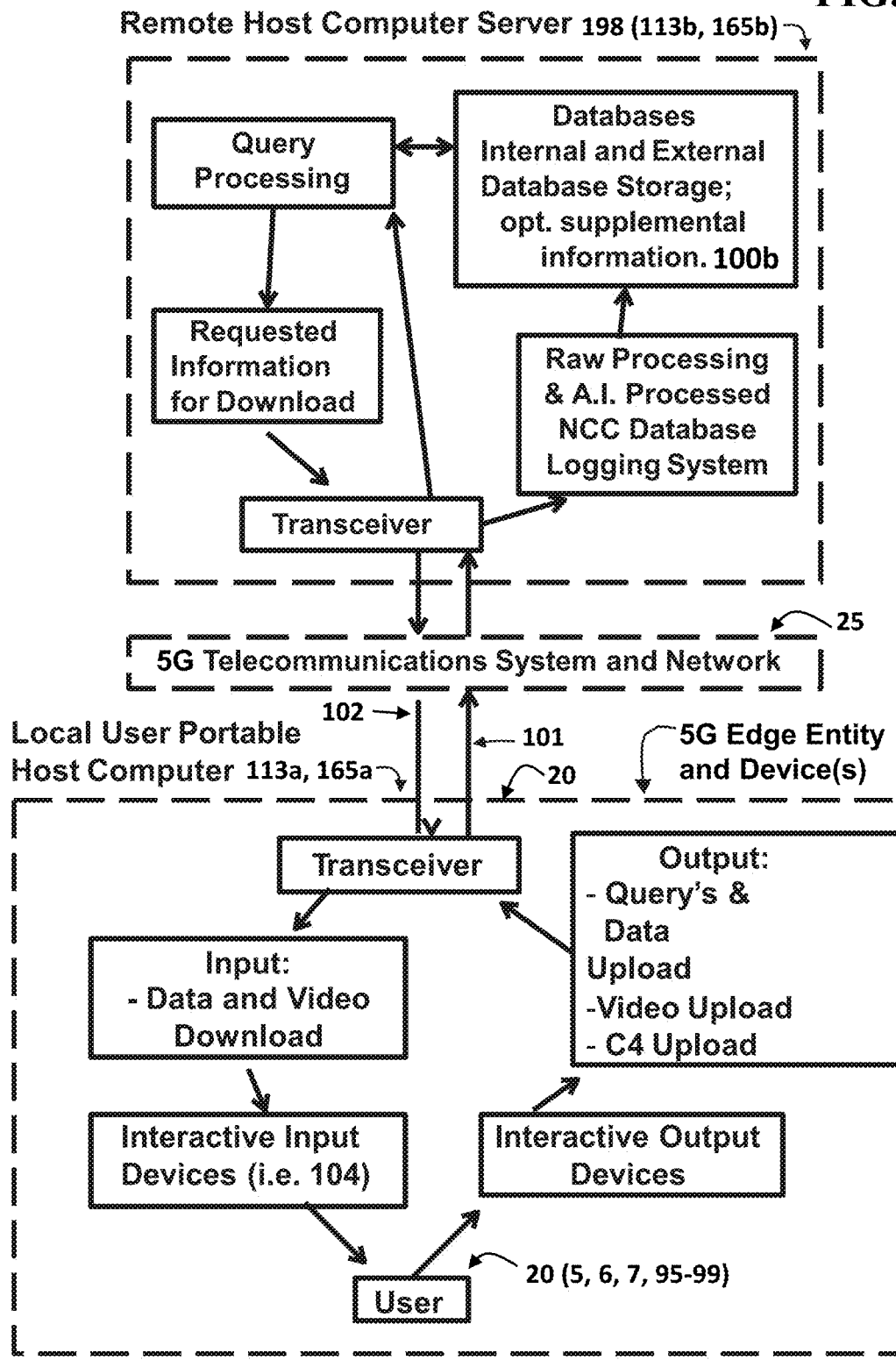
FIG. 4 is diagrammatic representation of a two-way telecommunication embodiment of the invention in which a message is transmitted between a Sender and Receiver which may comprise beings, machines, or bio-mechanical systems.
Figure 5:
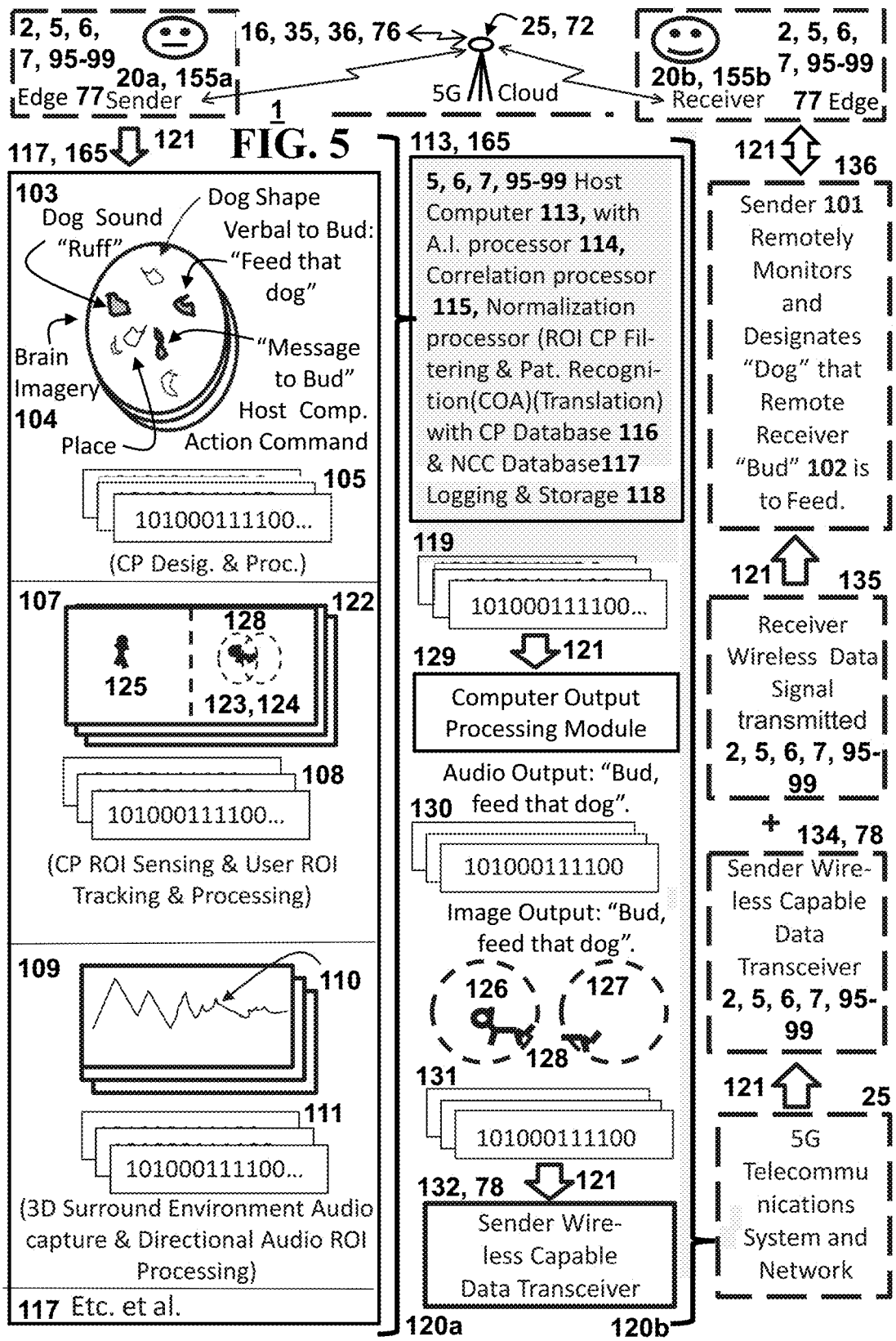
FIG. 5 is a schematic diagram that illustrates systems and methods that data and information logged and derived from the internal physiological sensor systems and external surround sensing systems processed by the present invention may be input into a recipient being, machine, or bio-mechanical system in order to facilitate enhancement, transcendence, replacement, or substitution of at least some portion of a recipient being, machine, or bio-mechanical system in accordance with the present invention.

FIGS. 4 and 5 are block diagrams that illustrate using subscriber 20 using an self-reliant human-like system 21 derived from the of operating the enterprise system 1, 100 over the telecommunications system and network 25. These embodiments of entity 21 include biological 5, biomechatronic 6, and mechatronic 7 systems that comprise at least one a natural biological neural network, an artificial neural network, or alternatively both the case of biomechanical system. The Neural Correlates of Consciousness (NCC) of natural biological neural network within the brain of a human may be captured by incorporating a brain activity sensing system and translating the memory into a computer language that forms a database of the minimum neural activity necessary that is required for that person required to define a conscious perception of something. The NCC of the neural network an artificial neural network may be captured in the memory of the computer or in a mechatronic system. Biological 5, biomechatronic 6, and mechatronic 7 systems may include neural activity sensing systems that are non-invasive or invasive with respect to the outer covering of system 21. For instance, a biomechatronic entity 6a may incorporate wearable headgear that is worn on a human's natural head that functions as a brain activity sensing system that records neural activity within the brain. Alternatively, a biomechatronic entity 6b may incorporate a brain activity sensing system implanted inside head of a user to record neural activity in the brain of a user.

Still referring to FIGS. 4 and 5, the of system 1 that comprises a cloud computing arrangement for video logging and memory enhancement comprising a local user portable host computer 104 personal digital assistant 300 or human-like entity/system 21, and a remote host computer 165b.

FIG. 4 and FIG. 5 the illustrate a logging and enhancement system 100, 165 incorporates a 5G telecommunication system and associated telecommunications system and network 105, 25, like the global information grid (GIG), which includes the Internet 19. Some components of the system 100, 113, 165 may be placed in remote locations apart from a user of the system such that it is unnecessary for the user to carry all components of the system 100, 113, 165. In certain embodiments of the invention, this is advantageous because carrying less components reduces weight, required electrical power, and component space for system 100, 113, 165 some of which must be borne by the user. And furthermore, it allows what is carried by the user to be carried less conspicuously. The basic subsystems that are placed on or in the user's head include a brain activity sensing system such as a portable and panoramic video sensor system with dashed lines 206 indicating spherical panoramic field-of-view coverage and dashed lines 217 indicating the user's wide-field of view coverage. Brain activity systems that generally record brain activity signatures as imagery (i.e., fMRI) or signals (i.e., EEG) representing neural activity of spiking neurons and synaptic activity between neurons by time and location may be incorporated into the present invention. For example, activity like the Openwater™ and Neuralink™ brain activity sensing systems capture that is referenced and discussed later in the present application. Additionally, and optionally, a voice microphone and/or sub-vocal recognition system is placed on the head or upper body of the user. Preferably, eye tracking and head tracking sensors are also located on the user's head or upper body. The brain activity sensing system may be mounted onto any biological system or bio-mechatronic system with a brain to record neural activity such as illustrated in FIGS. 11-18, FIG. 25, and FIG. 26. Other components may be carried by the user other than on his head but in a communicating manner to the sensor systems on his head or upper body so that signatures may be transmitted to a remote device for processing. For instance, audio mechatronic audio sensing and logging system 112 includes an audio sensing system 109 records and audio signature 110, the audio signature converts the data into computer code, where it is operated upon by entity system 165. For instance, brain activity sensing 103, image signature 104 processing, and image signature conversion into computer code 105 is operated upon by entity system 165. And where a region-of-interest (ROI) tracking system 107 sense and derives the CP of user 2, 5, 6, 7 and subscriber 20. With ROI tracking systems 107 such as PDA or worn video camera and eye and head tracking systems 107 and other know systems. Where the ROI tracking system 107 converts the data to computer code 108 that is operated upon by entity system 165. It will be known to those that other sensor modality sensing and pre-processing system may record internal and external data in and about the user as designated by Etc. et al 117. Transmission between sending subscriber 20b and receiving subscriber 20b may be from the sensor systems borne by the user and in a communicating device to a portable electronic device borne by the user such as a PDA, cell phone, smartphone, laptop, headgear, or other computer with wireless connectivity to an associated telecommunication system and network 25. The brain activity sensing portion of the system connects to other electronic devices that make up the system 100, 113, 165. For example, the electronics portion of the system may be located as part of a user's headgear, backpack 213, belt pack, integrated into clothing on one's lower body, or mounted in any suitable manner described as shown in FIGS. 11-18, FIG. 25, and FIG. 26.

Still referring to FIG. 5, the entity computer system 165 and host computer 113 process the information preprocessed by the internal brain and external surrounding and peripheral environment image sensing system data 108 logged and converted into computer code 119. Entity computer system 165 and host computer 113 include artificial intelligence processing 114 that can be applied to correlation processing 115, normalization processing, ROI CP processing, pattern recognition, course of action decision making based on thresholds, human to machine and machine to human interface translation processing, including voice synthesis and other machine learning processing capabilities for deriving and operating upon the CP Database 116 & NCC Database 117 and Logging & Storage 118 the data into non-volatile memory. Processed computer code from the entity computer system 5, 6, 7, or a PDA 95-99 is then transmitted to Computer Output Processing Module 129 and related systems for output. For instance, to transmit a message from the sender to the receiving entity or PDA (i.e., audio Output: "Bud, feed that dog" in computer language 120 and some portion of the panoramic imagery 126 and 127 from image frame 128 into computer language 131, as indicated by arrows 121, through a wireless transceiver 132 edge device 78 of the 5G telecommunications system and network 25 to the receiver 134 edge device 78. So that the sender which comprises entity system 5, 6, 7, 95-99 can take action and both sender 20a and receiver 20b may communicate using one way or two way telepresence to interact on information transmitted in near real time. In this manner a user subscribing entity may exchange information using mental telepathy, video, or audio, or various taxonomies using the system 165. The data signal comprising audio and imagery is by the entity system 5, 6, 7, 95-99 on the receiver end of the communication so the subscriber 20a can remotely monitor and designate the CP ROI 123 "dog" that remote entity 5, 6, 7, 95-99 subscriber 20b "Bud" is to feed 136.

Figure 6:
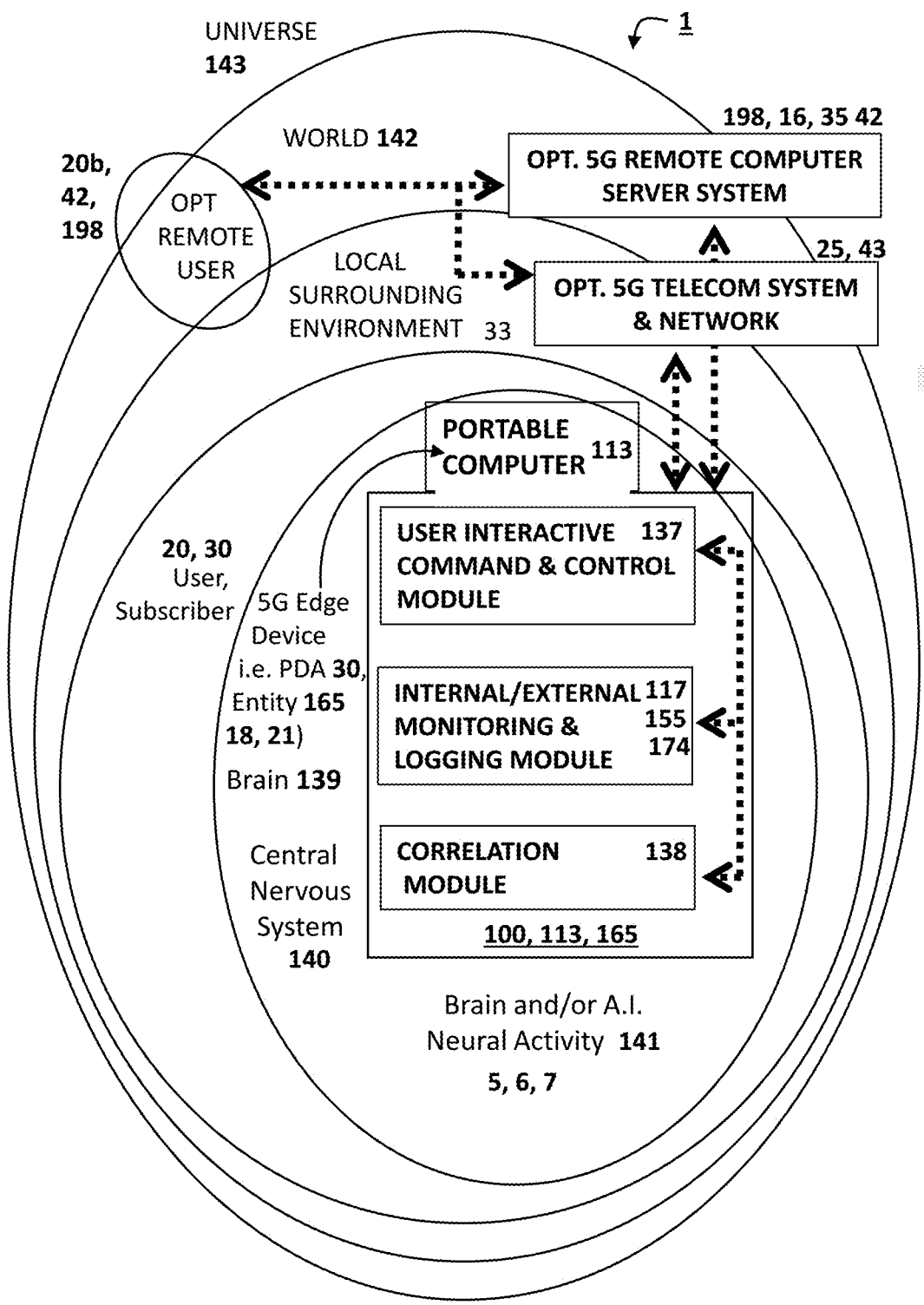
FIG. 6 is a block diagram of the portable interactive data logging and memory enhancement system that describes the overall concept and major components of the invention that support deriving a relational computer database that captures a parent human's perceptions that may be transferred and operated upon in a biological, bio-mechatronic, mechatronic system.

FIGS. 6 and 7 illustrate embodiments incorporating system 100, 113, and 165 into a telecommunications system like described in the 5G telecommunication system shown in FIG. 3 of the present invention. The 5G telecommunication systems described in FIGS. 6 and 7 facilitate interaction between fulfillment centers and subscribers at the edge of the telecommunication system as illustrated in FIGS. 1, 2, 3, 25, and 26 that enable the human emulation enterprise system and method.

FIG. 6 illustrates a schematic diagram of enterprise system 1, 100 which comprises an embodiment of the invention. The enterprise 1 system provides the business architectures 16 to facilitate a human 2, 5 to machine 6, 7; and machine 6, 7 to human 2, 5 transformations. Thus, the entity computer system 165 includes embodiments that supports transformation of human to machine and machine to human design configurations. The present invention 165 facilitates interaction with a natural human brain 139 and that is part of the human central nervous system 140 and/or interact with the cognitive computing systems that have artificial neural networks 141 that support a self-reliant human like entities 21 like those described and enabled by the enterprise 1 disclosed in the present invention. The enterprise system 1, 100 includes a portable host computer system 100, 113, 165 that comprises a user interface that includes an interactive command and control module 137 internal and external sensing module monitoring and logging module 117, 155, 174 and a correlation module 138. Module 137 processes the host being user 20, subscriber 30 commands that control the portable computer 113 that controls module 174 and correlation module 138. Command and control module 137 is operated to specify which data, information, and/or media content that the system 113 acts upon. Internal and external sensor data and information is transmitted to the internal and external sensing monitoring and logging module 174. Module 174 includes physiologic activity, periphery, and surrounding environment sensor units. Correlation module 138 includes a feature, quality, and/or a media content identification unit commanded by control module 137. Module 174 operates to command and control the transmission of data and information to and from the correlation module 138 along with other stored or incoming data which may be transmitted to system 113 over a telecommunications system and network 25. User commands and logged information are operated upon to draw relationships utilizing correlation module 138. The device 113 is borne by the user 2, and subscriber 20, and may interact over the telecommunications system and network 25 with another user 20b or a remote computer server system 198. The enterprise system 1 exists in the local environment 33, world 142, and universe 143 where remote servers 198 and subscribers 20b will exist. Fulfillment centers 42, described in FIG. 1-FIG. 3, may exist in deep space and communicate back to earth 148 via communication satellite(s) 153, as shown in FIG. 26a. A space station 307 that orbits earth may serve as a staging platform for spaceship 146. Additionally, spaceships may include 3d printers and materials that are operated upon to maintain and produce PDA and entities 5, 6, 7, 100, 113, 165 and the like. Additionally, in the present invention the entities and spacecraft 146 may be powered by a fusion reactor 147 that generates electrical power.

Still referring to FIG. 6, the telecommunication system and network 25 may include at least one remote server 25, 43, 73 that communicates with and shares functionality with other servers, networks, and portable computers. For example, in the present example the telecommunication system is a 5G telecommunication system and network 25, 43. The telecommunication system includes a remote server 198 that preferably connects to local edge network 77 subscribers 20 edge devices like an entity 165, 21, PDA 30, 300, and also to backend cloud service 72 cloud data centers 79 which typically will include venders 29, cognitive agents 302, business architectures 16, and systems work groups 35, and fulfillment centers 42 shown in FIG. 3. Portions of system 104 a host computer, 113 a portable computer, may be comprised of separate connected components to realize computer 104 and 113 in the present invention, depending on the embodiment of the present invention. Within the present invention various computing devices may be used to implement the internal and external sensor system monitoring and logging module 109, 174 and correlation module 111, 138. The system 104, 113 may comprise various components, to include a networked computer, a server, a collection of servers and/or databases, a virtual machine running inside a computing device, a mobile computing device, a PDA, cell phone, smartphone, a tablet PC, a robot, or man-machine integrated system. For example, computer processing of sensor signatures gathered by module(s) 109, 174 and processed by correlation module 111, 138 may be accomplished on one or more remote computer servers 106, 198 systems in the world or universe or computer 104, 113 systems in the local surrounding environment 33, 160.

FIG. 7 illustrates the enterprise 1 system and method that the present invention employs to identify the Neural Correlates of Consciousness (NCC) 155, 166. The enterprise system incorporates a diverse and novel business architecture that incorporates new subject matter in the instant invention at an economy-of-scale to transform the life-cycle of predecessor and successor biological, biomechatronic and mechatronic entities at a personal level. In operation the systems 100 and 165 described above in FIG. 6 may be implemented in a computer hardware and firmware configuration shown in FIG. 7. FIG. 7 is a diagrammatic perspective of an embodiment of the transformational process of the human life-cycle transformation enabled by the new subject matter presented in the present invention. In this instance, the conscious perception (CP)(which is also be referred to as a "Conscious Percept" by those in the profession) 161, 158 in the mind of the user 101, 2, 5, 6, 7, 20 in the local surrounding environment 160, 33. In this example, the subject of the user's CP 158 is a "dog" 159, 154, located in the user's fine focus 210 field-of-view 161, 162 in the surrounding environment 33. At least one brain activity sensing system 103, and other sensing system 106 (i.e., video camera, LIDAR, eye tracking) record and pre-process sensing system information for additional processing and transfer the information in computer language 108 in at least one the user or recipient's entity portable computer system 165. The user 101, 162, 5, 6 brain 139, 167 activity 141, 165 causes neurons 164 to fire and the neural network activity is detected by the brain activity sensing system 103, 141 of system 1, 113, 155, 165, 169 which generates electronic signatures 156, 163 that are digitized and processed by the entity computer system 165. The brain activity 141, 165 is correlated with panoramic video 160, 168 imagery and audio signatures 159, 169 also captured by system 6, 113, 155, 165, 169 that are the focus of attention of the user 2, 6, 20, 101. Correlation of the brain activity and video signatures is then derived by performing computer operations comparing the brain, image, audio, and optionally Conscious Perception (CP) tracking system 170, signatures in order to deduce the conscious percept 158, 161 and identify the neural correlates of consciousness 157 of the being 2, 6, 20 at a given time and place during the life of the being. The dashed lines 168 surround comprise the computer processing system 165 borne by the user/subscriber 2/20, 5, 6, 7. Black arrow 167a indicates the flow of biological and machine sensing modules 103, 278, 305 pre-processing that is part of computer system 165 borne by recipient subscribers 20, 5, 6, 7. Black arrow 167b indicates the flow of information operated upon by the host computer processing subsystem 113 that receives the pre-processed sensed data, operates on the sensed data, and processes sensed with historical information to derive outcomes of entity computer system 165 that commands and controls recipient subscribers 20, 5, 6, 7. Host computer 113 includes the LLEMA system 155, the internal and external sensing monitoring system 174, and correlation system 173, relational database 176. The relational database 176 includes what conscious perception 175 equates to what neural correlates of conscious 176. Sensory perceptions of the surrounding environment drive the entity computer system 165 that comprise the cognitive computer system with at least one A.I. and/or A.I.-like processing to derive solutions that determine the actions and additional processing of the entity 5, 6, 7. The entity 5, 6, 7 electrical power subsystem 173a and mobility and dexterity servo subsystem 173b are also monitored and controlled by the host computer system.

Still referring to FIG. 7 of the present invention, patent application Ser. No. 15/258,336 filed on 7 Sep. 2016 entitled "System for Correlating Brain Activity with Data From A Surrounding Environment" (grated as U.S. Pat. No. 11,055,356 B2) by Ritchey et al., illustrate embodiments incorporating a Neural Correlates of Consciousness database derived from a person wearing system 6, 113, 155, 165, 169. Wherein said NCC database is operated upon by a PDA or recipient human-like bio-mechatronic 6 or mechatronic 7 system. When a purely mechatronic system is used the brain activity sensing system portion of the entity computer system 165 is not required. And the mechatronic system senses itself and the surrounding environment. And the mechatronic system/entity's results of sensing and processing using artificial neural network are recorded in memory. So in summary, in the present invention the natural neural processing in the brain functions as the central processing unit for a biological system 2, natural biological neural processing operates implanted or sensed data derived by the logging system without use of wearable or implanted electronics in the recipient biological system 5, the natural neural processing in the brain and artificial intelligence neural processing cooperatively and complementarily function together in the bio-mechatronic system 6, and in the mechatronic system 7 the artificial neural network conducts cognitive computing similar to a human only as a human-like entity. Hence, in the present invention the enterprise 1 system provides the business architectures 16 to facilitate a human 2, 5 to machine 6, 7; and machine 6, 7 to human 2, 5 transformations.

FIGS. 6 and 7 demonstrates stimulating or downloading historical data and information derived from the human internal/external logging system 6, 113, 117, 155, 165, 169 is operated upon by the entity computer system 165 to restore or enhance memory and cognition of a recipient biological being or at least one a recipient human 5, human-like bio-mechatronic 6 and mechatronic 7 system. FIG. 7 illustrates data and information 100 derived from the portable LLEMA system 103, 155a, 165 at time one T1 to the nth from user 5, 6, 20 is operated upon to provide utility to a recipient 20 at time two T2 193 to the nth by operating system 6, 113, 155, 165, 169. In FIG. 7 the dashed line indicates the functions commanded and controlled by then entity computer system 165. The same system 103, 155a, 165 operated at time one T1 to record, process, and log data and information may be operated by a user to recall, process, transmit and input data and information for input to a recipient 20. Time one T1 and time two T2 may comprise an instance or Time T1 to T 2 may comprise period of time. For example, Time 1 T1 and time 2 T2 may be near real time (i.e., less than a few milliseconds) or very far apart in time (i.e., years). The inner oval shape in FIG. 6 represents represents the brain 139 of the user 5, 6, 20. For example, user 5, 6, 7, 20 at starting time one T1 activates the portable system 103, 155a, 165 at least one sensor monitoring module 174 to record brain activity signatures and external sensor signatures of the surrounding environment over a given timeframe. The signatures are stored as data and information 100 in the memory of computer 103, 155a, 165 and/or remote computer server 198. The data and signatures from sensor module 174 are read into memory and are operated upon by the computer 113 and/or remote computer server 198. Signature data and information is processed in correlation module 138 of computer 165 and/or remote server 198 to identify relationships and NCCs. A record of the NCC's identified along with supporting data and information denoting the relationships between the data and information is placed in and comprises the NCC database 115 which is stored in the memory of computer 165 and/or remote server 198. Supporting data and information preferably includes metadata that relates the derived NCC's information back to a filing system that comprises external signatures (i.e. video imagery signatures and audio signatures, geo-spatial data, sub-vocalization data, etc.) and internal signatures (i.e. brain activity and brain activity patterns). The operator of system 6, 113, 155, 165, 169, which may be the user 5, 6, 7, 20, who operates an interface device to set the parameters and metrics of the system that define thresholds of the data and information that define the NCCs of a specific user. System hardware and software designers will typically construct system's 5, 6, 7, 95-99, 113, 155, 165, 169, including the GUI, so that the system 165 and/or 198 is operable to achieve the results described herein. The NCC database symbolizes the fundamental digital representation of how the user perceives the world.

Still referring to FIG. 7, computer 165 may incorporate various types of filing systems and tags to organize the data. For instance, the data may be filed or tagged by chronological, geographical, subject matter, or another method to facilitate memory storage and retrieval objectives. Once established the NCC database may be updated at any later time two T2 to the nth by operating the system 165 and/or remote computer server 198. The NCC database may be updated at follow-on data search engine and logging instances. And checkpoints of the NCC data may be stored and follow-on data search engine and logging instances to create back-up databases. Data and information recorded by system 165 may be offloaded over a wired or wireless transceiver 132 to a remote computer server system 198 for computer data and information storage and processing to reduce the demand on portable system 165. System 165 and 198 may be operated in a selective or continuous mode during the lifecycle of a user. Redundant, repetitive, or unwanted data and information may be filtered out through computer processing at the time of recording or later either automatically, based on a rule set, or by a user or operator operating system 6, 7, 113, 155, 165, 169. User and operator querying and downloading the NCC database, a portion of the NCC database, information and data the NCC was derived from, derivations from the NCC database, or an update to the NCC database may be accomplished by using various database filing and query systems known in the computer industry. For instance, related NCC data and information may be stored on computer media familiar in the computer industry in temporary and/or permanent memory of system 6, 7, 113, 155, 165, 169. In the present example a dog 154 in the surrounding environment 33 is sensed by an entity 5, 6, 7, 20 is wearing senses, records, processes, and presents information. The system 5, 6, 7, 95-99, 113, 155, 165, 169 acts upon signatures that equate to the Conscious Percept (CP) 158 representing the dog. Information related to the Conscious Percept of the dog is correlated with signatures of a subject, activity, thought, or memory to derive and define the Neural Correlates of Consciousness (NCC) 155. The NCC, data, and information from which the NCC's are derived represent a computerized relational database of information on how the subscriber 5, 6, 7, 20 perceives the dog 154 and other percepts derived in at least one the subscriber's neural networks of brain 139 and/or the entity artificial neural networks of entity computer 113, 165. At least some portion of the NCC and/or corresponding data and information, for say a "dog", is passed on to a recipient 20. In the present invention a natural human being 2 is transformed into an entity 5, 6, 7 when he or she integrates his or her biological self to some extent or fully with or into an internally or externally manifested computerized device with artificial intelligence that at least to some extent shares decision making authority and control derived and as depicted as a recipient human-like entity 5, 6, 7 described in the present invention. Additionally, a self-reliant human-like entity also has a structure that has human-like mobility and dexterity and a rechargeable energy generation system.

The lower half of FIG. 7 illustrates an embodiment of the present invention in which at least some portion of the NCC database derived at time one T1 as a subscriber 20 from a human user 2 as entity 5, 6, 7 and downloaded at a later time two T2 into the memory of a recipient 20. System 5, 6, 7, 113, 155, 165, 169 components and recipients 20 are bounded and defined by dashed line 168 in order assist in illustrating the case example that takes place at time two T2. A recipient 20 in the present invention may be a biological living being with a brain 139 (i.e., a person/a human being 5), a machine 302, 7 (i.e., a robot 196), or combination thereof (i.e., a bio-mechanical system 6a or 6b). The recipient 20 may be a user 2, who becomes entity 5, 6, 7 when becoming a subscriber 20 who bore system 103, 155a, 165 and logged the data that is to be presented or a recipient who did not log the data that is to be presented with the logged data and or information derived from the logged data. Furthermore, recipients 20 may themselves incorporate a computer system 6, 7, 113, 155, 165, 169 to create their own logged data and information for personal use or shared use with other recipients. And optionally, a recipient 20 user may be a biological, biomechatronic, or mechatronic clone of the user 2, 5, 6, 7, 20 whose appearance is identical to the user who logged the data. Data and information transferred from system 103, 155a, 165 and/or 132 to a recipient 20 may be correlated or not correlated, depending on the design of the recipient whom the information is to be input into. Data and/or information input into a recipient 20 is processed to be compatible and tailored for input into the recipient 20.

FIG. 8a-9c diagrams graphically illustrate that signals and/or images derived from internal and external sensors may be translated into and represented in computer language for computer processing and archival purposes. FIG. 8a is a top view of fMRI tractographic reconstruction 186 of neural connections in the brain recorded by a Diffuse Tensor Imaging (DTI) to illustrate neural brain 104 activity. For instance, FIG. 8a illustrates that synaptic 163 connections that connect to at least one neuron 164 may be imaged and operated upon by a computer to identify NCC's that represents the word "dog" 180 that correspond to a CP.

FIG. 8b is an enlarged view of neurons firing and electro-chemical pathway currents activated 190 in the brain 104 by using calcium oscillation. For instance, FIG. 8b illustrates that synaptic 163 connections that connect to at least one neuron 164 may be imaged and operated upon by a computer to identify NCC's that represents the word "dog" 180 that corresponds to a CP. The CP that a human is focused upon are measured and correlated with brain activity 103 to derive a digital "thumb print" of the human mind. Both Openwater's™ and Neuralink™ brain imaging technology are types of brain activity sensing systems that provide data that may be incorporated in full by reference into present invention to provide CP and NCC data necessary to enable building a "thumb print" of a person's mind. The thumb print is used to sense, record, and process information about a user for later use in constructing and training Artificial Intelligence (A.I.) capable devices like PDA's and human-like entities in accordance with and supported by the Enterprise Architecture according to the present invention.

FIGS. 9a, 9b, and 9c of the present invention, patent application Ser. No. 15/258,336 filed on 7 Sep. 2016 entitled "System for Correlating Brain Activity with Data From A Surrounding Environment" (granted as U.S. Pat. No. 11,055,356 B2) by Ritchey et al., illustrate embodiments incorporating a Life Logging Memory Enhancement Assistant (LL-MEA) 155 system and a human-like entity computer 165 system shown in FIGS. 5-7 and over a telecommunications system like a 5G telecommunication system and network as shown in FIG. 3 of the present invention to enable the system, method, and objective of the invention shown in FIGS. 1, 2, 3, 25, and 26.

FIGS. 9a-9c provide example diagrams of panoramic imagery and brain activity imagery representing the same subject matter that may be logged by a user/recipient and/or 2/5, 6, 7 as a subscriber 20 into the computer system 113, 155, 165, 169 or 198 who is bearing the present invention 6, 7, 113, 155, 165, 169. FIG. 9a provides a diagrammatic representation of the front view of a composite frame 179 of panoramic camera with two back-to-back fisheye lenses to render a Side A 179 and Side B 179 b undistorted 360-degree photo or video image. Each 360-degree image 179 is taken starting at Time 1 (T1) 187 and includes subsequent images T1 to the nth 184 starting at a given location(s) to the nth in the panoramic spherical field-of-view (FOV). The subject matter in the imagery captured by the panoramic camera corresponds to neural activity in FIGS. 8a-b, and FIGS. 9b-c related to a conscious percept. For example, in FIG. 9a the camera records a surrounding panoramic scene that is cor-related with brain activity to identify NCC's that represents the word "dog" 183 that corresponds to a CP. A black dashed line 185 represents where side A and side B images are stitched together either optically or by image processing in the associated computer system 165 or an associated remote computer system 42. FIG. 9b is a diagrammatic represen-tation of fMRI brain imagery 188 representing subject matter that correlates with the panoramic imagery shown in FIG. 9a and brain imagery in FIGS. 8a-8b taken at the same time T and place P number one #1. FIG. 9c is a diagrammatic representation of voxel brain imagery 189 representing subject matter that correlates with the panoramic imagery shown in FIG. 9a and brain imagery in FIGS. 8a-8b taken at the same time T and place P number one #1. In FIG. 9c is a diagrammatic representation of voxel brain imagery representing subject matter that may be logged into the host computer system that correlates with panoramic imagery shown in FIG. 9a. High resolution voxel generation like that by Openwater™ imaging system to identify specific neurons may be incorporated in full by reference into the instant invention to derive conscious perceptions (CPs) and Neural Correlates of Consciousness. For example, FIGS. 9b and 9c illustrate synapse 163 connections which connect to at least one neuron 164 may be imaged and operated upon by a computer to identify NCC's that represents the word "dog" 180 that correspond to a CP. In FIG. 8a-9c imagery, and data and information derived therefrom may be stored and oper-ated upon in the associated computer system 165 or an associated remote computer system 42.

Figure 10A:
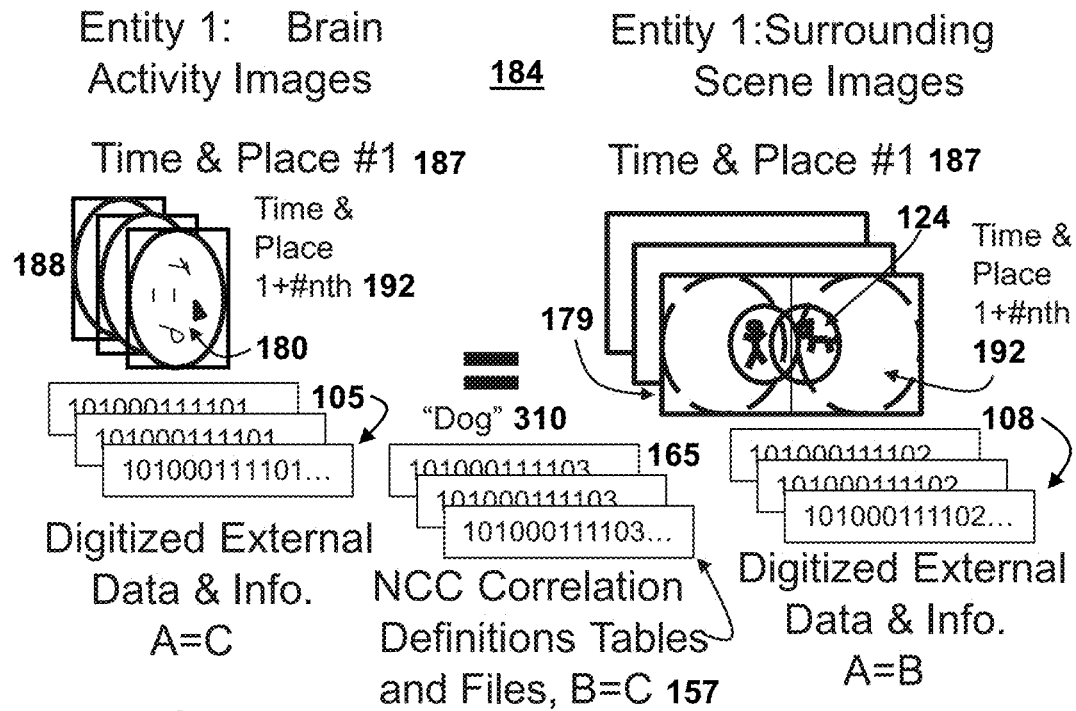
FIG. 10a is a diagram illustrating the method of constructing a computer database of neural correlation tables derived from internal and external sensor data recorded from and about a being, machine, or bio-mechanical system in the present invention by operating a computerized correlation system.
Figure 10B:
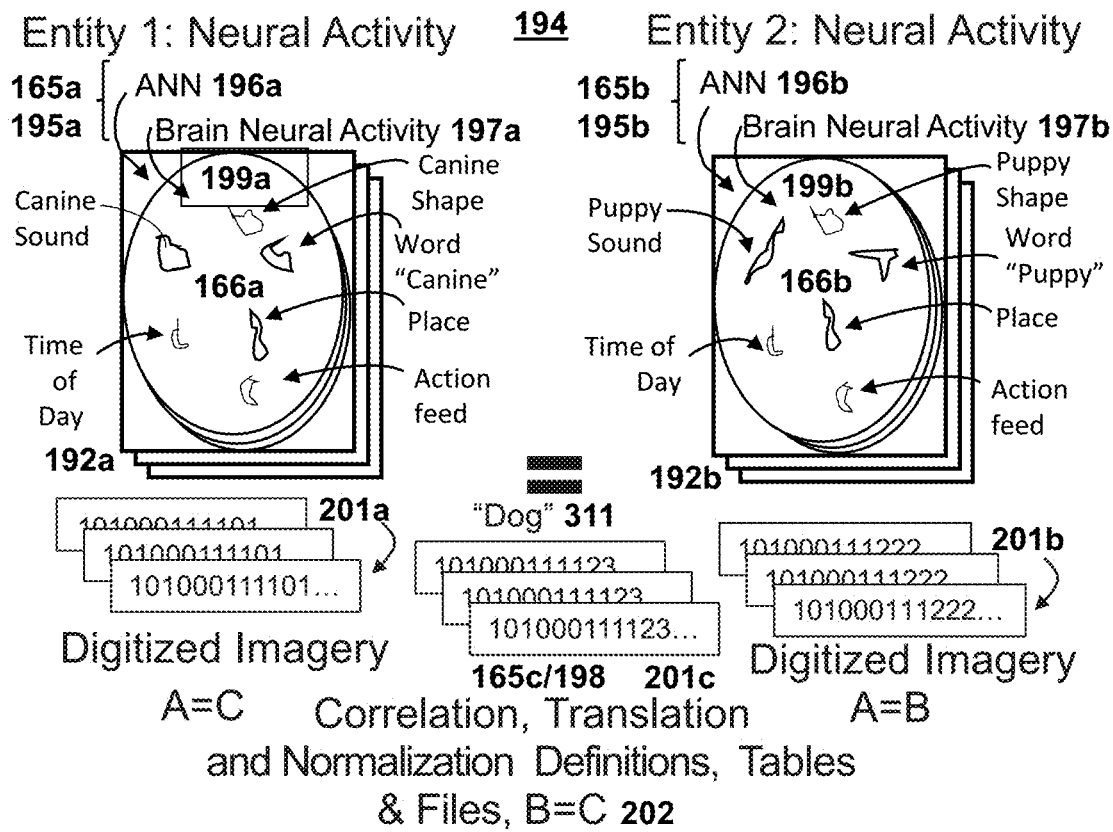
FIG. 10b is a diagram illustrating computer normalization of common relationships of brain activity sensor, CP, and NCC data derived from two different beings in order to construct at least one translation table that form at least one computer database to facilitate communication between two different beings, machines, or bio-mechanical systems.

As Illustrated in FIGS. 10a and 10b, computer correla-tions engines can use artificial neural networks to search out image and signal patterns in a powerful and quick manner to find correlations among the panoramic images and neural images in order to derive Neural Correlations of Conscious-ness (NCC) in the present invention. And that once these relationships are derived a digital relational database of the parent person's NCC's database in the form of machine languages can be stored or be further processed by a computer. And that the relational NCC's database into that is generated may be operated by a PDA or recipient human-like bio-mechanical and mechanical entity/system in accor-dance with the enterprise system of the present invention in order to emulate a parent being or evolve a recipient biological, bio-mechatronic and mechatronic entity's artifi-cial NCC's computer database. For instance, a biological augmented reality system may operate on a NCC database to derive and present information to a human wearing a HMD. Or a synaptic chip, nanobot 298 may operate on a NCC database to derive and present information into the brain of a biological or bio-mechatronic entity. And finally, input of the NCC database may be operated upon by a human-like mechatronic 7 entity, such as a robot or PDA device with A. I., to interact with another person, robot, or PDA device.

Still referring to FIGS. 10a and 10b, once a subject or an action has been identified as the CP the neural activity of a user, 5, 6, and or 7, the NCC's for that subject matter or activity may be constructed as a correlation table 308, algorithm 309, or the like as part of the NCC database in the computer 165. The CP NCC database defines various sensor signatures that mean the same subject or activity between internal neural activity and external surrounding environ-ment activity recorded as sensor system data and informa-tion which comprise the NCC correlation definitions, tables, and files, B=C 184 in FIG. 10a, or the correlation, transla-tion, normalization tables, definitions, and files, B=C 194 in FIG. 10b respectively. The subjects and activities logged can be expressed by a word or words groups, numbers or number groups, or an image or groups of images in whatever language is compatible to the user, be it a cognitive being or machine. The biological 5, bio-mechatronic 6, or mecha-tronic 7 being processes and operates on the CP NCC database with a natural or artificial neural network, or a combination thereof to achieve actions. The rectangular boxes in FIGS. 10a-10c with numbers graphically indicate computer code derived by operating system 165 which receives and processes the result of user one's neural activity at a given Time and Place 187 that has the CP that defines the NCC that perceives a "dog" 154, 180, 124. The computer code 105 represents recipients's neural activity 180 at a Time and Place 187. The computer code 108 represents entity ones surrounding environment 161 at a Time and Place 187. Computer code 157 represents the definition of the NCC correlation derived by the correlation engine of computer 165 at Time and Place one 187. In FIG. 10b this relationship is expressed as entity one's neural activity A defines the NCC as "canine" C, and user two's neural activity A defines the NCC as "puppy" B given a certain time an place 192a-192b. The computer 165 normalizes entity one and entity two's NCC's neural activity and imagery using A.I. LLEMA information is used to derive a common taxonomy that results in B equal to C. Such that both entities agree that the similarities define a common subject that is a "dog". In summary, in FIG. 10a the result of the neural activity and imagery sensed, recorded, and processed by computer 165 borne by the entity one results in an NCC that defines a "dog" 310, and in FIG. 10b the neural activity sensed, recorded, and processed by entity one and entity two is normalized by computer 165 and results in a common taxonomy that defines a "dog" 124 represented in the panoramic image 179. Such that the same subject is corre-lated and at least one translated and/or normalized to be "dog" 311 by at least one system 165 borne by of the biological entity(s) 5, bio-mechatronic entity(s) 6, or mecha-tronic entity(s) 7 to facilitate communication between enti-ty's one and entity two. In the present example, the oval represents a natural biological brain, and the rectangular box 188 around the oval represents computer system 165 that is borne by and assists the entity 6 (i.e., LLEMA). For example, In FIG. 10b both bio-mechanical entity 6 one and entity two are designed to operate on natural human neural activity 197a-197b and/or machine data using artificial neural networks (ANN) 196a-196b to derive a result 202, 201c, 311 by correlating, translating, and normalizing information sensed, recorded, and processed by computer system 165a and 165b processed as bio-mechanical neural activity 195a-b. Entity computer processing of biological neurons spiking and firing in in the brains of entity one and entity is designated by 199a and 199b respectively. Entity correlation, translation, normalization processing by and between entity one and entity two is designated in numbered boxes 201a and 201b with the shared result derive by systems 165a and 165b illustrated in box 201c. Entity 7 uses NCC and related data gathered by a parent entity 6 for input into it's memory but does not require the biological sensing system to operate as a self-reliant recipient entity. Related data gathered by a parent entity 6 or 7 may be introduced in a non-intrusive or intrusive manner into biological recipient 5. And biological recipient 5 may still operate as an independent biological being without use of system 165 after parent entity 6 or 7 information is introduced if no implant or wearable remains in biological recipient 5. An embodiment of the current invention is that at least one correlation, translation, and normalization, and results that drive entity action processing and command and control of the entity computers 165a and 165b may be passed off to a local or remote computer 165c/198.

Still referring to FIGS. 10a-10b, the computer 165 database preferably comprises a database with meta tags and metadata to locate other data in a search engine that performs translation correlations between persons or machines as they communicate. Databases like those in the CALO and neural network system previously described in related art may be incorporated to assist in translation between users. Typically, the correlation tables and algorithms will comprise look-up tables in the computer which relate user neural correlates to logged video. The translation key equates human brain activity patterns to images and audio, with words that are formed by the computer 165 and/or remote computer 198 server system operating upon look-up LLEMA data in the computer 165 and/or remote computer 198 server system that equate to similar representations, such as words or images. Various normalization, correlation systems, correlation tables, and translation keys are widely known and used in the computer industry so will not be described in any more detail in this specification. Various search normalization, correlation, transcription, and translations systems are be used in embodiments of the present invention. Because the brain is a dynamic organ, updates of the correlation tables will be programmed into and accomplished by host computer system 165 and/or remote host computer 198 server system. For instance, language may also be composed of any suitable computer language such as C++ or synthesized natural language that facilitates communication between entities.

The present invention accomodates using either or both unstructured and structured learning. An unstructured approach for a person or a machine with artificial intelligence is to learn by observing the world and trying things. Humans naturally build intelligence and motor skills from the-ground-up by learning as they mature and grow from baby to adult. Humans typically develop perceptions by doing things repeatedly and unstructured artificial intelligence uses the same approach. The present invention captures the intelligence and motor skills that human's naturally build and mimics it in devices like PDA's 95-99 and entities 5, 6, 7 in accordance with the present invention. By learning via video camera imagery and audio subject in an environment may be recorded and the user' internal and external A.I. processing by the host computer system 165 and/or remote host computer 198 server system that incorporate artificial and artificial-like intelligent processing systems to predict the user's/recipient's conscious perception and his or her neural correlates of consciousness. However, prediction by outward observation of a user's surrounding and of the user is more speculative (circumstantial) than using a brain activity sensing system and correlating it to a conscious perception to build a NCC database that is specific and personal to the parent individual or the internal workings of a recipient entity being mimicked. In constructing a human like robot the goal is not only to mimic a certain person's personality, actions, and perceptions, but in some embodiments to also provide the biological 5, bio-mechanical 6, or mechanical entity 7 with the free will the parent being naturally had as a human being 2. Thus, a combination of first mimicking what is there by recording the persons existing knowledge as a basis for the recipient entity's perceptions is a key feature in mimicking a given person in the form of a biological recipient 5, bio-mechatronic 6 or mechatronic entity 7. Of course, PDA's devices without natural brains do not need some components like brain activity sensor systems, but may link to brain activity sensors and use or process their output or derived NCC databases to update and operate upon. Additionally, in some applications of the present invention PDAs may be stationary and not need to be portable, other than being moved about in a room, but not necessarily worn. The exception being use of a PDA on or in a mobile vehicle, in which case the PDA has a portable power source. PDA devices and entities described in the present invention all communicates with host computer via cable circuitry or a wireless connection. The host computer may be of a conventional portable design which is frequently implemented in portable laptops, personal digital assistants, cell phones, and the like. The host computer includes hardware and software and/or firmware.

Components are connected by a system bus and/or electrical bus 172 and include, but are not limited to, input/output jacks, a portable power system with a battery, interactive input devices, video card, hard drive for storing data, random access memory for storing volatile data, central processing systems, cooling fans, telecommunications system, and the like. Additionally, the host computer includes either software (written programs or procedures or rules and associated documentation pertaining to the operation of a computer system and that are stored in read/write memory) and/or firmware (coded instructions that are stored permanently in read-only memory). A computer system and software of a type compatible and incorporated in the present invention is that disclosed in Ritchey et. al. Related Applications cited at the first of the application, in U.S. Patent 2009/0196493, dated 6 Aug. 2009; by Widrow et al. entitled "Cognitive Method and Auto Associative Neural Network Based Search Engine for Computer and Network Located Images and Photographs"; Cognitive Agent that Learns and Organizes (CALO) Software; and U.S. Patent Application 20070124292 A1, by Kirshenbaum et al., dated 31 May 2007, entitled "Autobiographical and Other Data Collection System"; and the Ultra-Vis, Leader system developed by ARA, subsidiaries MWD, Vertek, and KAD, and other companies to include Lockheed Martin and Microvision Incorporated™ which teach a stereoscopic video logging system with querying. Thus, the host computer includes an operating system (OS), a brain activity sensing system that can detect neural activity at the molecular level, dynamic image and brain pattern activity translator and comparator, head-mounted display system (including head and eye-tracking and optionally global positioning system), voice recognition system (and optionally sub-vocalization system 208), panoramic video system, optional telecommunication system, and memory enhancement and personal assistant that learns software and firmware. While preferable to use a single computer language for efficiency, it will be obvious to those skilled in electronics and computer science that a computer program that converts a program from one language to another to link software written in a different language and machines written to run on different software together is common and may be incorporated to enable the current invention if necessary. In this manner the above referenced software may be linked together to form a single system in the present invention. This translation software may be implemented at the assembly language level as a low-level programming language for computers, microprocessors, microcontrollers, and other integrated circuits; and/or as a utility program called an assembler used to translate assembly language statements into the target computer's machine code.

Brain inspired computer processing systems ideally suited for adaption with the current PDA and recipient and entity embodiments described in the present invention and adopted by reference in full include the following: A system developed by Lichao Chen et al. (Lichao Chen, Sudhir Singh, of the Department of Electrical and Computer Engineering, University of California, Los Angeles, Calif. 90095; Thomas Kailath, and Vwani Roychowdhury of the Department of Electrical Engineering, Stanford University, Stanford, Calif. 94305) entitled "Brain-inspired automated visual object discovery and detection", published online Dec. 17, 2018, at www.pnas.org/cgi/doi/10.0173/pnas. 1802103115, b.) and "Supporting Information Appendix: Brain-Inspired Automated Visual Object Discovery and Detection to the same paper which is adopted in full by reference as a type of processing compatible for use in the present invention. The software applications and efficient algorithms of the system run on an Apple desktop computer system but may be scaled down to VLSI and MEM processors. The design of unsupervised, scalable, and accurate computer vision (CV) systems, inspired by principles gleaned from biological visual-processing systems. Recent success of the Deep Neural Network (DNN) 57 framework has largely been attributed to its brain-inspired architecture, comprised of layered and locally connected neuron-like computing nodes that mimic the organization of the visual cortex. The features that a DNN automatically discovers are considered to be its primary advantage and which outperforms more conventional classifiers driven by hand-crafted features [such as scale-invariant feature transform (SIFT) and histogram of oriented gradients. Replication of such capabilities in a machine would require three key ingredients: (i) access to large-scale perceptual data of the kind that humans experience, (ii) flexible representations of objects, and (iii) an efficient unsupervised learning algorithm. The leverages the availability of such data to develop a scalable framework for unsupervised learning of object prototypes—brain-inspired flexible, scale, and shift invariant representations of deformable objects (e.g., humans, motorcycles, cars, airplanes) comprised of parts, their different configurations and views, and their spatial relationships. Computationally, the object prototypes are represented as geometric associative networks using probabilistic constructs. The system has a framework compatible with various datasets and is computationally scalable and can construct accurate and operational part-aware object models much more efficiently than in much of the recent computer vision literature. We also present efficient algorithms for detection and localization in new scenes of objects and their partial views In the present application computer system and application software Lichao Chen et al. is well suited and incorporated into the present invention by reference in full because it mimics human visualization which host computer system 165 and/or remote host computer server 198 with artificial and artificial-like intelligent processing systems may incorporate to predict the user's/recipients conscious perception and his or her neural correlates of consciousness incorporate which drive PDA 95-99 and Entity 5, 6, 7 command and control in the present invention. And when other sensor information is added in from various other sensor modalities and includes a NCC structured historical relational database to start from provides an especially strong Artificial Intelligence (A.I.) system that mimic human thought and artificial action potentials in PDA devices and human-like entity systems. Another compatible processing system known as "Whetstone" adopted by reference in full that may be used to enable present invention that is of a type for operating the PDA devices and human-like entity systems of the present invention is a Sandia National Laboratories' memristor that can cross-train standard convolutional neural networks (CNN) to a spiking neural model that can be used on neuromorphic processors that mimic the way biological neurons work described in the Mar. 5, 2019 article by Michael Feldman, et al entitled "One step closer to deep learning on neuromorphic hardware" at the THENEXT-PLATFORM.com.

As discussed in the preceding paragraphs the goal of maintaining and transitioning humans 2 to a supplementary adaptable sentient human-like self-reliant entity 5, 6, 7 when linked with the enterprise 1 architectures 16 is accomplished in of the present invention. This is accomplished by first deriving a semi-structured database of the person to be mimicked and then on top of that providing an unstructured machine learning capability to let the human-like bio-mechanical or mechanical entity evolve their perceptions, just like a normal human being does. As seen in FIGS. 3, 6, 7, and 25, the goal of maintaining and transitioning humans to a supplementary adaptable sentient human-like self-reliant entity approach represents the moral imperative that is organically integrated and reflected in the science, technology, and business side of the Enterprise 1 Architectures 16 of the present invention. Both external and internal sensing systems with different sensory modalities are used in the present invention used to increase the fidelity in identifying the conscious precept and neural correlates of consciousness via the Life Logging & Enhancement Memory Assistant System 155 that constitutes host computer system 165 and/or remote host computer 198 server with at least one artificial and artificial-like intelligent processing systems that process information that constitutes the relational database 100 that is operated upon to control PDA 95-99 and entities 5, 6, 7.

Brain imaging systems are a subset of brain activity sensing systems. "Related Patents" cited at the beginning of this application and the present invention that operate on brain activity sensing systems such as brain imaging systems are compatible with the present invention are adopted in full by reference into the previous parent, child, and present invention. For example, U.S. Pat. No. 9,730,649 by Mary Lou Jepsen issued Aug. 15, 2016 and filed as application number U.S. Ser. No. 15/264,088 on Sep. 13, 2016 entitled "Optical Imaging of diffuse medium"; which are assigned to Openwater™ Incorporated which describe systems and methods for a display pixel array that is illuminated by infrared light in a frequency band. An infrared holographic imaging signal is generated by driving a holographic pattern onto the display pixel array. And an image of an exit signal of the holographic infrared imaging signal being captured with an image pixel array. The image pixel array is configured to capture the infrared light and reject light outside the frequency band. And which describe methods and apparatus are configured for focusing and imaging of translucent materials with decreased size and complicity and improve resolution. The methods and apparatus provide improved focusing and imaging with decreased size and weight, to allow use in many fields.

The Openwater™ systems are portable typically worn as non-invasive medical imaging devices, with high resolution and low costs that enable universal access to medical diagnoses and treatments for body and brain. The Openwater™ brain activity system and method incorporates optoelectronic devices, such as red light, near-infrared imaging (fNIR), focused ultrasound, holographic systems, and novel lasers that enable Openwater™ to rival the depth, resolution, and image quality of multi-million dollar medical imaging scanners like MRI, CT and PET. In operation in the present invention the brain activity sensing system data and information on neural activity (i.e., time and spatial location in the brain) is communicated from the Openwater™ system to the Ritchey et. al. host computer system 165 and/or remote host computer 198 server with artificial and artificial-like intelligent processing systems may incorporate to predict the user's/recipients conscious perception and his or her neural correlates of consciousness incorporate which drive PDA 95-99 and Entity 5, 6, 7 command and control in the present invention. Ritchey's computer system processes that information with surrounding imagery derived from a head mounted (HM) video camera that records video of the user's conscious percept (CP) to derive a NCC database as described in accordance with Related Art referenced at the start of this Specification and subject matter claimed unique to the instant CIP application. The sensed brain imagery and data from Open Water's brain activity sensing system imagery and associated data is correlated with the surrounding environment data sensed in the present invention Ritchey et al Related Patents to draw relationships on the perceptions of the user wearing the mobile Openwater™ system that is positioned within, about, or a combination thereto the user's head. In operation in the present invention the brain activity sensing system data and information is communicated from the Openwater™ system to the present invention by operating electronic devices with communication apparatus in a communicative relationship with the present invention. The sensed brain data from at least one a recipient 5 or 6 brain 139 originating from the Openwater™ system is correlated with the surrounding environment data sensed in the present invention to draw relationships on the perceptions of the user wearing the mobile Openwater™ system that is positioned within, about, or a combination thereto the user's head. For example, in the Openwater™ system in the present invention an fNIR imaging signal is generated and focused into the brain, an image of an exit signal of the infrared imaging signal is captured, and the change in the infrared imaging signal within a frequency band exiting the brain is captured and processed by a computer to determine the brain activity at a given location. The baseline inactivity signature in brain activity at Time 1 versus Time 2 when a change in activity is captured and correlated with the activity when different conscious percepts (CPs) are focused upon by the user to build a neural correlates of consciousness (NCC) database. in the present invention. Additionally, Openwater™ brain activity imagery sensed and corresponding image signal coded into machine language may be translated into a NCC database that may be translated into a visual image for display consistent with the imagery of the imagery seen in the real world by the person from whom the brain image the brain activity imagery sensed and signatures where derived.

Brain activity sensing system 103, 177 and methods and related devices of a type that Openwater™ incorporates and of a type compatible within the present invention that are adopted by reference in their entireties for use into the present application include: U.S. Pat. No. 9,989,765B2 Mary Lou Jepsen Oculus Vr, Llc, Priority 2015 Aug. 3 Filing 2016 Mar. 9 Grant 2018 Jun. 5 Publication 2018 Jun. 5, entitled "Tile array for near-ocular display"; WO US CN U.S. Pat. No. 9,730,649B1 Mary Lou Jepsen Open Water Internet Inc., Priority 2016 Sep. 13 Filing 2016 Sep. 13 Grant 2017 Aug. 15 Publication 2017 Aug. 15, Optical imaging of diffuse medium; U.S. Pat. No. 9,935,395B1 David Lee Jepsen Cadwell Laboratories, Inc.; Priority 2017 Jan. 23 Filing 2017 Jan. 23 Grant 2018 Apr. 3 Publication 2018 Apr. 3; "Mass connection plate for electrical connectors"; US US20190072897A1 Mary Lou Jepsen Open Water, Inc., Priority 2017 Aug. 14 Filing 2018 Aug. 7 Publication 2019 Mar. 7, "Applications of diffuse medium imaging"; US U.S. Ser. No. 10/297,180B2 Jianru Shi Facebook Technologies, Llc, Priority 2015 Aug. 3 Filing 2016 Nov. 9 Grant 2019 May 21 Publication 2019 May 21, "Compensation of chromatic dispersion in a tunable beam steering device for . . . "; US US20170115519A1 Jianru Shi Oculus Vr, Llc, Priority 2015 Aug. 3 Filing 2016 Nov. 9 Publication 2017 Apr. 27, "Time-Domain Adjustment of Phase Retardation in a Liquid Crystal Grating for a . . . "; Publication 2010 Jun. 29, "Dual mode display"; WO US CN JP KR GB TW US20100225640A1 Carlin J. Vieri, Priority 2009 Mar. 3 Filing 2009 Dec. 1 Publication 2010 Sep. 9, "Switching Operating Modes of Liquid Crystal Displays"; U.S. Pat. No. 6,172,792B1 Mary Lou Jepsen Mary Lou Jepsen Priority 1997 Jan. 31 Filing 1998 Jan. 30 Grant 2001 Jan. 9 Publication 2001 Jan. 9, "Method and apparatus for forming optical gratings"; US U.S. Ser. No. 10/274,730B2 Mary Lou Jepsen Facebook Technologies, Llc, Priority 2015 Aug. 3 Filing 2016 Mar. 9 Grant 2019 Apr. 30 Publication 2019 Apr. 30, "Display with an embedded eye tracker"; WO US CN TW U.S. Pat. No. 9,123,266B2 Behnam Bastani Google Inc., Priority 2013 Nov. 19 Filing 2013 Nov. 19 Grant 2015 Sep. 1 Publication 2015 Sep. 1, "Seamless tileable display with peripheral magnification"; WO US TW U.S. Pat. No. 9,558,720B2 Mary Lou Jepsen X Development Llc, Priority 2013 Oct. 7 Filing 2016 May 4 Grant 2017 Jan. 31 Publication 2017 Jan. 31, "Variable resolution seamless tileable display"; WO US JP KR TW U.S. Pat. No. 8,384,861B2 Mary Lou Jepsen Pixel Qi Corporation, Priority 2008 Jul. 28 Filing 2009 Jul. 28 Grant 2013 Feb. 26 Publication 2013 Feb. 26, "Diffractive liquid crystal display"; WO EP US CN TW U.S. Pat. No. 9,841,624B2 Mary Lou Jepsen X Development Llc, Priority 2013 Jul. 19 Filing 2017 Apr. 12 Grant 2017 Dec. 12 Publication 2017 Dec. 12, "Configurations for tileable display apparatus with multiple pixel arrays"; WO EP US CN TW U.S. Pat. No. 9,841,624B2 Mary Lou Jepsen X Development Llc, Priority 2013 Jul. 19 Filing 2017 Apr. 12 Grant 2017 Dec. 12 Publication 2017 Dec. 12, "Configurations for tileable display apparatus with multiple pixel arrays"; WO US CN JP KR TW US20100020054A1 Mary Lou Jepsen Pixel Qi Corporation, Priority 2008 Jul. 28 Filing 2009 Jul. 28 Publication 2010

Jan. 28, "Triple mode liquid crystal display"; WO US TW U.S. Pat. No. 8,264,646B2 Mary Lou Jepsen Pixel Qi Corporation, Priority 2008 Jul. 28 Filing 2009 Jul. 28 Grant 2012 Sep. 11 Publication 2012 Sep. 11; "Transflective display with white tuning"; WO US TW U.S. Pat. No. 9,412,336B2 Behnam Bastani Google Inc.; Priority 2013 Oct. 7 Filing 2013 Oct. 7 Grant 2016 Aug. 9 Publication 2016 Aug. 9, "Dynamic backlight control for spatially independent display regions"; JP KR TW Publication 2014 May 11, "Self-refreshing display controller for display devices in a computational unit"; WO US CN KR TW; Priority 2006 Mar. 23 Filing 2007 Mar. 23 Grant 2014 May 11 Publication 2014 May 11, "Self-refreshing display controller for display devices in a computational unit"; WO US CN KR TW. US20180335753A1 Mary Lou Jepsen Open Water Internet Inc.; Priority 2017 May 22 Filing 2018 May 19 Publication 2018 Nov. 22, "Co-located Imaging and Display Pixel"; (red) WO US CN U.S. Pat. No. 9,730,649B1 Mary Lou Jepsen Open Water Internet Inc.; Priority 2016 Sep. 13 Filing 2016 Sep. 13 Grant 2017 Aug. 15 Publication 2017 Aug. 15; "Optical imaging of diffuse medium"; WO US CN KR TW U.S. Pat. No. 9,803,833B2 Mary Lou Jepsen X Development Llc Priority 2013 Dec. 3 Filing 2013 Dec. 3 Grant 2017 Oct. 31 Publication 2017 Oct. 31, "Multi-aperture illumination layer for tileable display"; U.S. Pat. No. 9,626,145B1 Belle Fu X Development Llc Priority 2014 Jun. 27 Filing 2014 Jun. 27 Grant 2017 Apr. 18 Publication 2017 Apr. 18; "Tileable display with pixel-tape"; US20190072897A1 Mary Lou Jepsen Open Water, Inc., Priority 2017 Aug. 14 Filing 2018 Aug. 7 Publication 2019 Mar. 7, "Applications of diffuse medium imaging", (i.e., infrared) WO US CN US20180070891A1 Mary Lou Jepsen Open Water Internet Inc. Priority 2016 Sep. 13 Filing 2017 Jul. 26 Publication 2018 Mar. 15, "Imaging with Infrared Imaging Signals"; WO EP US CN TW U.S. Pat. No. 9,841,624B2 Mary Lou Jepsen X Development LLC Priority 2013 Jul. 19 Filing 2017 Apr. 12 Grant 2017 Dec. 12 Publication 2017 Dec. 12, "Configurations for tileable display apparatus with multiple pixel arrays"; US US20180335753A1 Mary Lou Jepsen Open Water Internet Inc., Priority 2017 May 22 Filing 2018 May 19 Publication 2018 Nov. 22, "Co-located Imaging and Display Pixel"; US20190072897A1 Mary Lou Jepsen Open Water, Inc.

The below types of technologies referred in the present system as brain activity sensing systems and brain signal monitoring systems in the present invention are broadly classified into non-invasive (EEG, MEG, MRI) and invasive (Microelectrode, ECoG, MEA, and implantable nanobots, MEMS, and synaptic chips). It is an object of the present invention to address the challenges to resolve neuronal damage, usability, and comfort relative to the present invention. The human brain consists of approximately 100 billion of neurons 164 that communicate information through electro-chemical action potential, which is and endogenic bioelectric phenomenon, and communications between synapses 163 as increased connectivity through induced processes. Each individual neuron 164 can form thousands of links with other neurons in this way, giving a typical brain well over 100 trillion synapses by some estimates. Ref. "The Cogs Are Coming: The Cognitive Augmentation Revolution", by Ron Fulbright, University of South Carolina, 2015 ASCUE Proceedings.

Brain connectivity systems can be categorized into three types: Neuroanatomical connectivity that is based on structures of synapses, Functional connectivity that has statistically significant dependence, and effective connectivity that is dynamic directional interactions among brain regions. An Action potential of a single unit (neuron) has an electrical discharge characteristic that can be recorded by intracellular electrodes. Activities of a collection of neurons at a proximal location can be recorded through extracellular electrodes as local field potential (LFP) or as neural firing. LFP is recorded by filtering the electrode signals through a low pass filter (1-100 Hz), while the neuron firings are detected through a spike discriminator. Such endogenic electrical activities are recorded through microelectrodes placed inside the brain cortex or at the surface of the brain cortex (invasive). The electrode converts the ionic current of neurons to electronic current, which can be recorded through a high impedance electrical sensing circuit. (REF. "A Brief Review of Brain Signal Monitoring Technologies for BCI Applications: Challenges and Prospects", by Bashir I. Morshed and Abdulhalim Khan, 2014 Bashir I M, et al. Morshed and Khan (2014); and "A Brief Review of Brain Signal Monitoring Technologies for BCI Applications: Challenges and Prospects by J. Bioeng, Biomed Sci 4: 128. doi: 10.4172/2155-9538.1000128, Published Date: May 6, 2014. All of the above and below cited types of brain activity systems 141 cited and referenced in the present invention are hereby incorporated by reference in their entireties into the present application that have been developed to read out brain activity are compatable with the present invention to include MRI, ECoG (or iEEG), Microelectrodes (or Microwire), and MEA systems. The use of current, improved, and new brain activity sensors compatible portable invasive and noninvasive brain activity systems like those provided by various companies and manufacturers cited in the current specification.

For instance, another brain activity sensing system of a type for use as a brain activity sensing system in the current invention by the present inventors includes an invasive brain activity sensing system developed by Elon Musk and the Neuralink™ Corporation. The Neuralink™ systems and methods are adopted in and compatible with and are hereby incorporated by reference in full into the present invention. The Neuralink™ system may act as an integrated brain-machine interface platform with thousands of channels that may functions as a brain activity sensing system and method in the present invention. The Neuralink™ system comprises a Brain-machine Interfaces (BMIs) that holds promise for the restoration of sensory and motor function and the treatment of neurological disorders. Neuralink™ has developed a scalable high-bandwidth BMI system. Neuralink™ has built arrays of small and flexible electrode "threads", with as many as 3,072 electrodes per array distributed across 96 threads. Neuralink™ has also built a neurosurgical robot capable of inserting six threads (xxx electrodes) per minute. Each thread can be individually inserted into the brain with micron precision for avoidance of surface vasculature and targeting specific brain regions. The electrode array is packaged into a small implantable device that contains custom chips for low-power on-board amplification and digitization: the package for 3,072 channels occupies less than (23×18: 5×2 mm×cubed. A single USB-C cable provides full-bandwidth data streaming from the device, recording from all channels simultaneously. This Neuralink™ system has achieved a spiking yield of up to 85:5% in chronically implanted electrodes. Neuralink's™ approach to Brain Machine interface (BMI) has unprecedented packaging density and scalability in a clinically relevant package. (Ref. A white paper by Elon Musk & Neuralink™, entitled 'An Integrated Brain-Machine Interface Platform 166 with Thousands of Channels', 16 Jul. 2019, by Neuralink™ Corporation). In operation in the present invention the brain activity sensing system data and information output from the Neuralink™ brain activity sensing data and signatures information is input into host computer system 165 and/or remote host computer 198 server with artificial and artificial-like intelligent processing systems and incorporated to predict the user's/recipients conscious perception and his or her neural correlates of consciousness incorporate which drive PDA 95-99 and Entity 5, 6, 7 command and control module 137. FIG. 12 includes at least one brain activity processing 199 and artificial neural network 200 processing by the entity system 165 by host computer 113 in entity 6a and 6b. The sensed brain data from the user subscriber's 20 brain from the Neuralink™ system is correlated with the surrounding environment data sensed in the present invention to draw relationships on the perceptions of the user wearing the mobile Neuralink system that is positioned at least one within, about, or a combination thereto the recipient entity 6 head.

Figure 11:
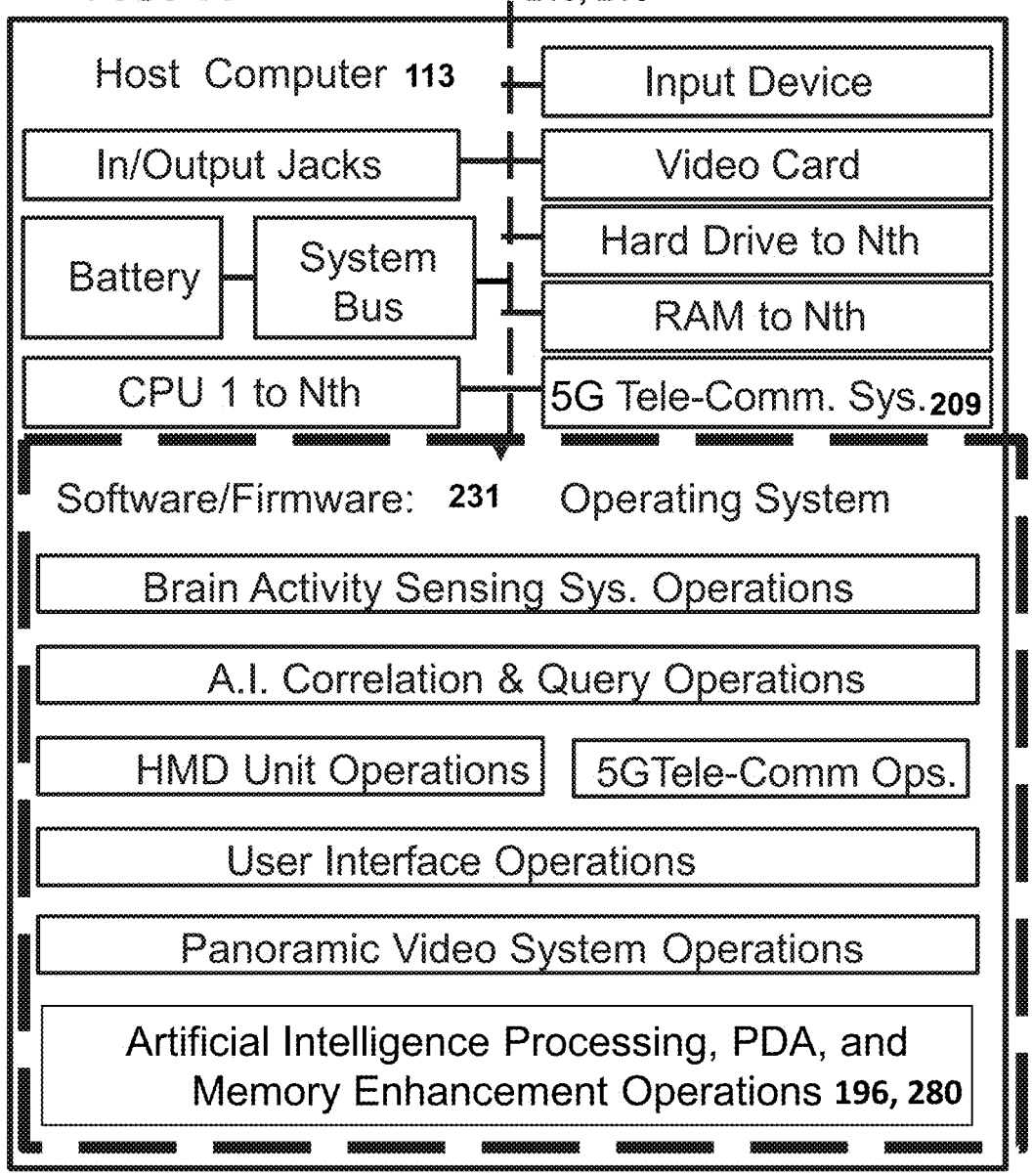
FIG. 11 is a block diagram that names principal system components described in FIG. 12.

Referring now to FIG. 11 and FIG. 12 of the present invention in accordance with Related Art referenced at the start of this Specification that includes new subject matter claimed as uniquely distinct in this instant CIP continuation application.

FIG. 11 illustrates a PDA 97 worn by entity 6a that is a subscriber 20 to the enterprise 1 system and method. FIG. 11 is a block diagram that names principal system components described in FIGS. 11 and 12. FIGS. 11-12 illustrates the components, layout, and interaction of the portable body borne system 165. While any of the types of brain activity sensing systems 103, 169 that have been disclosed or are of a similar type may be incorporated in the present invention, in our present example the internal portion of the head worn system includes brain activity sensor unit 103, 169 comprises an Atomic Magnetometer Resonance (AMR) 228 system with one or more arrays of atomic magnetometer sensors units that detect the relaxation of the magnetic field induced. In the present invention one or more arrays of atomic magnetometers directly detect relaxation of a magnetic field induced with subatomic precession within a target specimen. For instance, the atomic magnetometers sensors units are arranged in a conventional head worn device or helmet wherein the capacity sensors may be used in either a scalar or a vector mode. The AMR may be used to image and provide signal readout on anatomical and non-anatomical structures. In the present example the AMR is used to record the user's brain activity as a wearable, portable array, with low power consumption, incorporating wafer-level fabrication, with rapid signal processing, decreased need for development of strong magnetic fields, and lower cost allowing wider availability. Multiplexing of brain activity signals from the AMR system may be utilized to periodically turn on and off sensors to allow temporal dissipation of magnetic field effects. In the case of atomic magnetometers, the speed of multiplexing can be limited by the relaxation time of the gas in the detection chamber. This relaxation time is typically on the order of microseconds, and is a function of gas composition, pressure, and temperature. Therefore, there is sufficient temporal resolution for applications such as functional imaging. Additionally, shielding may or may not be interposed between specific sensors or sensor pairs to direct magnetic field lines away from adjacent sensors. As a benefit, magnetic shielding (e.g., creating a window of measurability) may augment the direction sensitivity of a given sensor or sensors. Finally, signal processing may be utilized to focus in on or to remove known frequencies related to operation of sensors from measurements. It should be understood, in light of this disclosure, that many other configurations using these concepts are possible. Signal processing algorithms can be utilized to allow localization and deconvolution of distal signals within a target by subtracting more proximal environmental noise. Deconvolution may have the effect of reconstructing a three-dimensional map of the locations and intensities of the signals generated. Because of the relatively small size of the sensors, a relatively high sensor density within a particular array of sensors may be utilized. For example, the sensors may be placed less than 3 mm from the subject's scalp in a closely packed array. Altering the direction of the pump or probe laser may additionally allow increased information at the sensor for the purpose of source localization. Additionally, magnetic shielding may be interposed between the detecting magnetometer and the user specimen to constrain field detection. Shielding may in some cases comprise a disk of mu-metal or other shielding material; other configurations are possible. In some cases, shielding may be rotated to alter directional sensitivity at a given sensor. Various other dynamic shielding strategies may also be used. Various atomic magnetometers with different detection profiles are available and the specific strategy utilized may depend on magnetometer characteristics.

Stacking and grouping of arrays of sensors or arrays of sensor clusters may be utilized to progressively screen signal from noise and to account for spatially uniform sources of noise, or other externally induced magnetic fields. Since atomic magnetometers or similar sensors develop magnetic fields in the course of normal operation (typically related to the direction of light propagation along the sensor), the direction of light propagation among sensors may be alternated, or a random pattern of orientation may be utilized to minimize large scale field effects. In some cases, additional magnetic shielding (such as mu-metal shielding or active shielding) may be placed around a sensor or a cluster of sensors, for the purpose of further mitigating inter-sensor interference, and/or in order to provide a further screen for environmental noise. Since sensor-related magnetic fields typically have a particular magnitude and occur at a particular frequency, signal analysis techniques may be utilized to remove the influence of inter-sensor interference from the information derived from the sensors. While imaging can be performed using a pre-pulse and detection field, other additional features may be used to improve image quality. For example, Louis-Serge Bouchard, and Vasiliki Demas of Berkeley Labs disclosed utilization of pairs of rotating fields through a sample to overcomes image distortions that typically occur when applying conventional NMR detection and MR imaging methods at low fields.

Still referring to FIGS. 11-12, the headgear 97 communicates to the host computer 113 via cable or wireless connection 215 and system bus 216 in each 216 computer 113 and headgear 97. The host computer 113 may be of a conventional portable design which is frequently implemented in a portable laptop, personal digital assistant, smartphone, cell phone, and the like. The host computer includes hardware and at least one software and/or firmware 231 with an operating system (OS) and applications required to achieve the functionality of the disclosed invention. Components are connected by a system bus and electrical bus and include, but are not limited to, input/output jacks, a portable power system with a battery, interactive input devices, video card, hard drive for storing data, random access memory for storing volatile data, central processing systems, cooling fans, telecommunications system, and the like. Additionally, the host computer includes either software (written programs or procedures or rules and associated documentation pertaining to the operation of a computer system and that are stored in read/write memory) and/or firmware (coded instructions that are stored permanently in read-only memory). A computer system and software of a type compatible and incorporated in the present invention is that disclosed in U.S. Patent 2009/0196493, dated 6 Aug. 2009, by Widrow et al. entitled Cognitive Method and Auto-associative Neural Network Based Search Engine 280, 196 for Computer and Network Located Images and Photographs; Cognitive Agent that Learns and Organizes (CALO) Software, and U.S. Patent Application 20070124292 A1, by Kirshenbaum et al., dated 31 May 2007, entitled Autobiographical and Other Data Collection System, and IL is a system compatible with and integrated by reference as art incorporated into the present invention is the Ultra-Vis, Leader, system developed by ARA, subsidiaries MWD, Vertek, and KAD, and other companies to include Lockheed Martin and Microvision Incorporated teaches a stereoscopic video logging system with querying. Thus the host computer includes an operating system (OS), atomic magnetometer system, dynamic image and brain pattern activity translator and comparator, headgear 205 with head mounted display 204 system (including head and eye-tracking 170 and optionally global positioning system, LIDAR, and laser designation system 203) voice recognition system, voice synthesis system, (and optionally sub-vocalization system), panoramic video system, optional telecommunications system, and memory enhancement and personal assistant that learns software and firmware. While preferable to use a single computer language for efficiency, it will be obvious to those skilled in the electronics and computer science that a computer program that converts a program from one language to another to link software written in a different language and machines written to run on different software together is common and may be incorporated to enable the current invention if necessary. In this manner the above referenced software may be linked together to form a single system in the present invention. This translation software may be implemented at the assembly language level as a low-level programming language for computers, microprocessors, microcontrollers, and other integrated circuits; and/or as a utility program called an assembler used to translate assembly language statements into the target computer's machine code.

Referring again to FIGS. 11-12 the focus of the brain activity sensing system 113 will typically and primarily on determining the CP the user is focusing upon in the environment at a given time. But brain activity signatures outside the CP 107 may also be sampled and acted upon. For instance, brain activity neural signatures that stimulate place, grid, and spatial view cells in the hippocampal areas provide visual cues, spatial navigation, and episodic memories of particular locations that could be a general mechanism responsible for the storage and recall of information about a particular set of events which occur together at the same time. Components of the brain activity sensing and stimulation system portion of the headgear in the FIGS. 11-12 may be situated on or in the user's head, scalp, skull, and/or brain, respectively. In the present invention the brain is referred to as one the areas of the internal environment which the system 165 monitors.

Referring again to FIGS. 11-12 the focus of the brain activity sensing system 113 will typically and primarily on determining the CP the user is focusing upon in the environment at a given time. But brain activity signatures outside the CP 107 may also be sampled and acted upon. For instance, brain activity neural signatures that stimulate place, grid, and spatial view cells in the hippocampal areas provide visual cues, spatial navigation, and episodic memories of particular locations in the brain that could be a general mechanism responsible for the storage and recall of information about a particular set of events which occur together at the same time. Components of the brain activity sensing and stimulation system portion of the headgear in FIGS. 11-12 may be situated on or in the user's head, scalp, skull, and/or brain, respectively. In the present invention the brain is referred to as one the areas of the internal environment which the system 165 monitors.

Integrated with the 165 system in FIGS. 11-12 is a panoramic video system 160. Still referring to FIGS. 11-12, the head-mounted assembly 205 worn by the user also includes panoramic audio recording system 212. Headgear 205 comprises audio output systems 212 such as speaker system, such as ear bud audio speakers 138, may provide audio input to the user. Many of the video camera system current video 160 encoding formats carry high fidelity audio. Such audio data can be passed along with a pixel cone data stream PCPDS for an Eye Mounted Display (EMD) 214 such as a contact lens display or separated out within a headpiece. Binaural audio can be brought out via a standard mini headphone or earbud jack, but because the system in many cases will know the orientation of the head (and thus the ears) within the environment, a more sophisticated multi-channel audio to binaural audio conversion could be performed first, perhaps using individual HRTF (head related transfer function) data. Feed-back microphones in the ear buds allow for computation of active noise suppression by the audio portion of the headpiece. The speaker is able to receive input via a radio frequency signal from a remotely located source with audio communication capabilities. Or alternatively may be connected via wires to a unit that provides audio signals for amplification to a small speaker in the ear. Small earphones and ear buds that fit into and onto the ear are known to those in the art and are commonly used in the hand-free cell phone industry and security industry which are of a type that is compatible with and incorporated into the present invention. U.S. Patent 20080056517 by Algazi et al., dated 6 Mar. 2008, entitled Dynamic Binaural Sound Capture and reproduction in focused or Frontal Application that is of a type compatible with and incorporated in the present invention. Algazi discloses a method of tacking head motion and providing directional audio to a headphone or earbud that may be incorporated in the present invention. Still referring to FIGS. 11 and 12, additional sensors that are integrated into the head worn assembly may include a laser rangefinder/target designator and tracking system with image and pattern recognition. A sub-vocalization system may be integrated into the head worn device or may be separately located on or in the user's body and data fed to and from said device into the host computer.

Referring to FIGS. 11 through 24*b*, in operation a support apparatus for recording a surrounding environment comprises a support housing that includes a mounting structure, and sensor assembly to secure the support apparatus on at least one the body of a user, eyeglasses, clothing, prosthetic device, headgear, head mounted display and as a dismounted apparatus. The support apparatus may be optionally designed as a single housing or in modular separate housings. Singularly housed support apparatus components are communicatively connected by the circuitry and separately housed support apparatus components communicatively connected by wireless transceivers or a wireless network. Combined and separated embodiments of the apparatus include an electrical power source. A user borne brain activity sensing subsystem for processing, and transmitting neural activity patterns, activity, and signature data to at least one a PDA 95-99 or entity 5, 6, or 7 host computer 113 subsystem and associated subsystems, components, and peripheral devices for storage with ANN processing that requires a user sensing subsystem configured to collect data corresponding to user events and status and transfer said data to a measurement computer subsystem configured to generate data representing quantifications of perceptions of user activity. And preferably includes at least one biometric device for at least one tracking head and tracking eye position a surrounding environment. The sensing subsystem is configured to collect data corresponding to said user's surrounding environment comprising and preferably comprises a 360-degree field-of-regard audio sensing, recording, processing, transmission, and amplifier subsystem within a surrounding environment integrated with said support housing. The audio subsystem performs audio processing on a captured audio signal and drives power amplification of the audio signal transmitted to a speaker or headphone. The audio being perceptible by a user as the user moves about the environment surrounding the apparatus. Preferably the audio sensor subsystem includes a three-dimensional microphone system with a plurality of small microphones facing outward from the housing that include an acoustical direction system that produces audio signatures. The audio signatures operated upon by the host computer 113 with cognitive memory and artificial neural networks to detect the relative azimuth, range, and elevation, and predict the identity of entities in and nature of the surrounding environment. The PDA or entity in FIG. 11-24 apparatus is operable to play said audio files to replicate the captured three dimensional sound effect by processing the sound and amplification of the sound using at least one of stereo speakers, surround-sound speakers, speaker-arrays, or headphones; a 360-degree field-of-view image sensing, recording, processing, transmission, and display subsystem which captures at least one image signal within the surrounding environment; said image subsystem performing image processing on the captured image signal, and driving the 360-degree field-of-view signal transmitted to the display device facing outward from the periphery and included in said support housing. Still referring to FIGS. 11 through 24*b*, the display preferably includes a user interactive touchscreen in a communicative relationship to a host computer 113, system, such as an electroluminescent display that is constructed of at least one of e-paper, LED, OLED or LCD material that has a side of the display being continuously viewable and interactive with the user as the user moves about the environment surrounding the apparatus and allowing face-to-face interaction between the user and apparatus. Examples of the electroluminescent display 284 that have a 360-degree FOV integrated camera and display as shown in FIGS. 18, 22*c*, 25, 26*c* that incorporate a capability shown in FIGS. 21*a* and 21*b*. The apparatus optionally includes at least one the ability to operate on said imagery to produce at least one monoscopic, binocular, stereoscopic, or holographic imagery for display for at least one the support apparatus or peripheral audio-visual display systems, and optionally includes at least one visual field direction detection software, firmware, or hardware to detect from imagery a user on onlooker's visual field of direction detection from imagery when said apparatus is from worn or dismounted. The apparatus is operable to function as an image processing unit which performs predetermined image processing on the image captured by the 360-degree field-of-view image sensing, recording, processing, transmission, and display subsystem to determine the user or onlooker's visual field direction. And apparatus may optionally include a recording subsystem configured to record said data from a brain activity sensing subsystem, measurement computer subsystem, user sensing subsystem, and surrounding environment sensing subsystem which a host computer 113, 165 subsystem operates upon which has a cognitive memory in a communicating relationship with the 360-degree panoramic audio and image subsystems. The host computing subsystem includes at least one artificial intelligence or an artificial intelligence-like processing system which operates on the recorded 360-degree field-of-regard audio and 360-degree field-of-view image signals to define the physical make-up of the surrounding environment at a given place and time and identify patterns and determining relationships among users, objects, activities, preferences, and agents in the surrounding environment. Furthermore, the host computer subsystem stores those patterns and relationships in a cognitive memory database that defines the surrounding environment at a given place over time and operates to define relationships which the computer stores in nonvolatile memory. The host computer has the capability to operate on said relationships at a later time to assist a user in predicting future outcomes given previous relationships stored in nonvolatile memory. The host computing subsystem with cognitive memory includes an interactive personal assistant application with a smart audio and image display user interface. The smart interface may be operated by at least one the user, host computer, or a remote user or agent to command and control said support apparatus and prompting at least one interactive audio, image, or audio and visual presentation feedback of at least one local, live, stored, and remote content transmitted to the apparatus in order to interact with said user's environment or a remote environment. The user interacts with the support apparatus with 360-degree audio and image field of regard display coverage to accomplish actions with the host computer subsystem. The host computer subsystem includes at least one telecommunications system and network with local area network and internet functionality and compatibility. And the host computer subsystem includes an electrical system and circuitry to provide electricity to power electronic components of the computer and the associated 360-degree audio and image display subsystems. The host computer includes a user mobile electronic device that may be in communication with said brain activity sensing subsystem that includes measurement computer subsystem, audio and image sensing subsystems, surrounding environment sensing subsystem, and recording subsystem, said user mobile electronic device includes an interactive graphic user interface and being configured to: operate as a host computer processing subsystem for command, control, and processing of signals to and from said brain activity sensing subsystem, user sensing subsystem, surrounding environment sensing subsystem, and correlation subsystem. The mobile electronic device may command said brain activity sensing subsystem to transmit brain activity and pattern data to a correlation subsystem and command the user sensing subsystem and surrounding environment sensing subsystem to transmit processed sensor data to said correlation subsystem, said correlation subsystem being configured to receive and perform correlation processing operations to determine an extent of neural relationships between data received from said user mobile electronic device and said brain activity sensing subsystem wherein the user sensing subsystem, and surrounding environment sensing subsystem to derive neural correlates of consciousness of conscious precepts of a PDA or entity. Wherein a correlation subsystem incorporates cognitive memory systems that store input audio, imagery, and user brain patterns representing the user and surrounding environment at a given time and place and retrieving said data without knowledge of where stored when cognitive memory is prompted by a query pattern that is related to a sought stored pattern. At least one the host computer or mobile electronic device may include a retrieval system of cognitive memory wherein an auto-associative artificial intelligence processor with neural network operates using techniques for pre-processing a query pattern to establish relationship between a query pattern and sought stored pattern, to locate sought pattern, and to retrieve best related pattern and ancillary data by connecting cognitive memory to a host computer and personal electronic device 64, like a smart phone 98 or a personal digital assistant 300 to deliver an output response to said query; said stored images interrelated by second means for interrelating to said query hit, and updating old data with new data via back-propagation using an iterative process to learn and improve results over time; and based on results configure and create correlation subsystem data, said correlation subsystem data comprising relationships between said data The correlations may correspond to said brain activity or corresponding to signatures user events, subjects, or the surrounding environment. The host computer system includes system processing devices configured to process and communicate at least a portion of said data from said brain activity sensing subsystem, measurement computer subsystem, user sensing subsystem, surrounding environment sensing subsystems, recording subsystem, and correlation subsystem into at least one of a said support apparatus, user conveyable system, peripheral or remote subsystem, or a recipient biological, bio-mechatronic, or mechatronic system. The host computer is communicatively connected to a provide at least one sensed brain activity data, derived data, and interactive feedback to the user of host computer so the host computer system provides personal assistant applications with an artificial intelligence correlation system that interactively provides panoramic sensing and feedback to at least one the user, host computer, peripheral devices, or a remote user or agent. Preferably, the apparatus with host computer, be it mobile or stationary, includes the capability to transfer onboard processing functions to servers on the internet or another computer on a network. In summary, the apparatus with host computer with cognitive memory and at least one artificial intelligence and artificial-like hardware, firmware or software operates to at least one construct, train, and update an already constructed relational database defining the user and the surrounding environment and in a succeeding dualistic manner in near real-time dynamically operate on said constructed relational database to assist the user in functioning in the local surrounding environment or operate on a remote environment via a telecommunication system and network. Host computer 113 will include a structural system that supports the all components and includes a mobility and dexterity system when the embodiment comprises a self-reliant human-like entity 6, 7 that supports computer system 165. A recipient human being is a biological self-reliant human-like entity 5 embodiment in the present invention cognitively enlightened by information derived from entity 6, 7 and presented to entity 5 through sensory stimulation, like an audio-visual presentation. But when computer 113 is part of PDA 96-99, 300 computer system 113 will not have a structural system like an exoskeleton, or external (i.e., 177) or internal (i.e., 178) headgear that supports a mobility and dexterity system and the advanced cognitive computing system required by a self-reliant human-like entity 6, 7 computer system 165. An exception to this would be a help robot 95, which might have all the same attributes as an entity 6, 7 except for the cognitive computing capabilities that would allow the robot to perform as a self-reliant human-like entity computer system 165. Whereas an entity computer system 165 in the present invention includes a cognitive computing system with at least on software, firmware, and hardware that allows an entity 5, 6, 7 to have at least one intelligence, self-awareness, be conscious, adapt, move around in an environment, and make decisions like a human being.

FIG. 12 is a diagrammatic side view of the host computer system 113 for the PDA system 55-99 system 165 for entity 6 in a backpack cabled to headgear layout of the user born portable video logging with memory enhancement system in accordance with the present invention. Optionally, the entire system is reduced in size and worn as a Head Mounted Display Unit, and includes a 5G telecommunication system and Quantum Safe Encryption enabling components and capabilities as shown in FIG. 3 of the present invention.

Figure 13:
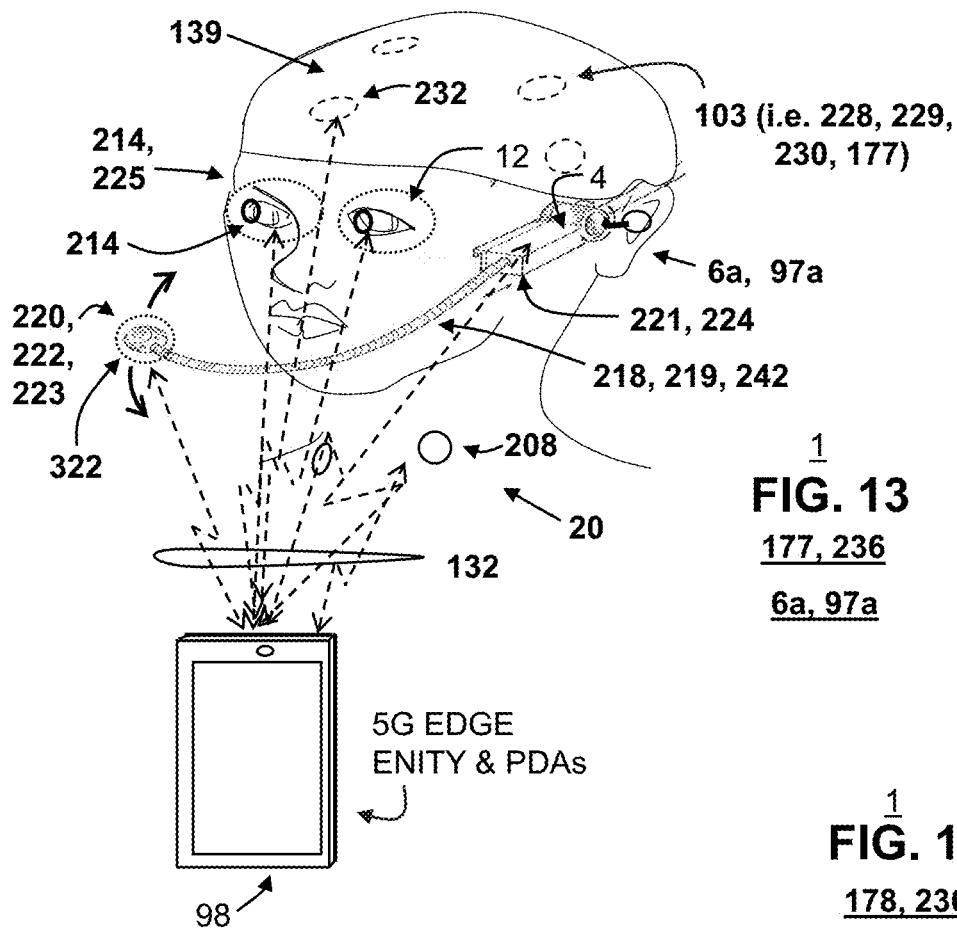
FIG. 13 is an exterior view of the user shown in FIG. 16b wearing a skull cap with a portable brain activity sensing system with inward facing sensors (disguised by a wig in FIG. 16a) and eye mounted displays 214 with non-evasive neural sensing capabilities to interactively operate/drive armature and spherical sensor worn by the user for face-to-face panoramic video teleconferencing in accordance with and supported by the Enterprise Architectures according to the present invention.
Figure 14:
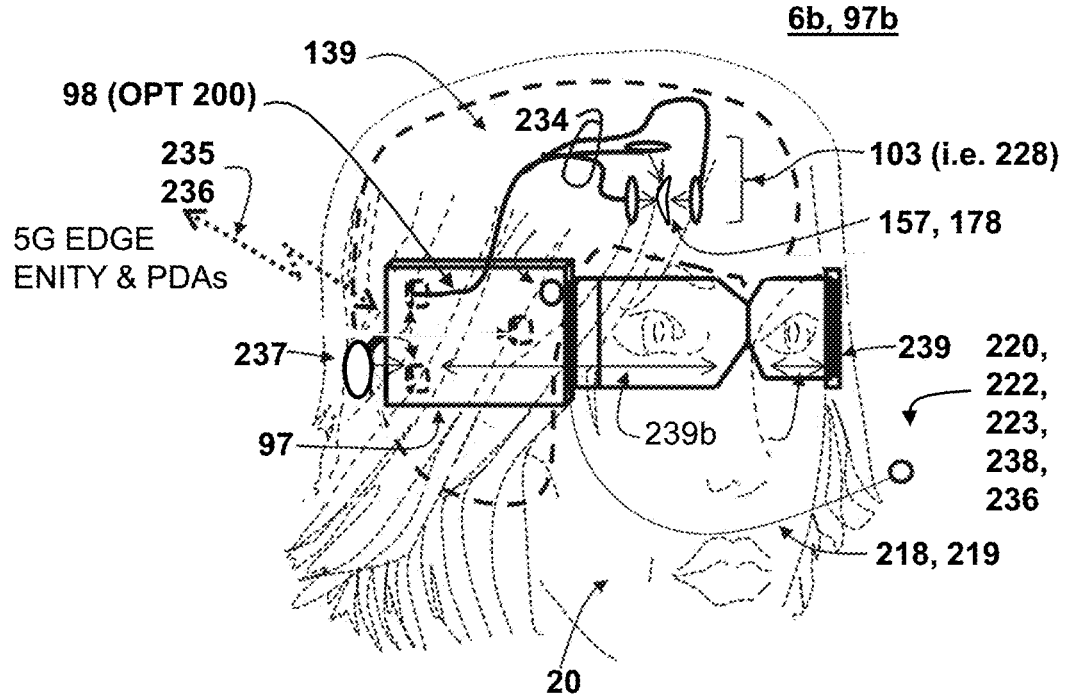
FIG. 14 is a cutaway exterior perspective diagram of a person wearing a head gear which includes a smartphone module with presentation, processing, and input means that connects to implanted invasive brain activity sensor system in accordance with and supported by the Enterprise Architecture according to the present invention.

Referring now to FIG. 13 and FIG. 14. FIG. 13 of the present invention is an exterior perspective diagram of a person wearing a headgear 205 which includes enabling components and capabilities a handheld 5G smartphone 98, processing, and input means that wirelessly connects to the implanted brain activity sensor system 103 and non-interference support apparatus 218 with a panoramic sensor assembly 218, 222, 223 as shown in FIG. 15.

Figure 16A:
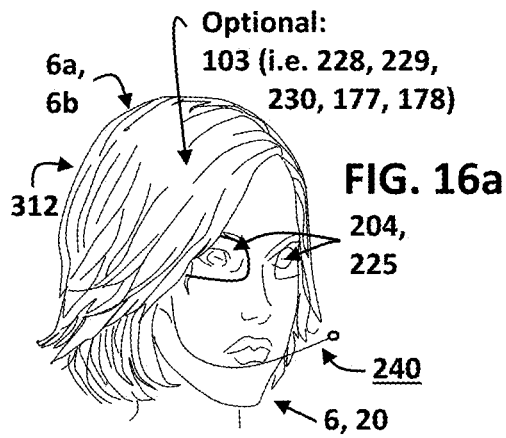
FIG. 16a is an exterior perspective view of a person wearing a wig with head gear which includes non-evasive very small facial sensor assembly with a wireless system comprising a portable electronic device, spherical sensor support, neural sensors, voice recognition sensors, and image sensors used for face-to-face panoramic video teleconferencing in accordance to and supported by the Enterprise Architecture according to the present invention.
Figure 16B:
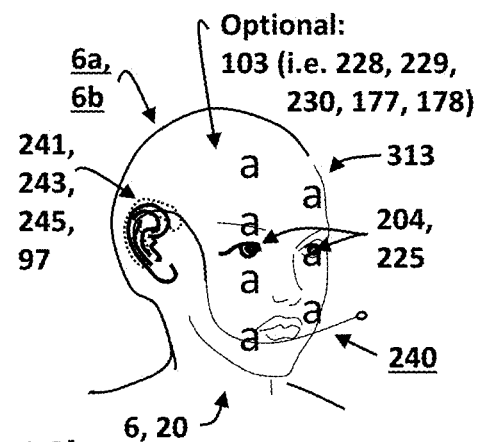
FIG. 16b is an exterior view of the user shown in FIG. 16b wearing a skull cap (disguised by a wig in FIG. 16a) with neural sensing capabilities to interactively operate/drive armature and spherical sensor connected to the user's glasses, over the ear, or wig for face-to-face panoramic video teleconferencing accordance to and supported by the Enterprise Architecture according to the present invention.
Figure 17A:
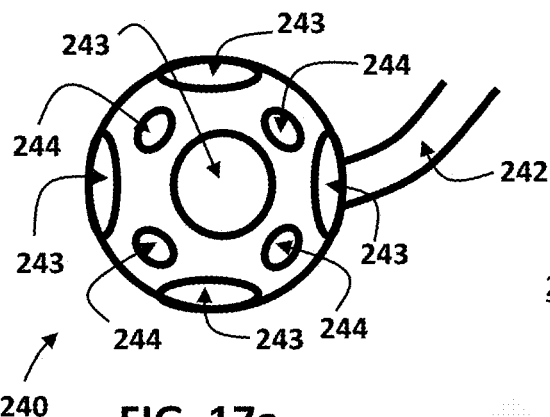
FIG. 17a is a perspective drawing of the exterior of the very small and light weight 3D nano-printed spherical sensor assembly with a plurality of objective lenses and microphones accordance to and supported by the Enterprise Architecture according to the present invention.
Figure 17B:
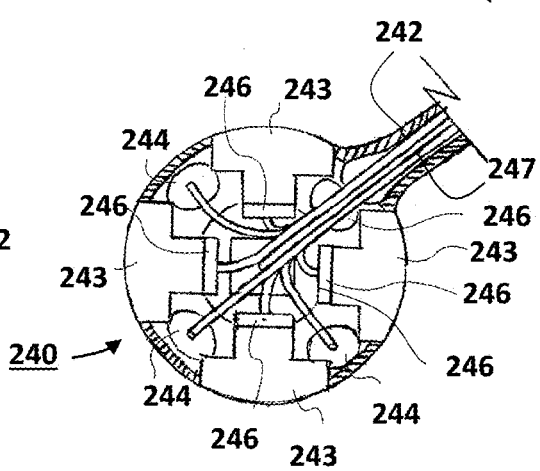
FIG. 17b is a side sectional drawing showing the interior of the very small light weight 3D nano-printed spherical sensor assembly with a plurality of objective lenses and microphones in accordance with and supported by the Enterprise Architecture according to the present invention.

FIG. 13 is an exterior view of the user shown in FIG. 16b wearing headgear disguised as a wig and in FIG. 16b wearing a skull cap with a portable brain activity sensing system with inward facing sensors with a non-evasive wearable brain activity sensing system (i.e., Like Jepsen's Openwater™, system) neural sensing capabilities to interactively operate/drive armature and spherical sensors worn by the user for face-to-face panoramic video teleconferencing. FIGS. 13-14 and FIGS. 16a-16b show a facial sensor and wireless system comprising a portable electronic device, spherical sensor support, neural sensors, voice recognition sensors, and image sensors used for face-to-face panoramic video teleconferencing in accordance with and supported by the Enterprise Architecture according to the present invention. For example, FIG. 13 comprises a Non-Interference Field-Of-View Support Apparatus 218 with a support armature/mast 219, distal end of support apparatus 220, proximal end of support apparatus 221, objective lens 222 assembly of support apparatus, microphone system 223 of objective lens assembly with fisheye 238 objective lenses 238 support armature housing 224, eye tracking system 225 and headgear that includes a neural sensors 226 (i.e., Jepsen or in '214 [103], that at least one a include fMRI sensor 227 system, AMR brain sensing system sensors 228, EEG sensors 229, fNRI 230, or other brain activity sensing systems compatible with the present invention. Wearable neural sensor(s) and PDA 98 mounted on or located locally to the user 6a may be wired 234 or wirelessly connected and include a wireless 235 transceiver that transmits data signals between PDA with software and or firmware 231 for receiving and processing brain activity and receiving and sending other information between host computer 113 of entity 6a system 165. PDA 98 may send information from the entity system 165 through the wireless signal 235 to a 5G telecommunications system and network, or the head mounted PDA device 236 with brain activity sensor system 236, earbud 237 and HMD display(s) 239 to enable user entity 6a situational awareness and for command-and-control purposes. In FIG. 13 the brain activity sensing system includes non-invasive sensors oriented toward the skull and held in place by a user worn head-covering like embodiments in Ritchey and Jepsen's Openwater™ systems and brain activity sensing systems.

In contrast, in FIG. 14 illustrates an embodiment of the brain activity sensing system and headgear 97b of entity 6b that includes invasive sensors implanted through the skull of the user into the brain similar to embodiments in Ritchey patents and Musk's Neuralink™ ASIC brain electrophysiology activity sensing system that detects the neural activity of the brain. FIG. 14 is a cutaway exterior perspective diagram of a person wearing a head gear which includes a 5G headgear with smartphone functionality with presentation, processing, and input means that connects to implanted brain activity sensor system 234 and non-interference support apparatus 218 with a panoramic sensor assembly 218 as compatible with the non-interference facial sensor shown in FIG. 15. Wired connectors or wireless sensors implanted neural sensors communicate with the housing worn on the outside of the users head. The implanted system 234 comprises electrodes and an application-specific integrated circuit (i.e., a microchip or synaptic chip) designed for a special application to detect the neural activity of the brain. In operation in the present invention the brain activity sensing system data and information on neural activity (i.e., time and spatial location in the brain) is communicated from a brain activity sensing system of a type like that described by Neuralink™ system to the Ritchey et. al. where it is operated upon by computer system 113 of entity system 165. Ritchey's computer system processes that information with surrounding imagery derived from a head mounted video camera that records video of the user's conscious percept (CP) to derive a NCC database in accordance with Related Art referenced at the start of this Specification and subject unique matter claimed in the instant CIP application that comprises the enterprise system and method. The sensed brain data from the head implanted Neuralink™ system is correlated with the surrounding environment data sensed in the present invention to draw relationships on the perceptions of the user wearing the mobile Neuralink™ system that is positioned within, about, or a combination thereto the user's head. In operation in the present invention the brain activity sensing system data and information is communicated from the Neuralink™ system to the present invention by operating electronic devices with communication apparatus in a communicative relationship with the present invention. The sensed brain data from the user's brain from the Neuralink™ system is correlated with the surrounding environment data sensed in the present invention to draw relationships on the perceptions of the user wearing the mobile Neuralink™ system that is positioned within, about, or a combination thereto the user's head. For example, in the Neuralink™ system and electrodes that record spiking at a given frequency. The captured signal within a frequency band along multiple threads and multiple locations within the brain is captured and processed by a computer to determine the brain activity at a given location and time. The baseline activity at Time 1 versus Time 2 when a change in activity is captured and is correlated with the activity when different conscious percepts (CPs) are focused upon by the user to build a neural correlates of consciousness (NCC) database in the present invention. Additionally, Neuralink™ brain activity can be sensed and correspondingly coded into machine language that is translated into a NCC database.

Figure 15:
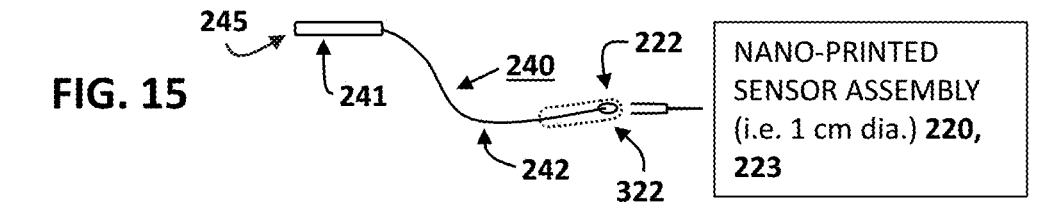
FIG. 15 is a front perspective view of a non-interference field-of-view support device for a facial sensor that blends into the user's profile and may be 3D nano-printed that comprises a embodiment in accordance with and supported by the Enterprise Architecture according to the present invention.
Figure 18:
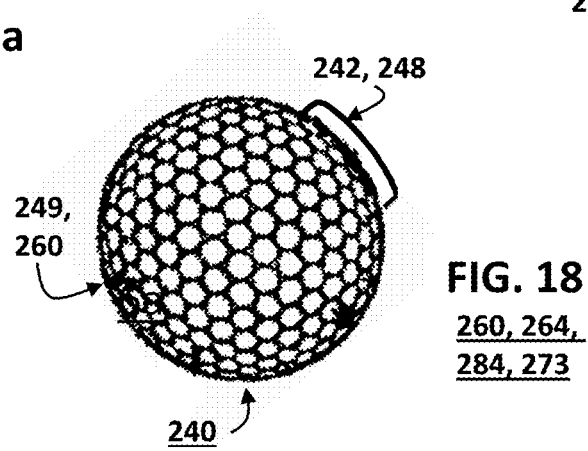
FIG. 18 is a side sectional drawing showing the interior of the very small light weight 3D nano-printed spherical sensor assembly with a flies-eye arrangement accordance to and supported by the Enterprise Architecture according to the present invention.

Referring to FIGS. 15-20 of the present invention, which provide novel embodiments that provide PDA systems 95-99 that reciprocally enable the enterprise 1 that operates using the supporting architectures 16 of the present invention. Wherein the Related Art referenced at the start of this Specification and claimed in the instant CIP application provides various PDA systems and entity systems that enable the invention of the instant transposable transformative enterprise system. FIG. 15 is a front perspective view of a non-interference field-of-view support device 240 for the facial sensor that comprises an embodiment of the present invention which incorporates three-dimensional (3D) nano printer 75 operated by an enterprise 1 worker to design and print at least some portion or all of the support device 240. FIG. 16a is an exterior view of the user shown in FIG. 28a wearing a skull cap 312 (i.e., disguised with a wig 313) with neural sensing capabilities to interactively operate and drive the armature 242 and spherical sensor worn by the user for face-to-face panoramic video teleconferencing. FIG. 16b is the same perspective view of a user shown in FIG. 16a, only without the wig, in order to illustrate all the component embodiment possible of the wireless system comprising the non-interference field-of-view support device which includes a housing 233, 241 with associated electronics for a support armature 242, a panoramic sensor assembly 222 at the distal end 220, eye tracking system 225, a neural activity sensing system with neural sensors, a voice recognition, speech synthesis system, with voice sensors, audio system with microphone and speakers, and an image display for the user all incorporated for use as a face-to-face panoramic video teleconferencing according to the present invention. Said system support housing 241 is at the proximal end 245 of the support armature and is showing looped over and behind the ear in the present example. With the understanding that the support device may be of various configurations and sizes and may be attached to clothing, eyeglasses, HMD or integrated into a HMD, or implanted in some fashion onto the body of the user. FIG. 17a is perspective drawing of the exterior of the spherical sensor with a plurality of objective lenses 243 and microphones 244 of the present invention. FIG. 17b is a sectional drawing showing the interior of the spherical sensor attached to the support armature of the present invention. FIG. 18 is a diagrammatic side sectional drawing of a 3d volumetric VLSIC spherical sensor assembly with imaging and display capabilities with a micro-bead 249 outer surface for use in the present invention. Optionally, in FIG. 18 the armature of the nano 3d printed objective sensor assembly 240 may include a connecting mechanism such as an indentation (not shown) or a short support armature (shown) as socket 242, 248 that that is part of the from the assembly and connects to the mast that connects to the support housing. As shown FIG. 13 and FIG. 15, the distal end of armature may include a clear hard plastic or glass non-reflective material that forms a protective covering 322 over the sensor assembly 222 that attaches to the support armature 242. The covering 322 may be cast using a 3D nano-printer around the spherical shaped assembly 222 as shown in FIG. 13. Or the covering 322 may be cast or slipped over the assembly 222 if capsule shaped as in FIG. 15.

Referring again to FIGS. 15-17b, at least one miniature microphones 244 or audio sensors, like on a cellular phone, to the ninth record audio signatures and transmit them through wiring that transverses support armature 240. The microphones are connected by circuitry located in the sensor assembly support housing 241 that is supported by armature 240. All components that comprise sensor assembly 222 are held in place by support housing 241. The housing is constructed of hard plastic, metal, or a suitable material.

Electronic devices that comprise the sensor assembly 222 are powered electrically from power transmitted through single or multiple fiber optic image conduit or wired circuits 247 to power sensor and transmit images. Still alternatively a transceiver may be incorporated and images may be transferred wirelessly to the host computer for computer processing. The fiber optics or circuitry, depending on the design, is integrated into device 241. Cable functions may not only carry electrical power to devices in the sensor assembly 222, but also power other devices that are part of the support assembly, like servo S1 and S2, the display integrated into the senor head, or other electronic devices worn by the user. Battery packs and other peripheral devices may be attached to device 240 through the connector in order to enhance the operation and functionality of the support device apparatus 240. Thus, apparatus 240 may comprise one of the following arrangements which are compatible with and adopted in full by reference into the present invention: "Fabrication optimization of a microspherical fiber probe with the Taguchi method" by Kuang-Chao Fan1,2,Weili Wang1 and Horng-Shing Chiou3 INSTITUTE OF PHYSICS PUBLISHING JOURNAL OF MICROMECHANICS AND MICROENGINEERING J. Micromech. Microeng. 18 (2008) 259231 (8 pp), Published 5 Nov. 2007, in the Journal "Materials 2014", ISSN 1996-1944, ref. FIG. 7 and Table 4 on page 7 which discloses a fiber probe with a FOV of 270 degrees; Fabrication of an Optical Fiber Micro—Sphere with a Diameter of Several Tens of Micrometers by Huijuan Yu, Qiangxian Huang, and Jian Zhao published 25 Jun. 2014; U.S. Pat. No. 8,007,246 entitled "Apparatus for imaging using an array of Lenses" by Adamo et al., patented 13 Dec. 2011; U.S. Pat. No. 10,565,734, by Bevensee et al., entitled "Video Capture, Processing, Calibration, Computational Fiber Artifact Removal, and Light-Field Pipeline" dated 18 Feb. 2020, ref. FIG. 55f that shows a method for constructing a spherical lens array with fiber optic image conduits and wide-angle lenses. Apparatus 240 panoramic sensor assemblies of types cited here for use at the distal end of the support may be constructed using a 3D nano-printer.

Figure 19:
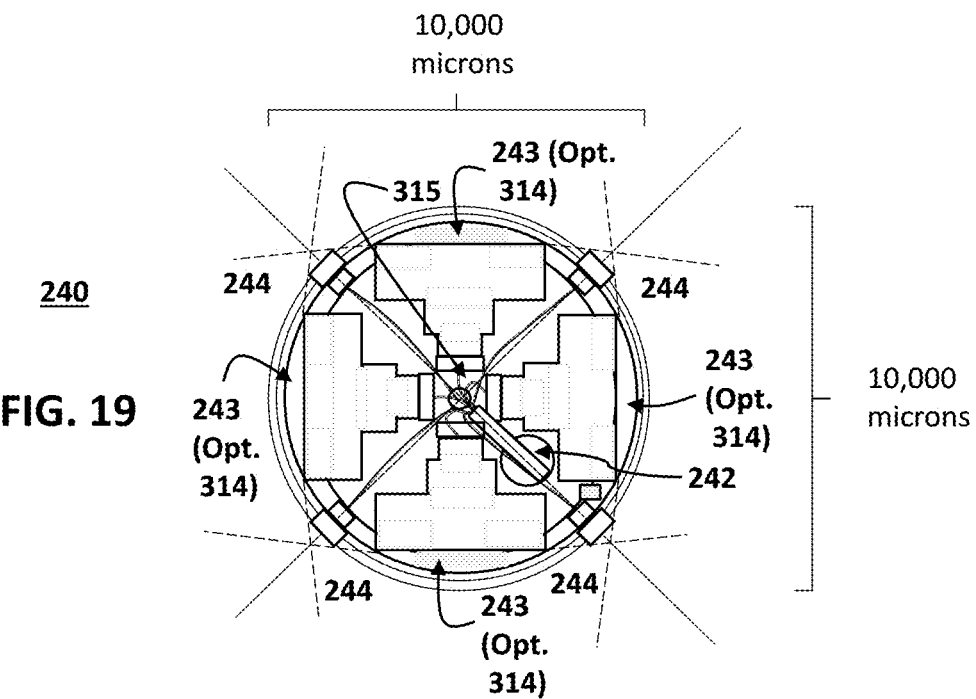
FIG. 19 is a side sectional drawing showing the interior of the very small light weight integrated 3D nano printed back-to-back fisheye lenses printed spherical lens assembly, with fiber optics image conduits, relay optics with distortion removal 3D printed into the design for each lens, and a high-definition image sensor in accordance to and supported by the Enterprise Architecture according to the present invention.

Still alternatively, FIG. 19 is a side sectional drawing showing the interior of the very small (<10,000 microns dia.) light weight integrated 3D nano-printed spherical sensor assembly 240 with a plurality very small fisheye objective lenses 243 and microphones 246 incorporating metamaterial construction and in accordance with and supported by the Enterprise 1 Architecture 16 according to the present invention. The stereoscopic panoramic lens with four lenses with a greater than 180 degree field-of-view lenses facing outward from the center of that housing at 90 degrees apart and to one another such that adjacent lenses have overlapping coverage that results in at least two views of the entire surrounding environment. The assembly also includes microphones between the objective lenses 243 that yield directional audio recording. The image and audio is relayed for processing in a PDA computer system or entity host computer 113 that is part of the entity 6 or 7 computer system 165. The objective lenses are micro-printed in and integrated manner with the housing. Alternatively, 3D printed components are snap fitted together. Electrical power and/or data to and from the assembly may be transferred through the armature. The armature may be semi-flexible so it is manually positioned by the user or positioned in an automated fashion by servos responsive to sensor data. The nano 3D printed support apparatus 240 may optionally incorporate features accordance with applicants prior related art at the nano-scale level but updated by the unique capabilities of multi-material components, compactness, and functionality offered by 3D nano-printing not offered by some current manufacturing and electro-optical components.

Figure 20:
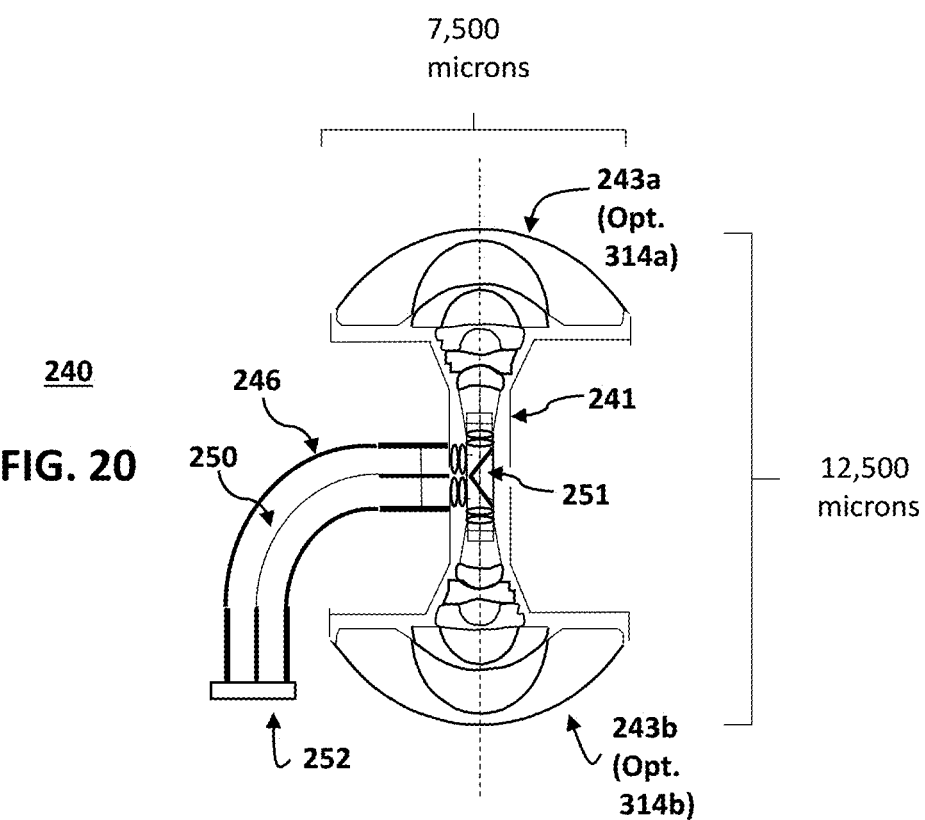
FIG. 20 is a side sectional drawing showing the interior of the very small light weight integrated 3D nano printed spherical sensor assembly with a plurality of objective lenses and microphones incorporating metamaterial construction and in accordance with and supported by the Enterprise Architecture according to the present invention.

FIG. 20 is a side sectional drawing showing the interior cutaway view of another embodiment of the very small, less than 12,500 microns diameter, light weight integrated 3D nano-printed back-to-back fisheye lens 238 printed spherical FOV lens assembly, with fiber optics image conduits, relay optics, optionally with metamaterial, optical diffraction grating, or a Fibreye™ arrangement to remove barrel distortion caused by the fisheye lenses, and with at least one high definition image sensor 246 in accordance to and supported by the Enterprise 1 Architecture 16 according to the present invention. Systems and methods compatible, of a type, employed, and adopted in the present invention in designing and manufacturing by reference employed and that enabling 3d nano printing optical and metamaterial components including electrical circuitry at the nano level to construct very small devices described in FIGS. 15-20 include: Sofia Rodriguez, Nanoscribe™ GMBH's article entitled "Ultra-precise 3D Microprinting for Optical and Photonic Components", Photonics Spectra, December, 2018; Aydin Sadeqi et al, article entitled "Three dimensional printing of metamaterial embedded geometrical optics (MEGO)" in Microsystems a & Nanoengineering", dated 16 May 2019; Timo Gissibl et al., "Sub-micrometre accurate free-form optics by three-dimensional printing on single-mode fibres", nature communications, 4 Aug. 2015; U.S. Pat. App. 2017/0310907A1, by Wang, Michael D., entitled "Flat Lens Imaging Devices and Systems", dated 26 Oct. 2017 that reduces thickness of a lens requirements by using an electronic device used in the present system, assignee Microsoft; Sony IMX274LQC 16.9 4K imager used in FIG. 19; U.S. Pat. No. 9,578,159 B2 by Prasad Muthukumar, 21 Feb. 2017 that uses metamaterials to reduce fisheye lens thickness and incorporates firmware to remove distortion from caused by fisheye lens; Ricoh Theta V 360-Degree Handheld Spherical camera with directional audio, and firmware for download to manipulate back-to-back fisheye imagery.

Miniaturization of bio-mechatronic and mechatronic systems and devices down to the nano-scale level using 3D printers enable the present invention. For instance, 3D printing of the sensor assembly housing and optics is incorporated into the present invention. FIGS. 15-20 illustrates a fisheye lens assembly printed within a 10 mm diameter spherical housing. This facilitates light weight, smaller form factor, detailed design, innovative capabilities, more rapid production, less materials, lower cost and a lens system that can be positioned forward a user's face with less interference than in previous designs (i.e., Ref. U.S. patent application Ser. No. 15/152,214). The assembly is manufactured by using two-photo polymerization (2PP) based 3D microprinting in situ with nano-scale precision. Both aspherical and hemispherical lenses with concave and convex sides are printed to a scale. The layup can be accomplished in situ, with the 3D printer applying multiple layers of opaque or clear materials of dissimilar materials using different printer heads. The assembly may be printed on as image sensors, LED/OLED, and other microelectronic structures such as MEMs. Electronics circuitry may be etched or 3d printed using conductive materials. The basic process starts with a 3D CAD model, which is sliced and hatched, then is 3D laser printed using resin and in a supporting substrate which is rinsed off to remove the unpolymerized material. (Ref. Photonics Spectra, December 2018) A company incorporating 3D nano-printing that can manufacture the systems shown in FIGS. 15-20 include Nanoscribe, Hermann-von-Helmholtz-Platz1, Eggenstein-Leopoldshafen, 76344 Germany; 3mail:info@nanoscribe.de; www.nanoscribe.de, Germany; email: info@nanoscribe.de; www.nanoscribe.de.

For example, in FIGS. 15-20 the Non-interference field-of-view support apparatus 240 with a plural number of lens 243 systems may be fabricated onto the distal end of the support armature 242. The assembly and armature may be 3D-printed as separate but connecting pieces or as a single unit through which the image fiber(s) 247 may be joined to the image sensor or plug into a housing at the proximal end with an image sensor at the distal end of the armature. Additionally, various materials and metamaterials 314 may be used to print the assembly. For instance, optics can be printed in clear plastic, etched or printed circuitry 315 to carry electrical current or data may be etched and printed, with various other materials being printed using 3D nano printing. For instance in FIG. 19, a length of clad flexible fiber optic image conduits 250 may be laid down on a support structure and the then adjoined at each end by printing a 3D printed support structure to hold the image sensor 252 at one end and the fisheye optical assembly objective lenses 243a and 243b, and the relay optics 251 and focusing optics 241 at the other end of the device 240. Relay optics that are of a type that may be used in the present invention of a type to optically turn an image 90 degrees on an optical axis include mirrors, prisms, or fiber optic image conduits. Single or multiple fibers can carry the image to the imager in device 240. A protective cladding 250 is placed around the fiber optic image conduit(s). The armature is semi-flexible so it is manually positionable by the entity or positioned in an automated fashion by servos responsive to sensor data. Relay optics and metamaterials 314 may be incorporated to lesson or remove the distortion. For instance, in FIG. metamaterials 314 may be incorporated to shorten the optical path and profile of wide-angle lenses in the present invention. Additionally, components may be snap fit together or adhesively connected once 3D printed. Nano printed metamaterials may be arranged using microscopic viewing systems and manipulation devices controlled by the operator. Ref. Gissibl, T. et al., Sub-micrometre accurate free-form optics by three-dimensional printing on single-mode fibres. Nat. Commun. 7:11763 doi: 10.1038/ncomms11763 (2016). And companies incorporating 3D nano-printing and micro-printing that can manufacture the systems shown in FIGS. 18 thru 21b is Nanoscribe, Hermann-von-Helmholtz-Platz 1, Eggenstein-Leopoldshafen, 76344 Germany; email: info@nanoscribe.de; www.nanoscribe.de Germany; email: info@nanoscribe.de; www.nanoscribe.de. Plural or single sensors may be incorporated into the design and include associated image processing software and/or firmware to process images and audio for further computer processing, transmission, or display. Preferably the image sensor or sensors (depending on the design) is a low-light sensor that can amplify the image that is transmitted through a fiber optic image conduit. And preferably the image sensor has a small volume and high image resolution 4K low light sensitivity image sensor that allows low light imaging and includes image stabilization. Cell phones with image sensor system of a type that that may be incorporated into the instant invention support armature with sensor assembly and support housing are the Apple iPhone Xs or 11 Max, Google Pixel 3/Google Pixel 3 XL (wireless charging), and Samsung Galaxy S10 (wireless charging). The image sensor may be located in the image sensor assembly, the armature, a head worn housing, or in the phone carried by the user. Optionally, the images may be optically transmitted to the image sensor, or an over-the-air signal may be sent over a transceiver to communicate the image signal to the cell phone, head mounted device, or other processing or display device. The images from the camera are typically processed for viewing by a local or remote user to view on a display device (i.e., by the PDA 95-99 or other recipient system. The images from the camera will typically be processed in the correlation engine with the brain activity signatures to assist the user or recipient being in negotiating the environment and building and updating the NCC database. A handheld camera with a 4K video image sensor and a directional microphone system compatible with the present invention (i.e., the Ricoh Theta V 4K 360 spherical camera). Optical arrangements of a type that may be scaled to the nano-level and that are compatible with the present assembly system 240 are found in Pub. No.: US 2013/0242040 A1, MASUDA et al., Pub. Date: Sep. 19, 2013. An audio system 212 including either or both a microphone and speaker system may be integrated into the 3D printed sensor assembly. Preferably the assembly has a spherical FOV image and spherical FOR audio system. The microphone system may comprise one like that found in the above named cell phones, or a fiber optic microphone of a type from Optimic 1200—Extremely Demanding Applications Complete EMI/RFI immunity High signal quality High SNR, Low THD Lightweight or ruggedized Negligible signal loss over distance Long term reliability, stability Optoacoustics Ltd. Moshav Mazor 73160 Israel US Toll Free: +1 866-867-5029 Phone: +972 3-634-4488; Fax: +972 3-634-9292 Product inquiries: sales@optoacoustics.com Support inquiries: support@optoacoustics.com General inquiries: info@optoacoustics.com panoramic camera manufacturer. Preferably, with plural of microphones spaced at distances apart to provide directional audio and ambisonic audio processing with spherical amplification FOR coverage to a local or remote user to listen to from a PDA or other recipient system. Ref. Nanoscibe datasheet, on specifications of 3D nano scale 3D printer by Nanoscibe GmbH, 76344 Eggenstein-Leopoldshafen, GE; and U.S. Pat. App. 2019/0227525 A1, by Edward Mehr et al., entitled "Real-time Adaptive Control of Additive manufacturing Processes using Machine Learning, 25 Jul. 2019, of Relativeity Space, Inc. Inglewood, Calif. using A.I.3D, each citation in this paragraph incorporated by reference in their entireties into the present invention to manufacture optical, facial, micro circuitry, and all other component embodiments of the present invention.

Figure 21A:
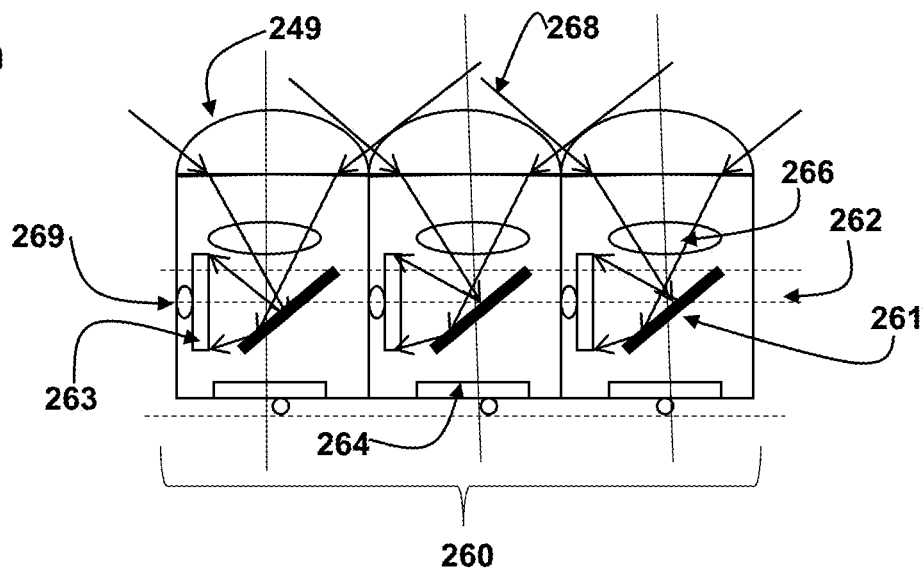
FIG. 21a is a side sectional view of an embodiment of an integrated camera and display system that may be incorporated on the outward facing curved cylindrical display assembly in FIG. 21a-22d in accordance with the present invention showing the image capture phase of the system.
Figure 21B:
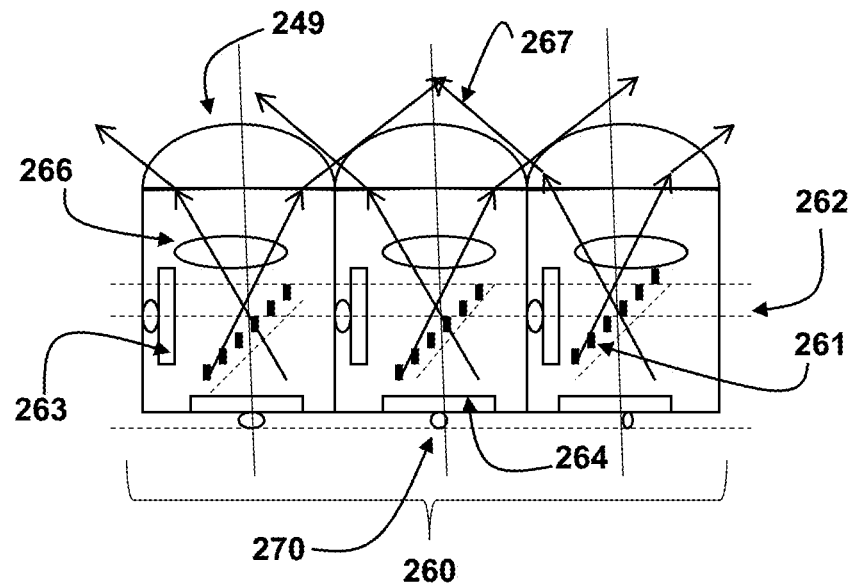
FIG. 21b is a side sectional view of an embodiment of an integrated camera and display that may be incorporated on the outward facing curved cylindrical display assembly in FIG. 22a-22d accordance with the present invention showing the image display phase of the system.

FIG. 21a and FIG. 21b illustrate an integrated visual capture and display system 260 which may be integrated into the present invention. FIG. 21a and FIG. 21b are greatly enlarged side sectional view of an embodiment of the integrated camera and display system 260 in FIG. 18, FIG. 22c, FIG. 25 (7a), and FIG. 26c. Operation, components, and applications of the integrated visual capture and display system 260 are described in the "Related Applications" of the present invention, specifically U.S. patent application Ser. No. 15/152,214 filed on 11 May 2016 entitled "Non-Interference Field-Of-View Support Apparatus For A Panoramic Sensor" (granted as U.S. Pat. No. 10,447,966 B2). The integrated visual capture and display system 260 is incorporated by reference in its entirety as a component in some devices described in the instant invention in sufficient detail for those skilled in the art to understand the integrated and display system 260 and like systems incorporation into embodiments of the present invention.

For example, FIG. 21a of the present invention shows the image capture phase of the integrated visual capture and display system 260. In the image capture phase each objective lens 249 of the lens array reflects its field-of-view coverage image of the surrounding environment on an optical path 268 through a respective relay lens 266, to respective closed micro-mirrors 261 that have been activated to a position of 90 degrees to reflect the image to the respective image sensor 263. The captured image is then processed for analysis in computer 165. The micro-mirror drive circuitry 269 is operated to open and close the micro-mirrors of the system 260 which are activated by computer system 165 which is at least one responsive to a PDA 95-99 or an entity 6 or 7 on which the integrated visual capture and display system 260 is employed. The image sensor portion of the system may incorporate and be integrated to a PDA or Entity Region-of-Interest (ROI) and/or feature/target tracking system that assists the system 165 in identifying PDA and/or entity Conscious Precepts necessary for determining PDA and entity Neural Correlates of Consciousness. FIG. 21b of the present invention shows the image display phase of the integrated visual capture and display system 260. In the image display phase each electroluminescent display emitter 264 such as a LED, OLED, LCD, or compatible type of display emitter is activated to reflect a portion of light that represents and portion of a composite image transmitted through open micro-mirrors 261 that are activated to be open by micro-mirror drive circuitry 270, through a respective relay lens 266, and then to through a respective objective lens to a user 2, or entity 5, 6, or 7 for viewing, presentation, or additional processing. The micro-mirror drive circuitry is responsive to the display control portion of system 260 which is in turn responsive to computer system 165 which is at least one responsive to a PDA 95-99 or an entity 6 or 7 on which the integrated visual capture and display system 260 is employed.

Figure 22D:
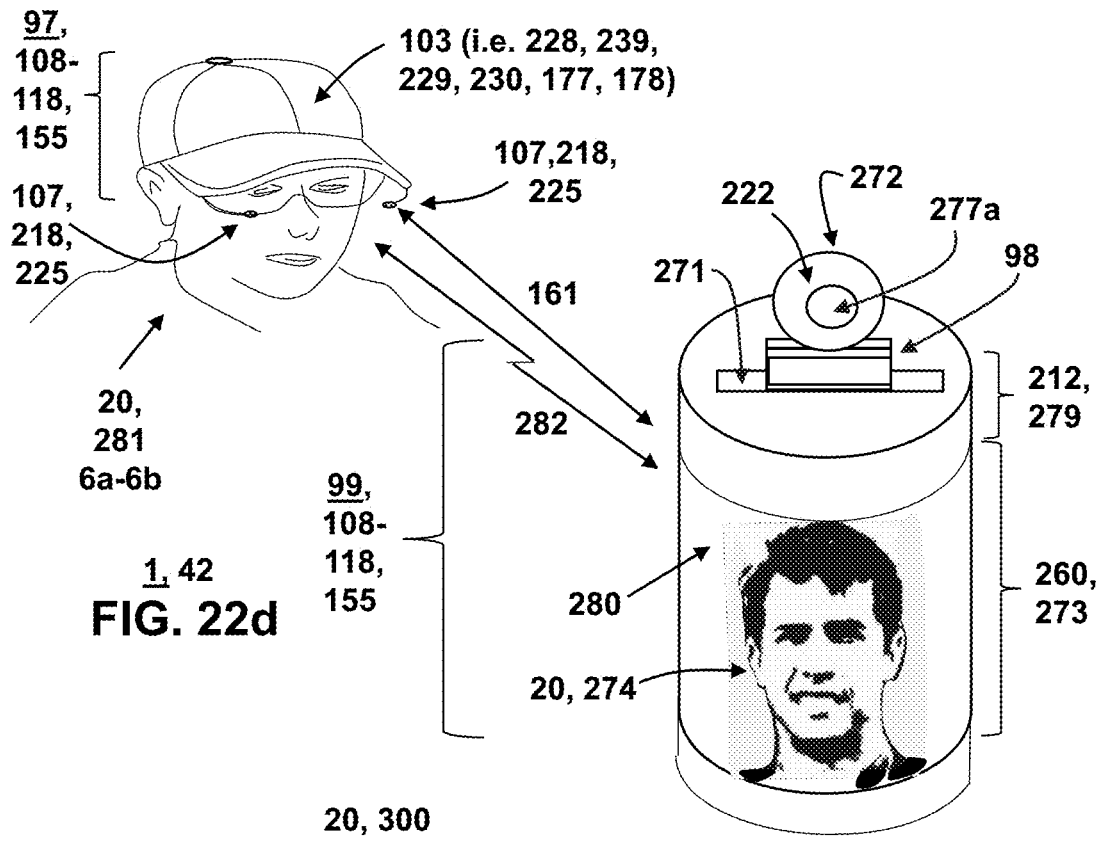
FIG. 22d is a perspective view of an additional alternate arrangement for a PDA with 360 FOV image capture and display coverage and 360 directional audio coverage and includes an inductive charging
Figure 23:
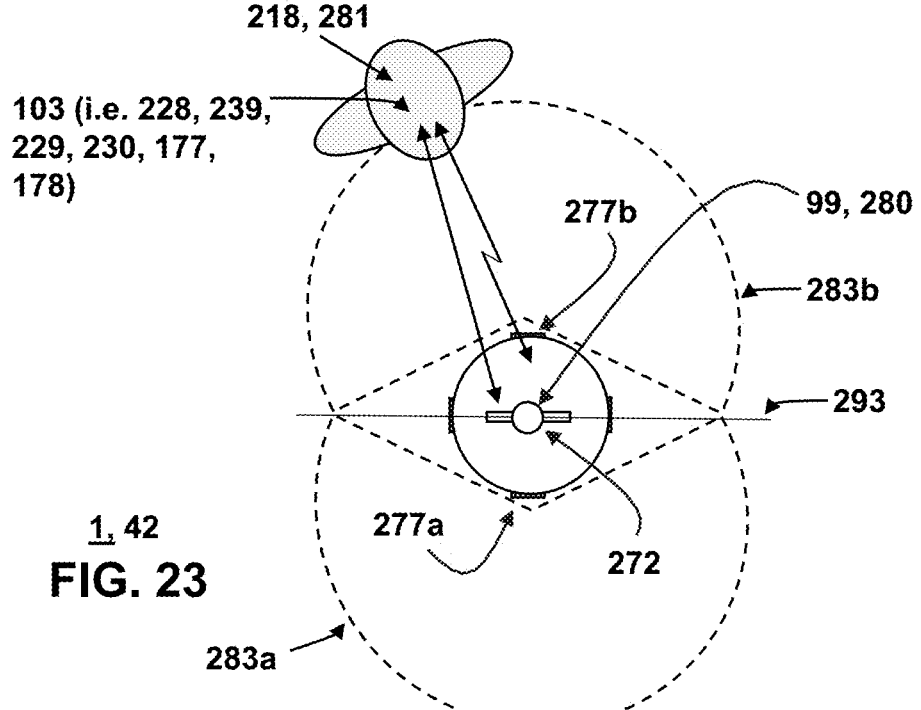
FIG. 23 is a plan view of the PDA's 360 FOV image capture and display coverage and 360 directional audio coverage shown in FIGS. 22a-24b.

Referring to FIGS. 21a-23b of the present invention, applicant's related applications incorporate utility and design patent embodiments of a virtual video assistant 99 device which function as a personal digital assistance 300 to a user in a surrounding environment. In accordance with the present invention various volumetric shapes may be designed realized the invention. For instance as shown in FIG. 22a-23, and in FIG. 25 a cylindrically shaped embodiment of the device 99 a 360-degree directional microphone systems and audio amplification system faces outward the device; a 360-degree panoramic camera systems and with heat ventilation at the top and bottom sides that faces outward toward a user and a surrounding environment, and 360-degree cylindrical electroluminescent display that faces outward toward a user and the surrounding environment. The display may incorporate a touchscreen display and a display with an integrated camera integrated into the display, like that shown in FIGS. 21a-21b. In the present example, an induction charger for a phone may be placed on the flat top of the cylindrical shaped device 99. Various cameras, and phone docking designs, and design shapes representing a single design concept for the personal digital assistant 99 are shown in the said design patent by Ritchey et al filed on 13 Oct. 20. Also, disclosed herein and in applicant's related art are power and data adapter ports at the bottom side of the device and ventilation underneath a permeable textured covering. Or alternately, outward facing audio microphone sensors and audio amplifiers are located behind ribbed holes in the housing facing outward from the virtual video assistant and heat is ventilated outward from the device through the holes. The personal digital assistant devices shown graphically in the referenced design patent application by the present inventors depict permeable areas covered with a fabric material or alternatively where ribbed openings that form an outer covering of the ornamental design to facilitate outward facing audio input sensors and audio output amplifier design, and heat ventilation systems behind and concealed by outer covering design. Computer processing with artificial intelligence processor, region-of-interest processing, correlation process, and communication systems housed within the internal volume of the virtual assistant housing in the center of the device in accordance with art listed in the related applications section of the present invention. Internal components of the assistance devices accessible through at least one the bottom or top of the devices described in the related applications. An ornamental design feature of one embodiment of the device includes an LED backlit feature under the electroluminescent display that gives the impression the electroluminescent display is floating on, for example, a countertop. The personal digital assistant with a volumetric housing with a 360 degree field-of-regard display screen and with multiple lenses, A.I. computer processing functionality, and ROI tracking. The personal digital assistant may a camera that records visual and depth imagery with short and long-throw Infrared illuminators located between the camera lenses which provide directional camera system.

Still referring to functionality of personal digital assistant embodiments shown in FIGS. 21a-23b: The design application illustrates embodiments of the concept virtual video assistant design which constitutes a personal digital assistant of a type that may be used in constructing the electroluminescent displays shown in the present invention and related patents. Prior art components of a type that are enabling and that are used to construct the virtual video assistants shown in the present invention hereby incorporated by reference in their entireties into the present application include: JP Pat Appl. 201715660, "Multi-sided or curved display device" by Shinya Niioka, filed Mar. 3, 2016; U.S. Pat Appl. 2017115790A1, "Touch Detection Device", by Japan Display Inc., filed Jan. 9, 2017; GB Pat 2,451,730 A, entitled combined illuminated advertising and visual display unit; 10 Jul. 2008; and U.S. Pat. Appl. 20130127917 entitled "Display Device", by Jun-Ho KWACK, filed 21 Mar. 2012; article entitled "How Microsoft is making its most sensitive HolloLens depth sensor yet", by Mary Branscombe, Oct. 9, 2018; published by ZDnet, technology section; article entitled "Inside the ICE Shelf: using Augmented Reality to Visualize 3D LIDAR and Radar of Antarctica" by Alexandr L Boghosian et al., published in the Photogrammetric Record 2019 The Remote Sensing and Photgrammetry Society and John Wiley and Sons Ltd.; and lessons learned by applicants in designing seamless shaped volumetric displays found in U.S. Pat. No. 10,565,734, by Bevensee et al., entitled "Video Capture, Processing, Calibration, Computational Fiber Artifact Removal, and Light-Field Pipeline" dated 18 Feb. 2020, ref. FIG. 51 and FIG. 65; and applicants related art.

Objective of the invention use cases of the personal digital assistant 300 embodiments that comprise Related Applications the applicants design patent application entitled "Virtual Video Assistant for a Surrounding Environment" includes: 1) The ability of a person using the 360 degree field-of-view virtual video assistant being able to move around in their environment and still maintain face-to-face contact with a person using the same system at the other end of the two-way teleconference; 2) The 360 virtual video assistant being able to observe multiple activities and locations in the surrounding environment simultaneously so the user can maintain situational awareness and security; 3) and the 360 degree virtual video assistant being able to present imagery and audio to multiple persons around different sides of the virtual video assistant so the participants do not have to crowd around a single monitor; and 4) The 360 virtual video assistant's ability to use artificial intelligence to recognize a problem through pattern recognition that a smart speaker system cannot recognize and ability to alert first responders (i.e. monitoring of a child, the elderly, or person at risk).

The integrated camera and display system 260 may be used as a covering on a user garment, head covering, eye glasses, a HMD, on the support armature or device at the distal end of the support armature, a robot, a human-like entity, or a PDA, or the exterior or interior of a vehicle, to include a car, helicopter, drone, airplane, boat, spaceship. Optionally, the image sensor or the display diodes of the integrated camera and display unit may be replaced with an array of solar collection sensors to provide electrical power for the device on which the integrated covering is placed. The covering may be designed to be transparent or opaque when viewed from the front or backside. For example, allowing a person in a vehicle to choose whether to look out of a vehicle or not to look out of a vehicle. Multiple layers of the covering may be incorporated on a device. The covering maybe constructed to be rigid or flexible and supported by a rigid structure or a flexible structure (i.e., pneumatically). Devices in the present invention that the camera display arrangements or the like shown in FIGS. 21a-b may be integrated with include those shown in FIGS. 11-14 and 16-20.

Referring now to the FIGS. 22a-24b of the present invention, in accordance with Related Art referenced at the start of this Specification and subject unique matter claimed in the instant CIP application that comprises the enterprise system and method.

The virtual panoramic personal digital assistant (PDA) system 99 embodiments described in FIGS. 22a-24b include functionality described in FIGS. 4-10 in order to sense, record, and process information about a user. This sensed, recorded, and processed information is then used to at least one update, and construct and train an A.I. capable device or human-like entity in accordance with and supported by the Enterprise 1 Architectures 16 according to the present invention. FIG. 22a is a perspective view of a PDA 99 with 360 FOV image and/or video capture system with objective lenses 277 and display coverage and 360 directional audio system with plural microphones 275 and speaker 276 system and includes an inductive charging unit 271 built in that charges cellphone 98 when it is laid on the flat surface on the top of the PDA. The virtual PDA 99 includes all the functionality outlined in FIG. 4-6 in order to sense, record, and process information about a user for later use in constructing and training an A.I. capable device or human-like entity in accordance with and supported by the Enterprise Architecture according to the present invention. The virtual PDA includes a host computer with local and/or remote artificial intelligence computer processing capabilities. The PDA has the capability to display remote or local image(s) of subjects(s) of interest 274 on the PDA. Optionally, in addition or in place the virtual PDA may include a LIDAR 278 system as shown in FIG. 22a. FIG. 22b is a perspective view of a PDA with a panoramic camera 272 with at least circular and preferably 360 FOV image capture and display coverage and 360-degree directional audio coverage and includes an inductive charging. In FIG. 22b the camera may alternatively include a plugin charging 316 receptacle for charging that a panoramic camera 272 or cell phone 98 that plugs into for charging and for data exchange with the PDA 99. The virtual PDA may include fabric 279 that sound may penetrate though covering audio microphones and audio speakers. The image capture is facilitated by docking a 360-degree handheld camera into the top of the PDA. And includes functionality outlined in FIG. 4-6 in order to sense, record, and process information about a user for later use in constructing and training an A.I. virtual PDA 280 capable device such as the PDA shown in FIGS. 22a-24d or human-like entity in accordance to and supported by the Enterprise 1 Architectures 16 according to the present invention. The virtual PDA may also have graphics, text, still or motion imagery displayed upon it. And the virtual may be used for teleconferencing, surveillance, PDA touch screen control, or lighting, just to name a few applications. FIG. 22c is a perspective view of a PDA with 360-degree FOV image capture and display coverage and 360-degree directional audio coverage and includes an inductive charging. The speaker system may be put on the top or bottom, because an integrated camera capture and OLED curved display screen 273 disclosed in FIG. 21a-21b. Alternatively, the display may be comprised of spherical or flat facets facing in many directions to facilitate multi-sided viewing of images on the PDA. Preferably, the timing of the camera and display on and off is accomplished at a high (>120 Hz/sec) refresh rate so that it is not noticed by a viewer. As commonly done in the art the microphones and speakers may be concealed with fabric for esthetic purposes. FIG. 22d is a perspective view of a PDA 280 with and 360-degree field-of-view (FOV) 161 image capture and display coverage. The PDA 280 also includes a 360-degree field-of-regard (FOR) 162 audio capture and presentation coverage. The PDA 280 also includes at least one a docking 317, plug-in 316, or inductive charging 271 system. In this embodiment an onlooker 2 or 6a uses a headgear personal digital assistant (PDA) 97 system with a HMD system 239 like that disclosed in FIGS. 4-11 to wirelessly communicate with subscriber 20 whose panoramic camera 272 with back-to-back adjacent field of 360-degree FOV/FOR coverage with fisheye lens and image 274 and sound system 212 that plugs into the cell phone 98 are operated to provide an interactive audio-visual presentation with the PDA 99. The panoramic wireless audio-visual signal 282 is operated upon by the virtual PDA and cell phone to provide two-way audio-visual presentation to the local user 281 of the virtual PDA 99 and the headgear PDA 97 system with the remote user displayed on the PDA. The PDA and/or cell phone with camera communicate with one another and include at least one a computer with software and firmware to sense, record, process, and store information that interactively assist the user subscriber 20, 274. The headgear may also include at least one non-interference FOV support apparatus 218 and/or an eye-tracking system 225 with ROI 107 tracking capability used to help identify CPs. The headgear may include a brain activity sensing system 103 (i.e., 177/178) for use in constructing and/or accessing an NCC database based on the user's CP monitored by PDA that is located locally to the user wearing the headgear. Cell phone 98 includes a spherical camera with audio-visual capability that records the surrounding environment 161 that includes user subscriber 20, 281.

Still referring to FIGS. 22a-22d and FIG. 23, it will be obvious to those skilled in the art that various embodiments described in FIGS. 22a-22d may be incorporated to assist in achieving various applications and enterprise 1 fulfillment center 42 objectives of the present invention. For instance, in some applications a headgear 97 with a brain activity sensing system 103 is preferable and in other applications no headgear would be worn by the local or remote user subscriber 20. Software and firmware of a type that may be integrated into the host computer 113 of the PDA 97 and 99 system to operate upon sensed, recorded, and to process information in order to achieve a result using artificial intelligence that is disclosed and adopted in full by reference includes that described by Lichao Chen et al. (Lichao Chen, Sudhir Singh, of the Department of Electrical and Computer Engineering, University of California, Los Angeles, Calif. 90095; Thomas Kailath, and Vwani Roychowdhury of the Department of Electrical Engineering, Stanford University, Stanford, Calif. 94305) entitled "Brain-inspired automated visual object discovery and detection", published online Dec. 17, 2018, at www.pnas.org/cgi/doi/10.0173/pnas. 1802103115, b.) and "Supporting Information Appendix: Brain-Inspired Automated Visual Object Discovery and Detection to the same paper; and in U.S. Patent 2009/0196493, dated 6 Aug. 2009, by Widrow et al. entitled Cognitive Method and Auto Associative Neural Network Based Search Engine for Computer and Network Located Images and Photographs; Cognitive Agent that Learns and Organizes (CALO) Software, and U.S. Patent Application 20070124292 A1, by Kirshenbaum et al., dated 31 May 2007, entitled Autobiographical and Other Data Collection System, and IL, is a system compatible with and integrated by reference as art incorporated into the present invention is the Ultra-Vis, Leader, system developed by ARA, subsidiaries MWD, Vertek, and KAD, and other companies to include Lockheed Martin and Microvision Incorporated™ teaches a stereoscopic video logging system with querying. This embodiment includes all the functionality outlined in FIG. 4-6 that uses a PDA computer systems 113 and 165 that operates to sense, record, and process information about a user subscriber 20, 281 for later use in constructing and training an A.I. capable device that incorporates at least one artificial neural network with back propagation or human-like entity 5, 6, 7 with a non-volatile memory that learns in accordance to and supported by the Enterprise 1 Architectures 16 according to the present invention. For instance, user subscriber 20 may interact with the PDA device 95-99 using touch, voice, visual, gesture, or telepathic communication. It will also be understood by those skilled in the art that besides a bio-mechatronic system 6a (i.e., 177) or 6b (i.e., 178) a mechatronic system 7 may interact with a PDA 300 (i.e., 95-99).

FIG. 23 is a plan view of the virtual PDA 99 shown in FIGS. 22a-22d with a 360-degree audio-visual image capture and audio presentation coverage. The virtual PDA 99 may also include any of the functionality outlined in FIGS. 4-13 in order to sense, record, and process information for updating and building a relational database for later use in constructing and training other A.I. capable devices or a human-like entity systems with A.I. in accordance with and supported by the Enterprise 1 Architectures 16 of the present invention. The dashed line 283a represents the FOV coverage of the objective lens 277a and dashed line 283b represents the FOV coverage of the objective lens 277b of camera 272 is mounted on cell phone 98 which is in turn mounted upon virtual PDA 99 that is in wireless communication 282 with local user 20 with headgear 97 with a brain activity sensing system 103. PDA capable devices 97, 98, 103, 107, 272 may be comprise node devices that have a wireless signals 235 to the 5G telecommunication system and network 25 that enables two-way telepresence between the local user and the remote user and the architectures 16 and fulfillment center(s) 42 of the enterprise 1 system. The subscriber 20 operates panoramic camera 272 with back-to-back adjacent field of 360-degree FOV/FOR coverage indicated by line 293. The panoramic camera with fisheye lens records images 274 records directional audio which are both communicated to the virtual PDA 99 sound system 212 through the cell phone 98 that are operated in an integrated and synchronized manner to provide an interactive audio-visual presentation on the PDA 99.

FIG. 24a is a perspective view of a 360 degree holographic projection PDA system 290 image capture and display system that includes all the functionality described in FIGS. 4-13 in order to sense, record, and process information for updating and building a relational database 37, 100 for later use in A.I. capable PDA devices 300 or a human-like entity 5, 6, 7 systems with A.I. in accordance with and supported by the Enterprise 1 Architectures 16 of the present invention. In a first embodiment the panoramic holographic projection PDA system 290 analyzes the brain activity expressions 294 and displays a holographic image 295 of a 3d image formulated by an electro-optical holographic computer system 294, 296 senses, records, and generates a user's facial in real time by a multi-camera system 291 comprising the PDA 360 panoramic camera 272 and facial camera system 107.

Optionally, portions of the surrounding environment may be generated. And additionally, a LIDAR system may be incorporated to generate imagery that is processed into a 3D holographic image that mimics the recoded image by using 3d image processing hardware and software known in the art. In a second embodiment the system analyzes the brain expressions and animates a user's prerecorded facial expressions 297 draws from a database of prerecorded 3D a catalog of facial expressions from of the person talking and provides a mimicked simulation of a subscriber based on the subscribers words and/or brain activity to generate a holographic simulation that mimics the facial or bodily response which is transmitted to a remote user of in a remote location that is viewed a generated holographic projection PDA. In this manner the camera system's holographic projection PDA 290 that is in wireless communication 282 with local user subscriber 20, 281 with headgear 209 a brain activity sensing system 103. PDA capable devices 97, 98, 103, 107, 272 may comprise node devices that transmit wireless signals 235 to the 5G telecommunication system and network 25, 43 that enables two-way telepresence between the local user 20a and the remote user 20b using the architectures 16 and fulfillment center(s) 42 of the enterprise 1 system. In FIGS. 24a and 24b a true-color three dimensional laser real-time image recording and projection system using active recording components such as, electronic heterodyne mixers, coherent primary color lasers, electro-optical detectors, electro acousto-optic modulators, electro-optical spatial light modulators, combined with passive components including electronic band-pass filters, optical beam splitters, optical beam expanders, lenses and mirrors. For example, the image holographic projection PDA system 290 uses lasers, beam combiners and SLM's to generate and project a holographic image. Systems and applications included by reference in their entireties into the present invention enabling holographic display include U.S. Pat. No. 6,760, 134 B1, entitled "Multicolor Electronic Holography and 3D Image Projection System", by Schilling et al. Still alternatively, instead of holographic projection an OLED 3d image may be generated by incorporating a GIWOX 3d Display LED Fan, dated 6 Jul. 2004, may be mounted on the wall or table top whose systems and applications are included by reference in their entireties into the present invention. In practice, the same information derived for use in holographic embodiment is put in a format for display tailored for display by the OLED 3D display system (not illustrated).

Figure 25:
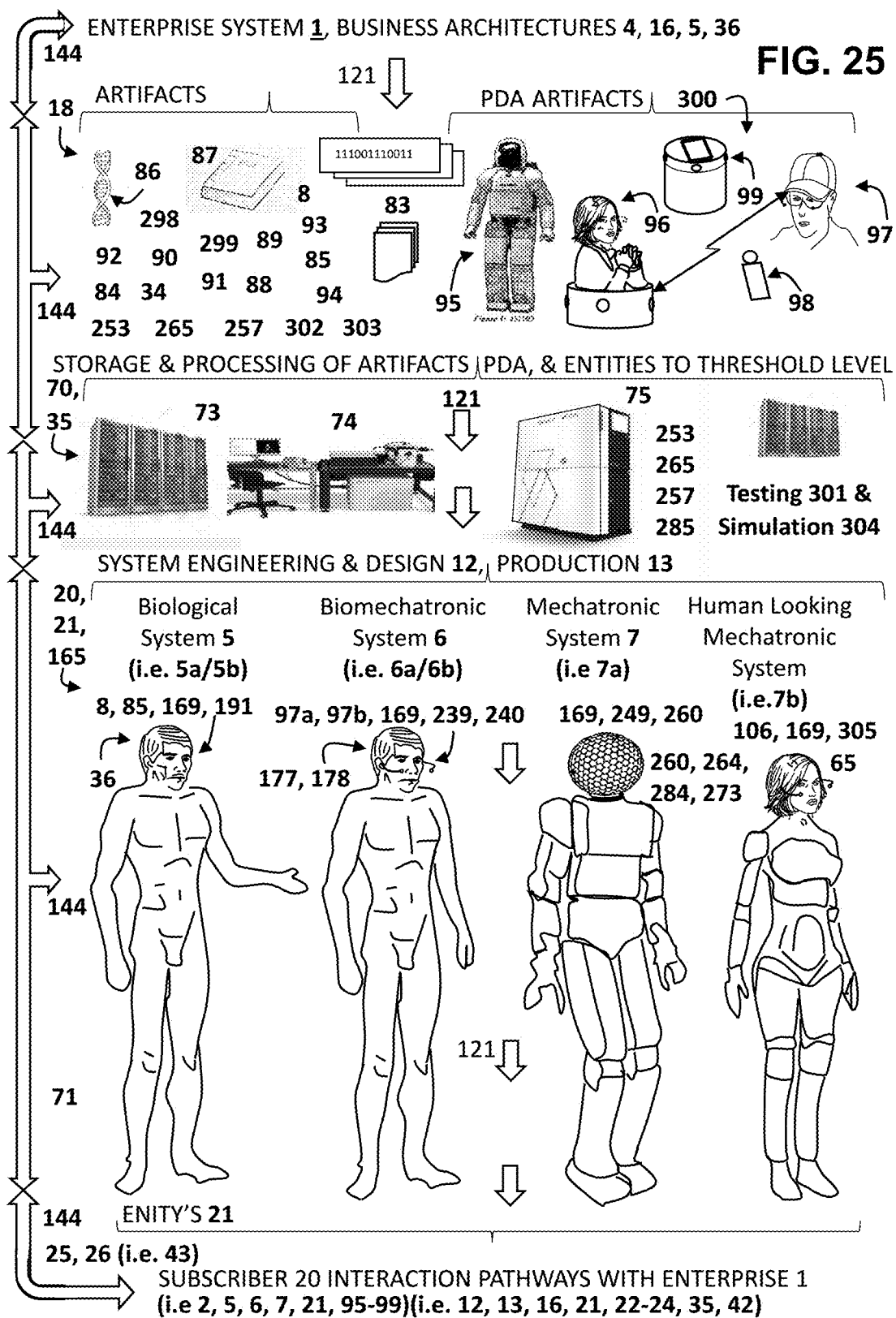
FIG. 25 is diagram illustrating steps in fulfilling a subscriber's requests for products and services from a fulfillment center in the human emulation enterprise 1. Both systems & methods for managing personnel and systems necessary to fulfill a subscriber's requests for products and services (i.e., emulation software, firmware, training, hardware, storage, artifact collection, and entity design and maintenance) are described in the diagram.

FIG. 25 is diagram illustrating steps in fulfilling a subscribers request for products and services using business architectures 16, fulfillment center 36, system work groups 35 that comprise the human emulation enterprise 1. An arrow(s) 144, indicates typical access points that subscribers, users, recipients, user agents, and user venders can access the enterprise 1 via the 5G telecommunication system and network 25, 43 or via shipping and delivery 26. Access points 144 comprise either physical places or online sites on the internet 19 where subscribers, user venders, and user agents, and enterprise employees may interact to receive products and services and fulfill transactions. Both systems and methods for managing personnel and systems necessary to fulfill a subscriber's request for products and services (i.e., mimicking and emulation software, firmware, training, hardware, storage, artifact collection, and entity design and maintenance) are described in this diagram. Arrows going down the center of the diagram illustrate the linear progression of collecting information and developing devices, systems, and collecting data to enable emulation of a subscriber to the business. In FIG. 25 a Human Emulation Enterprise System & Method 1 is disclosed comprising the following systems and methods which basically include first a business architecture with one a secure subscriber information system and second a system for handing a subscribers physical and digital content artifacts 18 over a secure telecommunication system the business and subscriber can interact across. The enterprise 1 includes using as secure as possible shipping which might involve couriers in some instances, and a 5G telecommunication system with quantum computer safe encryption of all personal data. Lattice Encryption algorithms represent a quantum safe type of encryption system that is of a type being constructed for the National Institute of Science and Technology (NIST) that would be used in the present invention to maintain secure data communications. Besides lattice encryption and decryption, quantum computer encryption is another type of encryption system that is of a type being constructed for the NIST that would be used in the present invention to maintain secure data communications between subscribers, subscriber devices, and subscriber human-like entities. The items indicated below brackets B1 describes the types of physical and digital content artifacts 18 a subscriber could provide to assist the business enterprise in maintaining and constructing personal emulation PDA 95-99 devices and personal human-like mechatronic, bio-mechatronic, and mechatronic systems. As shown near the bottom of FIG. 25, artifacts may include Egg and Sperm 83, Stem cells 84, stem cells 85, progenitor cells 8, genetic material (i.e., deoxyribonucleic acid (DNA) and ribonucleic acid (RNA)) 86 and storage 253, diary 87, academic records 88, medical records 89, biometrics 90, family photographs and videos 91, cellular phone records and data 92, social media records data 93 and other types of data, Internet search records and data 94, cognitive agents 302, computer bots 303, stem cell and pregenorator cells 8 information, and things. Artifact storage may be provided to store artifacts. Artifacts and information from artifacts will be used in constructing PDA's 95-99, and entities 5, 6, 7, 20, 21. Artifacts and information from artifacts will be used in constructing PDA's 300 and entities 5, 6, 7. Personal Digital Assistant (PDA) 300 systems include help robot 95, a holographic system 96, 290, a rotating led system (not shown), a smart audio speaker (not shown), a smart phone (not shown), a headgear 97, a cellphone with panoramic video 98, and a virtual panoramic system 99, and the like PDA systems. The PDAs will collect and archive information that is used to construct entities that replicate the subscriber 20 as part of the enterprise 1 effort. To achieve this the enterprise 1 may offer storage of artifacts 83 and to maintain an artifact 18, PDA 300, user/subscriber 2/5, 6, and 7 entity data, information and system as an enterprise service(s) for a subscriber to the enterprise 1. The items indicated below brackets list one computer processing and storage systems and second computer emulation systems for constructing and maintaining a personal emulation PDA devices and personal human-like mechatronic, bio-mechatronic, and mechatronic systems. For example, servers are operated by the business to store digital information from the subscriber and for engineering develop software, firmware, and hardware used by the business to provide support and products to the subscriber via the business described in FIG. 1, the fulfillment process in FIG. 2, and the cloud and shipping services shown in FIG. 3 of the present invention. The methodology the business provides to identify and collect CP data and NCC data is described in FIGS. 4-9c of the present invention. And FIGS. 11-26c illustrate virtual PDA systems and human-like entity systems that produce human content consume content that is needed by the business enterprise to emulate and maintain a subscriber's biological, mechatronic, and bio-mechatronic PDA devices and human-like entity systems. Arrows at left of the diagram indicate subscriber to business interaction points required throughout necessary to construct and maintain products and services during the lifecycle of the products and service provided. Typically, as depicted in FIGS. 1 and 25, a subscriber, user, agent, or recipient query (i.e., 2, 5, 6, 7, 21, 95-99) is serviced by the enterprise via the cloud by connecting to local enterprise fulfillment centers and the business architectures (i.e., 12, 13, 16, 21, 22-24, 35, 42) that address artifact, PDA, and entity requests.

Still referring to FIG. 25, the illustrations and text below bracket disclose the culmination of the effort of the human emulation business architecture which is to produce biological, mechatronic, and bio-mechatronic PDA devices, biological recipient entities 5, and human-like entities 6 an 7 that emulates a person's likeness and extends there being and survival long beyond what would be their natural death. In the present invention PDA devices, biological recipients, and human-like entities will have at their most basic level the functional capability of the most modern cellular phone built in to the design. The entity system embodiments described in FIG. 25 include the functionality described in FIGS. 4-10 in order to sense, record, and process information about a user for updating successor recipient 5 the entity 6 or 7 later use in constructing, training, and maintaining and an A.I. human-like parent and successor systems in accordance with and supported by the enterprise 1 and business architecture 2 of the present invention. Natural neural processing brain for a natural born human biological system 2 is illustrated in FIG. 1. Optionally, a recipient biological entity 5 has natural biological neural processing that operates on naturally sensed data derived from a parent recipient logging system or on transplanted material derived by a recipient bio-mechatronic or mechatronic entity. For example, a recipient biological recipient entity 5a may use visual senses and auditory senses to hear using head gear which enlightens the brain. In this example recipient entity 5a internalizes the information as at least one CP and NCC that constitutes a perception and memory within the biological recipient entity's 5a mind. But after the stimulation the headgear is removed and not permanent as depicted in recipient entity 5a. Still, further yet, a cloned recipient biological entity 5a may receive information derived by a recipient information in an immersive audio-visual system like a "videoroom" and internalizes that information as at least one CP and NCC that constitutes a perception and memory within the mind of biological recipient entity 5. Or for example, a recipient biological entity 5b may receive stem cells transplanted after undergoing manipulation in CRISPR in order to adapt the biological entity to a changing or hostile environment. Still further, the head of another being is transplanted onto a biological recipient entity 5b. The present invention teaches that an entity 5a may undergo at least one non-intrusive procedure that provide brain training information and entity 5b may undergo an intrusive procedures that provide transplanted material that has or is receptive to information derived from correlating surrounding environment and brain activity using A.I. equipped devices. Said information being derived from at least one a PDA or a self-reliant human-like entity 6 and 7. Wherein the biological entity 5a that receives the derived information is not required to always wear a bio-mechatronic device like required with biomechatronic entity 6a and 6b . As illustrated in FIGS. 1-3 and 25 the biological systems group 22 is the systems work group 35 that provides engineering and design 12 oversight in business architecture 16 of the enterprise 1 for biological self-reliant human-like entity 5 system embodiments. A principal difference between a naturally born person and a recipient being is that naturally born human being has no way of transferring his memory CP as NCC in natural reproduction, only genetic code reflective of himself or herself. In contrast the present invention provides a transformative system and method that facilitates the design, engineering, and production of embodiments that allow for the transfer of memory CP as NCC reflective of himself or herself to be transferred between recipient biological 5, biomechatronic 6, and mechatronic 7 entity systems using the disclosed technologies in the present invention. As illustrated in FIG. 6 the present invention results in making mankind more adaptable and resilient and opens new frontiers to mankind to operate in hostile environments, such as space exploration and colonization. And to overcome other human biological limitations, such as mortality due to life expectancy and disease.

Or for example in FIG. 25, in a bio-mechatronic entity 6 embodiment of the system, neural processing in the brain and artificial intelligence neural processing cooperatively and complementarily function together in the bio-mechatronic system 6 (6a or 6b). Biomechatronic system 6a, 106 includes an entity computer system 165 that includes a wearable headgear with a wearable head mounted display 239, support apparatus 240, and a wearable non-invasive brain activity sensing 177 and an invasive brain stimulation system 178 that operate to sense, log, record, process, derive, and operate upon the brain and brain data to derive NCC from CPs. An example of a wearable non-invasive brain activity sensing headgear 97a and stimulation system of a type like that is used in entity 6a is disclosed in U.S. Pat. No. 9,730,649 and other referenced related patents by Jepsen 177 and incorporated in full by reference into the present invention. Alternatively, a biomechatronic system 6b that includes an entity computer system 165 that includes a wearable headgear 97b with an invasive brain activity sensing and stimulation system that operates to sense, log, record, process, derive, and operates to derive NCC from CPs. An example of the invasive wearable system 178 includes that disclosed in a white paper by Elon Musk & Neuralink, entitled "An Integrated Brain-Machine Interface Platform 166 with Thousands of Channels", 16 Jul. 2019, by Neuralink™ Corporation), incorporated in full by reference into the present invention. As illustrated in FIGS. 1-3 and 25 the biomechatronic systems group 23 is the systems work group 35 that provides engineering and design 12 oversight in business architecture 16 of the enterprise 1 for biomechatronic self-reliant human-like entity 6 system embodiments like 6a and 6b.

And finally in FIG. 25, the mechatronic system 7 that includes an artificial neural network which conducts cognitive computing similar to a human. Hence, in the present invention the enterprise 1 system provides the business architectures 16 to facilitate a human 2, 5 to machine 6, 7; and machine 6, 7 to human 2, 5 transformations. An example of systems and methods used by a person who is supported by the business architecture in the present invention who uses a mechatronic entity configuration without a synthetic human like covering is described next to the designation 7a. And an example of systems and methods used by a person who is supported by the business architecture in the present invention who uses a mechatronic entity configuration with a synthetic human like covering that looks like at least one natural skin and hair is described next to the designation 7b. As illustrated in FIGS. 1-3 and 25 the biomechatronic systems group 24 is the systems work group 35 that provides engineering and design 12 oversight in business architecture 16 of the enterprise 1 for mechatronic self-reliant human-like entity 7 system embodiments like 7a and 7b.

Still referring to FIG. 25, basic attributes the human-like self-reliant entity 21 within the present invention include a conveyable computer system with a cognitive memory system and computer subsystems operated in real time to dynamically correlate neural network activity data with surrounding environment data akin to a human with a first computer subsystem conveyable. Entity 21 conveyable computer being compatible with a neural correlates of consciousness database stored in non-volatile computer memory 118 as the cognitive memory in the computer subsystem 165 that defines a taxonomy for the entity's perception of self and the environment. And said first computer subsystem including and compatible with the neural correlates of consciousness database operated upon by at least one biological neural network and artificial neural network that includes back propagation processes that iteratively and adaptively derive logic-based outcomes that improve results or achieve desired outcomes that are decided by said entity and determine said entity's activity. And said first computer subsystem including and compatible with said entity's sensor arrangement that operates to record and store in non-volatile memory self-sensing and surrounding image signatures, operates on those non-volatile memory of environment image signatures, operating on non-volatile memory of image signatures to formulate a plan based on the entity's internal operations in the external surrounding environment, and act with the intent to reach a goal based on the plan derived and shaped by the entity's overall design. Said first computer subsystem operates upon at least one neural network to derive neural correlates of consciousness from conscious percepts and subsequently to operate on those neural correlates of consciousness to make decisions as a self-reliant recipient system. The system also includes a second computer subsystem including a structural system that includes a support, actuator, and manipulator subsystem that operates with the mobility and dexterity akin to a human. And finally, the system 113, 165 includes a third computer subsystem including a rechargeable energy generation subsystem that operates akin to a human wherein said conveyable computer system and subsystems, energy generation, a structural system with actuator and manipulator subsystems are in communicating relationship and once initiated operate as a cohesive system akin to a human. It will be understood by those knowledgeable in the art that a bio-mechanical entity's survival may depend on biological processes due to the fact they wear out and may be irreplaceable. Preferably, a built-in telecommunication system and network is built into entities to improve entity survival.

FIG. 25, illustrates that the hardware for an entire independent human-like mechatronic entity 7a and 7b may be constructed using three-dimensional (3d) printing technology such as the three dimensional nano printer workstation 74 and the three dimensional printer 75. All materials necessary are available and may be used to construct PDA's and entity's using 3d printer technology to construct all components down to the nano scale in the present invention. For instance, neural circuitry can be constructed using nano hardware. A computer server 73 is used to store digital artifact 18, PDA 300, and/or entity 165 information or production data from the systems work groups 35 who focus on subscriber 20 related design and engineering and maintenance of products & services 68, data and information 69, and systems and applications 70 of engineering and design 12 and production 13 shown in FIGS. 1-3, and FIG. 25. Solar components to provide electrical energy components may also be constructed. And optical components to construct vision systems may also be constructed using a 3d nano printer. Additionally, firmware may be embedded the circuitry and function as artificial neural networks that allow the mechatronic system to make decisions and function independently once built. Examples of software that may be installed into a mechatronic system like that disclosed herein and mimic a person is a computerized unstructured visual learning computer network with a framework that is incorporated by reference into and compatible with embodiments hereby incorporated by reference in their entireties into the present application is Lichao Chen et al. (Lichao Chen, Sudhir Singh, of the Department of Electrical and Computer Engineering, University of California, Los Angeles, Calif. 90095; Thomas Kailath, and Vwani Roychowdhury of the Department of Electrical Engineering, Stanford University, Stanford, Calif. 94305) entitled "Brain-inspired automated visual object discovery and detection", published online Dec. 17, 2018, at www.pnas.org/cgi/doi/10.0173/pnas. 1802103115, b.) and "Supporting Information Appendix: Brain-Inspired Automated Visual Object Discovery and Detection to the same paper. As previously mentioned in the instant application, application Ser. No. 15/258,336, and parent CIP application Ser. No. 16/601,010 by the present inventors, and the Lichao Chen et al "Brain-inspired automated visual object discovery and detection", system may be designed into micro-electronic integrated circuits and chips that assist the human-like bio-mechanical system 6 and the human-like mechatronic system 7 process information and make decisions in the present invention. For example, U.S. Pat. No. 5,781,702, by Bassem A. Alhalabi, filed 7 Jun. 1995, and issued 14 Jul. 1998 entitled "Hybrid Chip-Set Architecture for Artificial Neural Network System" may process information in the historical relational database input into a parent being along with current real-world data from a surrounding environment. The independent mechatronic system 7 operates on both data sets for command and control itself. The system 7 hardware, firmware, and databases are designed and installed during system engineering and design as shown in FIG. 25. And may include devices, processes, and firmware of a type like that described by Alhalabi which are incorporated into the present invention by reference include the follow to the enterprise System Engineering & Design 12 and Production 13 Groups 23 and 24 in designing and constructing entity 6 and 7 system embodiments: WO US U.S. Ser. No. 10/262,356B2 Bruce L. Davis Digimarc Corporation, entitled "Methods and arrangements including data migration among computing platforms, e.g. through use of steganographic screen encoding", Priority 2014 Aug. 30, Filed 2017 Feb. 8, Granted 2019 Apr. 16, Published 2019 Apr. 16; "Intel's New 49 qubit Quantum Chip and Neuromorphic Chip" by Intel's CES 2018 keynote focused on its 49-qubit quantum computing chip and AI self-learning chip for mobile platforms, 9 Jan. 2018; Published as US2011/0119214 A1, priority date 2009 Nov. 18, Publication date 2011 May 19, Assignee: International Business Machines Corporation, entitled "Area efficient neuromorphic circuits"; CN102831476A, 2012-Dec.-19, Publication, 2015-Feb.-18 Application granted, 2015-Feb.-18, Publication as CN102831476B "Pattern detecting device and pattern detecting method for pulse neural network"; U.S. Pat. No. 8,892,487 B2, Filed 2010-Dec.-30, Published 2014-Oct.-16, "International Business Machines Corporation, "Electronic synapses for reinforcement learning"; U.S. Pat. No. 8,918,351 B2, 2012-Jul.-30 , 2014-Dec.-23, International Business Machines Corporation, "Providing transposable access to a synapse array using column aggregation"; U.S. Pat. No. 9,218,564 B2, 2012-Jul.-30, 2015-Dec.-2022, International Business Machines Corporation, "Providing transposable access to a synapse array using a recursive array layout"; US2018/0285290 A1 , 2017-Mar.-30, 2018-Oct.-4, Futurewei Technologies, Inc. "Distributed and shared memory controller"; U.S. Ser. No. 10/769,080 B2, 2018-Mar.-30, 2020-Sep.-8, Futurewei Technologies, Inc.,Distributed and shared memory controller"; Published as U.S. Ser. No. 10/628,732 B2 on 2020 Apr. 21, entitled "Reconfigurable and customizable general-purpose circuits for neural networks"; U.S. Pat. No. 9,245,223 B2016-01-26 "Unsupervised, supervised and reinforced learning via spiking computation"; and U.S. Pat. No. 8,812, 415B22014-08-19, Neuromorphic and synaptronic spiking neural network crossbar circuits with synaptic weights learned using a one-to-one correspondence with a simulation"; CN106104585A entitled "Analog signal reconstruct and identification via threshold modulated" by R.M.and V. H., 2015 Feb. 27, Priority to PCT/US2015/017910 A1; and CN108362284A entitled "A kind of air navigation aid based on bionical hippocampus cognitive map", 2018 Jan. 22, which teaches robot ANN control and prediction activity thresholds system for robot construction and remote repair; Priority to CN201810057721A which teaches a robot navigational system; CN108304767A, entitled "Human action's intention assessment training method based on more brain area cooperated computings" by Chinese Inventors, granted 2020 Jun. 30, which teaches human action's intention assessment training method based on more brain area cooperative computing; and U.S. U.S. Pat. Appl. 2007/0198444, 23 Aug. 2007, which teaches a robot how to determine whether a human is present or absent in the surrounding environment.

Still further, the following enabling applications and patents are hereby incorporated by reference in their entireties into the present invention: are incorporated into the cognitive computer processing systems by reference to construct PDA's 300 and entities 6 and 7 that respond to the surrounding environment: "Imitation learning with spiking neural networks and real-world devices" by Harald Burgsteiner, Department of Information Engineering, InfoMed/

Health Care Engineering, Graz University of Applied Sciences, Eggenberger Allee 11, A-8020 Graz, Austria, in Engineering Applications of Artificial Intelligence, Published by ELSEVIER, and online from ScienceDirect, 18 Jul. 2006; U.S. Pat. No. 7,430,546 B1, by Roland Erwin Suri, entitled "Applications of an Algorithm that Mimics Cortical Processing", dated 30 Sep. 2008; U.S. Pat. No. 9,015,093 B1, by Michael Lamport Commons, entitled "Intelligent Control with Hierarchical Stacked Neural Networks" 21 Apr. 2015; U.S. Pat. No. 9,338,493 B2, entitled "Intelligent Automated Assistant for TV User Interactions" by Apple Inc., Marcel Van Os et al., 10 May 2016; U.S. Pat. No. 9,426,598 B2, "Spatial Calibration of Surround sound Systems Including Listener Position Estimation" 23 Aug. 2016; U.S. Pat. No. D882,548 entitled "Intelligent Speaker" by Shuai Guo, dated 28 Apr. 2020; U.S. Pat. No. D883,966 entitled Wireless Signal Transmission Device, dated 12 May 2020; U.S. Pat. No. D885,367 entitled "Intelligent Speaker", by Guo et al., dated 26 May 2020; and U.S. Pat. Appl. US 2014/0310595 A1, by SRI International, Girish Acharya et al., filed 24 Jun. 2014 which provides a computing system of a type that can be adapted to the present invention.

Still Referring to FIG. 25 and constructing human-like entity's shown as 7a and 7b in the present invention. Human-like robot movement and dexterity and balance of a type adopted by reference into the present invention includes like the Atlas robot manufactured by Boston Dynamics, Waltham, Mass., and Valkyrie from NASA, and Skybot F-850 from Roscomos, Moscow, Russia, which have bipedal locomotion and can be entirely manufactured using a combination of 3D nano and conventional 3D meta-material printing techniques and technology reference herein. Muscles of a type that are of a type that may be used to operate entities in the present invention adopted by reference include those in U.S. Pat. Appl. US2006/0041183A1 Richard J. Massen et al., Published 2006 Feb. 23, entitled "Electromechanical machine-based artificial muscles, biovalves and related devices"; WO US AU U.S. Pat. No. 6,379,393 B1 by Constantinos Mavroidis, of Rutgers, The State University Of New Jersey, Published 2002 Apr. 30, entitled "Prosthetic, orthotic, and other rehabilitative robotic assistive devices"; wherein all references in this specification are hereby incorporated by reference in their entireties into the present application. An animatronics character is built around an internal supporting frame, usually made of steel. Attached to these "bones" are the "muscles" which can be manufactured using elastic netting composed of styrene beads. The frame provides the support for the electronics and mechanical components, as well as providing the shape for the outer skin. The "skin" 65 of the figure is most often made of foam rubber, silicone or urethane poured into molds and allowed to cure. To provide further strength a piece of fabric is cut to size and embedded in the foam rubber after it is poured into the mold. Once the mold has fully cured, each piece is separated and attached to the exterior of the figure providing the appearance and texture similar to that of "skin" By measuring and recording the facial features synthetic skin and hair for an entity 7b. The synthetic skin 65, 305, 106, 169 may be positioned over and adhered to the entity's framework and synthetic muscles for a realistic look. In the present invention the entity may incorporated the most advanced animatronic features and technology available. Examples include but are not limited to "Erica", a Japanese conversational robot with human looking facial features. And "Shaman" a Disney™ animatronic robot with natural dexterity of body and appendages, voice, and look. Optical sensors are integrated into the eyes and audio microphones for the ears and voice synthesis systems into the mouth for a voice and set into synthetic skin for a more human-like appearance in construction of the 7b system. Additionally, force feedback sensors familiar to those in the art may be embedded at least in the synthetic skin or just below the synthetic skin to sense pressure, heat, and cold. Electromagnetic pulse, radiation, and electromagnetic activities, and pressure shielding, and protection systems also may be also be built into the covering of the human-like entity in the present invention. The animatronic features will be communicatively linked by the human-like entity's computer processing and circuitry which will include artificial neural network algorithms that drive the animatronic actions of the human-like entity 5, 6, 7. Audio-visual capabilities like that in the newest cell phones and technology along with components and art described above facilitate construction of a human-like sentient entity described in the present invention. Providing these and other components to facilitate construction are part of the human emulation enterprise system and method for maintaining and transitioning humans to a supplementary adaptable sentient human-like self-reliant entity 6a, 6b, 7a, 7b. As illustrated in FIG. 6, the enterprise system 1 exists in the local environment 33, world 142, and universe 143 where remote servers 198 and subscribers 20b will exist. Fulfillment centers 42 may exist in deep space and communicate back to earth 148 via communication satellite(s) 153. And additionally, spaceships may include 3d printers and materials that are operated upon to maintain and produce PDA and entities 2, 5, 6, 7, 100, 113, 165 and the like. In the present invention entities and spacecraft 146 may be powered by a fusion reactor 147 that generates electrical power.

FIG. 26a is a diagram that illustrates the benefit of a human-like help PDA, robot, or human-like entity derived in accordance with the present invention suited for the hostile environment like space. The enterprise system 1 exists in the local environment 33, world 142, and universe 143 where remote servers 198 and subscribers 20, 21 will exist. Fulfillment centers 42 may exist in deep space and communicate back to earth 148 via communication satellite(s) 153. And additionally, spaceships may include 3d printers and materials that are operated upon to maintain beings 2, and produce PDA 95-99, recipient entities 5a, 5b, and entities 6a, 6b, 7a, 7b, 100, 113, 165 and the like. Additionally, entities 2, 5, 6, 7, and PDAs 95-99 and spacecraft may be integrated in at least one a borne, wireless, wired, and communicative relationship with at least one systems such as a DNA/RNA embedded data system 253, CRISPR system 146, a cryogenic system 258, a transplant 258, or a prosthetic 259 for operation in order facilitate adaptation in a changing and/or hostile environment 318 such as space. For example, see "Genetic and activity-dependent mechanisms underlying interneuron diversity" by Brie Wamsley and Gord Fishell, in Nature Reviews/Neuroscience, Volume 18 May 2017 by 2017 Mamillian Publishers Ltd.; and U.S. Pat. No. 9,101,279 B2 page 101-102, lines 51-17, FIG. 47 X and Y, which is adopted by reference into the present application. In the present invention fulfillment centers 42 may be located in space on spacecraft 146 and planets 306 as part of the enterprise 1 architecture(s) 16. And that the architecture 16 will include a telecommunication system and network that incorporates communication satellites 153 and spacecraft 146 connects each subscribers 20 and systems of the enterprise 1 commutatively connected. Additionally, in the present invention entities and spacecraft 146 are powered by a fusion reactor 147 that generates electrical power. One benefit is that a human-like help like PDA, robot, or human-like entity 165 comprising a bio-mechatronic and mechatronic system may be constructed to survive much longer than a human and because the human-like help like PDA, robot, or human-like entity possesses the mental capabilities to learn and adapt in space. And that construction and maintenance of a human-like PDA or entity is supported by an Enterprise Architecture consistent with the present invention. FIG. 26a depicts the spaceship 146 and inter planetary travel. A straight dashed lines 152 represents the path to a distant planet 149 and a curved dashed line 151 represents the trajectory around a planet from a launch from earth 148 and landing on a distant planet 306. FIG. 26b illustrates the benefits of a human-like mechatronic system 7a and 7b that can survive in space where oxygen is scarce and by using at least one of a solar energy generation system or a fusion reactor electrical energy generation system to recharge itself when in outer or deep space. In the present invention the solar cell, or photovoltaic cell 319, comprises a conventional or more elaborate covering that consists of an electrical device incorporated that converts the energy of light directly into electricity by the photovoltaic effect, which is a physical and chemical phenomenon. In FIG. 26a solar cells form a solar array 320 comprising a plurality of photovoltaic cells 319 that generate electrical energy to power electrical devices on the spaceship that may include the spaceship 146, help robot 95, human-like entities 6 or 7. FIG. 26b illustrates a human-like entity electrical self-charging and data docking station 145, like that described in U.S. 2021/0105435 A1 that connects to a subscriber 20 such as a human-like entity 6, 7, or PDA's 300. FIG. 26c depicts a spaceship 147 that the human-like robot 95 may also plug into for data, command, control, communications, and electrical power. A fusion system adapted by reference in its entirety into the present invention that is compatible for generating electrical power for powering a spaceship and integration into the design of a human-like independent entity system 7 for terrestrial and space travel compatible and consistent with the present invention is of a type like the Lockheed Martin Compact Fusion Reactor (CFR) described in U.S. Pat. No. 9,947,420 B2, entitled "Magnetic Field Plasma Confinement for Compact Fusion Power", filed 2 Apr. 2019, by Thomas John McGuire, and issued 17 Apr. 2018 which is hereby incorporated by reference in their entireties into the present application.

Finally, in conclusion, it will be understood by those skilled in the art that robots may be constructed for docking with drones or shipping for delivery by themselves to and from a fulfillment center for delivery and maintenance. And that the scale of and nature (i.e., integration with a spaceship or other system or device) in the form of a PDA and human-like entities may vary in different environments in accordance with the human-like emulation enterprise system and method in accordance with the present invention. For example, see Pat. App. US20180300676A-20181018-D00000, by CH inventor; and US20180300676A1, by Kevin Person, Marble Robot, Inc., entitled "Delivery robot and method of operation", 18 Oct. 2019; and U.S. Pat. No. 9,101,279 B2, FIGS. 43-47, by Ritchey et al, dated Aug. 11, 2015, by the present applicants. Wherein all the above cited references, applications, and patents are hereby incorporated by reference in their entireties into the present invention.

Those skilled in the art will know or be able to ascertain given the disclosure herein using no more than routine experimentation, many equivalents to the specific embodiments of the invention described herein. These and all other equivalents are intended to be encompassed by the following claims.

Having thus described various embodiments of the invention, what is claimed as new and desired to be protected by Letters Patent include the following:

1. An enterprise system comprising:
   a business architecture that transitions, transforms, and maintains at least one subscribing self-reliant biological human being, biomechatronic self-reliant entity, and self-reliant mechatronic entity of the enterprise system into at least one human being, biomechatronic self-reliant entity, and self-reliant mechatronic entity that receives at least one artifact;
   a business architecture of at least one subscribing human being, biomechatronic self-reliant entity, and self-reliant mechatronic entity of the enterprise collecting, logging, and processing at least one artifact for use in emulating at least one subscribing human being, biomechatronic self-reliant entity, and self-reliant mechatronic entity;
   a business architecture-of said subscribing human being, biomechatronic self-reliant entity, and self-reliant mechatronic entity translating at least one of said artifacts into at least one personal digital assistant device, biological system, biomechatronic system, and mechatronic system that is a successor or predecessor of a human-like self-reliant entity;
   a business architecture including a hybrid annuity life-cycle financial management system that administers a life-cycle hybrid annuity life-cycle instrument that transforms at least one a subscribing human, biomechatronic self-reliant entity, and mechatronic self-reliant entity in-order-to at least one survive, modify, and transform itself.

2. The enterprise system according to claim 1 wherein the hybrid annuity life-cycle financial management system for sustaining a predecessor and successor of a human-like self-reliant entity comprises:
   a hybrid annuity life-cycle instrument for a biological, biomechatronic, and mechatronic entity that includes a hybrid insurance contract between at least one subscriber, subscribers annuitant, and enterprise system; wherein the enterprise is capable of functioning as the subscriber's annuitant and actualizing said hybrid annuity life-cycle claim; said subscriber purchasing said hybrid annuity to pay said enterprise a single lump sum or a series of payments to at least one subscriber and enterprise system to interchangeably transform said subscriber electing to at least one maintain, modify, and change at least one predecessor and successor to at least one biological, biomechatronic, and mechatronic human-like self-reliant entity state when said annuitant's claim is approved and actualized to at least one maintain, modify, and change said entity to a different biological, biomechatronic, and mechatronic human-like self-reliant entity state; said annuitant and issuant being able transact said subscription and annuity claim by at least one over a telecommunications system, such as the internet, and in person; and
   an enterprise system including a business architecture that includes the capability to operate upon said hybrid annuity to perpetuate a life-cycle financial management system to interchangeably transform said entity when at least one predecessor and successor of at least one biological, biomechatronic and mechatronic entity elects to activate said subscriber hybrid annuity claim and said annuitant approves and actualizes said claim in accordance with the annuitants hybrid annuity life-cycle contact; said annuitant and enterprise having an internet telecommunication system to transact and assist in software and firmware updates of said hybrid annuity; said subscriber and annuitant including the capability to transport the subscriber to and from an enterprise medical treatment facility and engineering service facility when required for honoring said hybrid annuity claim; at least one said predecessor and successor procedure enabled by a business architecture with at least one medical treatment facility and engineering service facility required to actualize said hybrid annuity claim; implementing treatment and service to said subscriber for at least one store artifacts, update PDAs, diagnosis, design, test, conduct simulation, provide stimulation, interface with, replacement, repair, construction, production, installation, manufacturing, and evaluation using the medical and engineering facilities, systems, and procedures; and said facilities, systems, and procedures to at least one upload and download using at least one non-invasive and invasive medical procedure into at least one predecessor and successor of at least one biological, biomechatronic and mechatronic entity.

3. The enterprise system according to claim 1 wherein:

a hybrid life-cycle financial management system includes
  a hybrid annuity life-cycle instrument activated to administer at least one firmware, hardware, or biological implementation procedure to at least one deliver and transform at least one bot, nanobot, agent, and material to transform at least one subscribing human, biomechatronic self-reliant entity, and self-reliant mechatronic entity;

said nanobot comprising at least one biological nanobot, biomechanical nanobot, and a mechatronic nanobot;

said transform performed to a subscribing human, biomechatronic self-reliant entity, and self-reliant mechatronic entity when the entity's survival is in jeopardy in-order-to at least one survive, modify, and to achieve a desired effect.

4. The enterprise system according to claim 1 wherein a hybrid annuity life-cycle instrument enables at least one diagnosis, measuring, and modifying the self-governance of a predecessor human and successor human-like self-reliant entity comprising:

a cognitive computer processing system that includes metadata that comprises a set of data that describes and gives information on neural activity in a brain associated with perceptions and activity of a predecessor human and successor human-like entity, processing data and information recorded in a surrounding environment about said predecessor human and successor human-like entity, and an internal file structure for processing recorded and processed sensed neural activity and surrounding environment data and information maintained as non-volatile memory within said automated computer processing system; said automated computer processing system operations selectively including artificial intelligence with backpropagation and machine learning at least one implemented onboard said entity or from a remote location;

a first automated computer processing subsystem operating a user interface configured to receive a plurality of input streams of sensor data representing sensor readings over a range of entity states of at least one successor and of a predecessor biological, biomechatronic, and mechatronic human-like self-reliant entity during the life-cycle of said interchangeably transposable predecessor or entity; said data and information recorded and processed by said computer processing system operating to provide at least one successor and predecessor data and information derived from at least one brain activity sensing system and recording system of a biological and biomechatronic system and at least one an artificial neural network system of the biomechatronic and mechatronic human-like self-reliant entity derived by said computer processing system; said computer operating on said neural network activity within at least one the brain of a biological and biomechatronic system or the artificial neural networks of the biomechatronic and mechatronic human-like self-reliant entity; at least one user interface configured to receive a plurality of input streams of surrounding environment sensor data about at least one the successor and predecessor biological, biomechatronic, and mechatronic human-like self-reliant entity; said sensor data including time and place recorded; at least one automated processor, configured to correlate the relationships between a plurality of streams of at least one successor and predecessor biological, biomechatronic, and mechatronic human-like self-reliant entity and surrounding environment sensor data; said correlated data streams representing sensor readings recorded and processed in an automated cognitive computer resulting in a relational database that is stored in non-volatile memory that defines associations of how a successor and predecessor entity perceives and acted in a given environment; said computer processing system including an interface device operated to interchangeably transform neural activity data of said subscribing predecessor and successor entity to a desired outcome based on data derived by another automated computer processing system;

a second automated computer processing subsystem performing an operation on many databases derived other subscribers using a similar automated computer processing system; said correlated data streams representing sensor readings recorded and processed in an automated cognitive computer resulting in a second cohort relational database that is stored in non-volatile memory that defines associations of many successor and predecessor entity perceives and acted in a given environment; said second automated computer processor configured to calculate the aggregated statistical properties of plurality of streams of data representing readings over the range of states of many other cohort successor and predecessor entity's perceptions and actions, social network data and information, and search engine data and information and determine the statistical norm for said aggregated population of at least one successor and predecessor biological, biomechatronic, and mechatronic human-like self-reliant entity operating in a similar surrounding environment at a given time and place;

a third automated computer processing subsystem including at least one correlation and comparator processing system that performs that calculates the statistical norm of a plurality of statistical properties that reliably distinguish between a normal state and aggregate of the at least one perception, idea, and activity of at least one other individual or cohort; said non-volatile memory configured to be stored and operated upon by said third computer processing system to determine the statistical norm;

a fourth automated computer processing subsystem with a brain to computer interface system acting on neural activity within the natural brain of at least one biological and biomechatronic system and artificial neural network to modify the neural activity to achieve a desired outcome on at least one predecessor human and successor human-like self-reliant entity; said modification enabled by performing at least one invasive and non-invasive treatment to modify subscriber neural cells; said neural cells for treatment being located during the first automated computer processing subsystem operations that identify the brain cells responsible for conscious perceptions and neural correlates of consciousness of the subscribing patient and during the second and third automated computer processing subsystem operations that define deviations of subscriber cells that represent subscriber perceptions that are different from other individuals, cohorts, doctrine, policies, regulations, statues, procedures and alternative designs.

5. The enterprise system according to claim 1 wherein the hybrid life-cycle financial management system includes a hybrid annuity instrument activated to enable teleportation method for the transformation and modification of a transposable human-like self-reliant entity to transform at least one a subscribing human, biomechatronic self-reliant entity, and self-reliant mechatronic entity when the subscriber's survival is in jeopardy in order to at least one survive and to achieve a desired effect.

6. The enterprise system according to claim 1 wherein:
a hybrid life-cycle financial management system operates to sustain a predecessor and successor of a human-like self-reliant entity by operating a life-cycle hybrid annuity instrument; said hybrid annuity being financed at least one partially or wholly by an offset to compensate at least one subscriber, subscriber's agent, enterprise, public, and private entity; said offset at least one directly or indirectly providing benefit to at least one said subscriber, subscriber's agent, enterprise, public, and private entity in exchange to the issuant of the offset to at least one reduce the environmental impact of usage of a natural resource, emission of carbon dioxide into the atmosphere, a scarce commodity, and address system and design engineering issues, and personal, cultural, societal, political, economic, geospatial injustice and inequality resulting from at least one human and human-like entity activity of at least one subscribing successor and predecessor of a biological, biomechatronic, and mechatronic entity; said offset being justified by the impact caused by weighing at least one the cost, risk, and benefit of the successor and predecessor biological, biomechatronic, and mechatronic entity compared to the impact caused by the transformation of at least one successor biological, biomechatronic and mechatronic entity.

7. The enterprise system according to claim 1 wherein:
a hybrid life-cycle financial management system initiated for sustaining a predecessor and successor of a human-like self-reliant entity comprises an artifact and personal digital assistant that includes at least one data and information derived from a life-logging system that at least one collects, processes, and operates upon on at least one internal and external sensing monitoring system, and correlation system, machine learning, interface system, cognitive computer processing system, computer storage system with associated cognitive computing systems, relational databases, neural networks with back propagation, and simulations related to and generated as conscious perceptions that equate neural correlates of conscious related to a subscribing human, biomechatronic self-reliant entity, self-reliant mechatronic entity and personal digital assistant systems that are enabled by activation of the said life-cycle hybrid annuity system of said enterprise system to enable transformation from said subscribing predecessor and successor human, biomechatronic self-reliant entity, and self-reliant mechatronic entity sustainment, maintenance, and management.

8. The enterprise system according to claim 1 includes:
a life-cycle hybrid annuity financial management system for transposable transformation of a predecessor and successor human-like self-reliant entity;
a cognitive computer with machine learning capabilities operating to perform requirements-based automated correlation of at least one subscriber based artifacts and personal digital assistance information that designs an entity by operating said cognitive computer with machine language capabilities that performs requirements-based capability design based on derived data using the Joint Capabilities Integration and Development System (JCIDS) guidance; said computer operating on said JCIDS methodology to determine the optimal capabilities to construct said human-like entity given key performance parameters and key system attributes that include intellectual, emotional, and physical requirements; determining said entity requirements of the entity by conducting statistically analysis of the sensing, measuring, and weighting of the neural activity of required by a human-like biomechatronic and mechatronic human-like entity that stimulates action potentials in at least one brain of a biomechatronic entity and of at least one artificial neural network of a biomechatronic entity and mechatronic system; said sensing, measuring, and weighting action potentials measured using a brain activity sensing system in a biomechatronic system and said sensing, measuring, and weighting action potentials at least one mimicked and enhanced in a biomechatronic and mechatronic entity attributes in in the artificial neural networks with backpropagation with firmware and hardware to facilitate learning and communication; said biological and electronic neural networks communicating together by brain to machine and machine to brain interface; said interface including image and pattern recognition systems that take sensed and telecommunicated data input for analysis by the entity from the surrounding environment about the entity; said input sources including input internal to the entity, from the immediate entity surrounding environments, and from entity remote databases to facilitate deep learning and communication sources including social media and search engines; said entity including a mobile telecommunication systems that receive local and remote wirelessly communicated surrounding environment information; said associated enterprise design, medical and engineering systems including the capability to test and validate the quality of said associated predecessor and successor biological, biomechatronic, mechatronic human-like self-reliant entity as an avatar in a virtual simulation or as a help-robot; said entity including the capability to remain an entity with at least one without hardware or firmware that at least one makes the entity not sentient or activates sentient; and
incorporating key system attributes that include: a physical framework that includes Boston Dynamics® bipedal robot stabilization, guidance system, center of gravity, dexterity, and mobility; an intellectual framework of the collision avoidance and navigation and processing of at least one a Tesla® Dojo® Chip and Intel® 12$^{th}$ gen CPUs for incorporation in order to facilitate a general purpose entity; and an intellectual framework that includes an animatronic system like that of Erica, a Japanese chat robot, with natural looking human facial and other body features; and the emotional framework including computer systems and methods that uses data analytics to characterize joint statistical properties that distinguishes between the normal state of the system and variance of a predecessor and successor entity in order to facilitate the measuring and modifying the neural structure for self-governance of individual and cohorts in order to facilitate an optimal design solution for at least one a biomechatronic and mechatronic system occupying a required environment; wherein said hybrid annuity is initiated to optimize the ontogeny in the design of at least one human-like biomechatronic and mechatronic entity.

9. The enterprise method comprising:

initiating a subscriber relationship between at least one a subscribing human, biomechatronic self-reliant entity, and mechatronic self-reliant entity and an enterprise system with a business architecture with a hybrid life-cycle financial management system that administers a hybrid annuity instrument that sustains at least one a subscribing human, biomechatronic self-reliant entity, and mechatronic self-reliant entity when the entity;

transitioning, transforming, and maintaining at least one subscribing human being, biomechatronic self-reliant entity, and self-reliant mechatronic entity into at least one an altered human being, biomechatronic self-reliant entity, and self-reliant mechatronic entity by operating an enterprise system with a business architecture for transitioning, transforming and maintaining a human being, biomechatronic self-reliant entity, and self-reliant mechatronic entity by modifying the subscriber's neural network;

collecting, logging, and processing at least one artifact related to relational correlated data and metadata derived user's perception of life-experiences in the surrounding environment and neural network activity for use in emulating at least one subscribing human being, biomechatronic self-reliant entity, and self-reliant mechatronic entity by operating an by operating a enterprise system with a business architecture for collecting, collecting, logging, and processing at least one artifact to derive data;

translating said derived data and metadata to at least one invasively or non-invasively impact and input derived data into the at least one biological and artificial neural network of at least one subscribing human being, biomechatronic self-reliant entity, and self-reliant mechatronic entity to facilitate emulation of at least one subscribing predecessor or successor human being, biomechatronic self-reliant entity, and self-reliant mechatronic entity that is at least one transitioning, transforming, and maintaining said subscribing human being, biomechatronic self-reliant entity, and self-reliant mechatronic entity by incorporating a said enterprise system with a business architecture tailored to at least one assist and change the state of at least one subscribing self-reliant biological human being, biomechatronic self-reliant entity, and self-reliant mechatronic entity;

operating a business architecture with a hybrid life-cycle financial management system that administers the hybrid annuity instrument to sustain at least one a subscribing human, biomechatronic self-reliant entity, and mechatronic self-reliant entity in order to at least one help said subscribing human, biomechatronic self-reliant entity, and mechatronic self-reliant entity survive and improve itself and others.

10. An enterprise method according to claim 9 wherein the hybrid annuity life-cycle financial management system operates to transform at least one subscribing predecessor and successor of a human-like self-reliant entity by:

operating a hybrid annuity instrument for at least one subscribing biological, biomechatronic entity, and mechatronic entity that comprises hybrid insurance contract between at least one subscriber, subscribers annuitant, and enterprise system; wherein the enterprise is capable of functioning as the subscriber's annuitant and actualizing said hybrid annuity claim; said subscriber purchasing said hybrid annuity to pay said enterprise a single lump sum or a series of payments to at least one subscriber and enterprise system to interchangeably transform said subscriber electing to at least one maintain, modify, and change at least one predecessor and successor of at least one biological, biomechatronic, and mechatronic human-like self-reliant entity state when said annuitant's claim is approved and actualized to at least one maintain, modify, and change said subscriber; said annuitant and issuant being able transact said subscription and annuity claim over the internet or in person; and operating an enterprise system including a business architecture that includes the capability to operate upon said hybrid annuity to perpetuate a life-cycle financial management system to interchangeably transform said subscriber state when at least one predecessor and successor of at least one biological, biomechatronic and mechatronic subscriber elects to activate said subscriber hybrid annuity claim and said annuitant approves and actualizes said claim; said annuitant and enterprise having an internet telecommunication system to transact assist in software and firmware updates of said hybrid annuity; said subscriber and annuitant including the capability to transport the subscriber to and from an enterprise medical treatment facility and engineering service facility when required for honoring said hybrid annuity claim; at least one said predecessor and successor procedure enabled by a business architecture with at least one medical treatment facility and engineering service facility required to actualize said hybrid annuity claim; implementing treatment and service to said subscriber for at least one care, diagnosis, design, testing, simulation, stimulation, replacement, repair, construction, production, installation, manufacturing, and evaluation using the medical and engineering facilities, systems, and procedures; and said facilities, systems, and procedures to at least one upload and download applying at least one non-invasive and invasive procedure to transform at least one subscribing predecessor and successor of at least one biological, biomechatronic and mechatronic entity.

11. Enterprise method according to claim 9 comprising:
initiating said hybrid annuity to enable the measuring and modifying the self-governance of a predecessor human and successor human-like self-reliant entity comprising;
operating a cognitive computer processing system that includes that comprises metadata that comprises a set of data that describes and gives information on neural activity in a brain associated with perceptions and activity of a predecessor human and successor human-like entity, processing data and information recorded in a surrounding environment about said predecessor human and successor human-like entity, and an internal file structure for processing recorded and processed sensed neural activity and surrounding environment data and information maintained as non-volatile memory within said automated computer processing system; said automated computer processing system operations selectively including artificial intelligence with backpropagation and machine learning at least one implemented onboard said entity or from a remote location;
operating first automated computer processing subsystem with a user interface configured to receive a plurality of input streams of sensor data representing sensor readings over a range of entity states of at least one successor and of a predecessor biological, biomechatronic, and mechatronic human-like self-reliant entity during the life-cycle of said interchangeably transposable predecessor or entity; said data and information recorded and processed by said computer processing system operating to provide at least one successor and predecessor data and information derived from at least one brain activity sensing system and recording system of a biological and biomechatronic system and at least one an artificial neural network system of the biomechatronic and mechatronic human-like self-reliant entity derived by said computer processing system; said computer operating on said neural network activity within at least one the brain of a biological and biomechatronic system or the artificial neural networks of the biomechatronic and mechatronic human-like self-reliant entity; at least one user interface configured to receive a plurality of input streams of surrounding environment sensor data about at least one the successor and predecessor biological, biomechatronic, and mechatronic human-like self-reliant entity; said sensor data including time and place recorded; at least one automated processor, configured to correlate the relationships between a plurality of streams of at least one successor and predecessor biological, biomechatronic, and mechatronic human-like self-reliant entity and surrounding environment sensor data; said correlated data streams representing sensor readings recorded and processed in an automated cognitive computer resulting in a relational database that is stored in non-volatile memory that defines associations of how a successor and predecessor entity perceives and acted in a given environment; said computer processing system including an interface device operated to interchangeably transform neural activity data of said subscribing predecessor and successor entity to a desired outcome based on data derived by another automated computer processing system;
operating a second automated computer processing subsystem and performing many operations on databases derived other subscribers using a similar automated computer processing system; said correlated data streams representing sensor readings recorded and processed in an automated cognitive computer resulting in a second cohort relational database that is stored in non-volatile memory that defines associations of many successor and predecessor entity perceives and acted in a given environment; said second automated computer processor configured to calculate the aggregated statistical properties of plurality of streams of data representing readings over the range of states of many other cohort successor and predecessor entity's perceptions and actions, social network data and information, and search engine data and information and determine the statistical norm for said aggregated population of at least one successor and predecessor biological, biomechatronic, and mechatronic human-like self-reliant entity operating in a similar surrounding environment at a given time and place;
operating a third automated computer processing subsystem which includes at least one correlation and comparator processing system that performs that calculates the statistical norm of a plurality of statistical properties that reliably distinguish between a normal state and aggregate of the at least one perception, idea, and activity of at least one other individual or cohort; said a non-volatile memory configured to be stored and operated upon by said third computer processing system to determine the statistical norm;
operating a fourth automated computer processing subsystem with a brain to computer interface system acting on neural activity within the natural brain of at least one biological and biomechatronic system and artificial neural network to modify the neural activity to achieve a desired outcome on at least one predecessor human and successor human-like self-reliant entity; said modification enabled by performing at least one invasive and non-invasive treatment to modify subscriber neural cells; said neural cells for treatment being located during the first automated computer processing subsystem operations that identify the brain cells responsible for conscious perceptions and neural correlates of consciousness of the subscribing patient and during the second and third automated computer processing subsystem operations that define deviations of subscriber cells that represent subscriber perceptions that are different from other individuals, cohorts, doctrine, policies, regulations, statues, procedures and alternative designs.

12. The enterprise method according to claim 9 comprising:
operating the enterprise's business architecture's hybrid life-cycle financial management system to activate a subscriber's life-cycle hybrid annuity to enable a procedural transformation of a subscriber and administering at least one a firmware, hardware, and material implementation of at least one bot and nanobot to the subscriber;
administering at least one firmware and hardware implementation of at least one bot and nanobot by implementing at least one bot and nanobot into a predecessor and successor biological, biomechatronic, and mechatronic system; said predecessor and successor biological, biomechatronic, and mechatronic system being a subscriber of the enterprise that includes a business architecture that enables life-cycle transformation between a biological, biomechatronic, and mechatronic state of existence;

transforming of a subscriber by delivering at least one firmware, hardware, and material implementation of at least one bot and nanobot; said nanobot including at least one biological nanobot derived from a living stem cell from a successor or predecessor biomechatronic nanobot, xenobot nanobot, biomechatronic nanobot, and mechatronic nanobot; said nanobot at least one established onto, within, or integrated into the surface of the subscriber, or alternatively, introduced by at least one placement, injection, transplant, and aerosol procedure implemented by said enterprise medical treatment facility and engineering service facility to the subscriber; said respective type of nanobot respectively transforming said subscriber by at least one reproducing, transporting materials, constructing, or effecting the subscriber to achieve transformation of the subscriber; administering said bot using least one nanobot and xenobot that serves to transport materials that are subsequently joined together that form at least one the natural material, tissue, and organ, or system or the synthetic material, component and system-of-systems, or system that form said subscribing entity;

enabling at least one said bot and nanobot to transform said subscribing predecessor and successor entity using said business architecture with medical treatment facility and engineering service to actualize said a hybrid annuity claim; said service implementing a treatment of at least one care, diagnosis, design, testing, replacement, repair, construction, production, installation, manufacturing, testing, and evaluation using the medical and engineering facilities, systems, and procedures; said facilities, systems and procedures to at least one upload and download at least one said bot; said treatment of at least one bot and nanobot system of at least one predecessor and successor entity by at least one biological, biomechatronic and mechatronic entity enabling subscriber entity transformation.

13. The enterprise method according to claim 9 comprising:

initiating said hybrid annuity to enable a teleportation method for a transposable human-like self-reliant entity predecessor human and successor human-like self-reliant entity;

transporting materials for constructing at least one predecessor biological, biomechatronic, and mechatronic human-like self-reliant entity utilizing a three-dimension nano printer file for rapid prototyping at a distant location prior to replication by said distant end printer;

constructing at least one predecessor biological, biomechatronic, and mechatronic human-like self-reliant entity by utilizing at least some portion of said three-dimensional nano printer file as a rapid prototyping data transmission format file;

saving said constructed said file of said predecessor biological, biomechatronic, and mechatronic human-like self-reliant entity file as a rapid prototyping data transmission format file compatible with a said three-dimension nano printer;

transmitting said biomechatronic, and mechatronic human-like self-reliant entity file in an analog or digital signal format over at least one terrestrial and extraterrestrial telecommunication system and network at a distant location with a said three-dimension nano printer;

communicating said file of at least one predecessor biological, biomechatronic, and mechatronic human-like self-reliant entity to a like said three-dimension nano printer at the distant location;

printing said at least one biological, biomechatronic and mechatronic human-like self-reliant entity from said three-dimension nano printer file at the distant location;

activating said at least one biological, biomechatronic, and mechatronic human-like self-reliant entity to perform as a human-like self-reliant entity; and repeating said steps herein as required in at least some portion to transform and modify said biological, biomechatronic, and mechatronic human-like self-reliant constructed at the remote end or remotely for interaction to achieve a desired result.

14. The method according to claim 9 including:

initiating the hybrid life-cycle financial management system for sustaining a predecessor and successor of a human-like self-reliant entity by operating a life-cycle financial management system financed partially or wholly by an offset to compensate at least one subscriber, subscriber's agent, enterprise, public and private entity; said offset at least one directly or indirectly providing benefit to at least one said subscriber, subscriber's agent, enterprise, public and private entity in exchange to the issuant of the offset to at least one reduce the environmental impact of usage of a natural resource, emission of carbon dioxide into the atmosphere, a scarce commodity, and address system and design engineering issues, and personal, cultural, societal, political, economic, geospatial injustice and inequality resulting from at least one human and human-like entity activity of at least one subscribing successor and predecessor of a biological, biomechatronic, and mechatronic entity; said offset being justified by the impact caused by weighing the risk and benefit of the successor and predecessor biological, biomechatronic, and mechatronic entity compared to the impact caused by the transformation of at least one successor biological, biomechatronic and mechatronic entity, sustaining the hybrid life-cycle financial management system predecessor and successor of a human-like self-reliant entity comprising human-like self-reliant entity wherein said life-cycle financial management system is financed partially or wholly by an offset to compensate at least one subscriber, subscriber's agent, enterprise, public and private entity; said offset at least one directly or indirectly providing benefit to at least one said subscriber, subscriber's agent, enterprise, public and private entity in exchange to the issuant of the offset to at least one reduce the environmental impact of usage of a natural resource, emission of carbon dioxide into the atmosphere, a scarce commodity, address system and design engineering issues, and personal, cultural, societal, political, economic, geospatial injustice and inequality resulting from at least one human and human-like entity activity of at least one subscribing successor and predecessor of a biological, biomechatronic, and mechatronic entity; said offset being justified by the impact caused by weighing the risk and benefit of the successor and predecessor biological, biomechatronic, and mechatronic entity compared to the impact caused by the transformation of at least one successor biological, biomechatronic and mechatronic entity.

15. The self-reliant human-like entity according to the method in claim 9 comprising:
 initiating said enterprise hybrid life-cycle financial management system to enable transposable transformation of a predecessor and successor of a human-like self-reliant entity:
  operating a conveyable computer with a cognitive memory system and computer subsystems operated in real time to dynamically correlate neural network activity data with surrounding environment data akin to a human including:
  a first computer subsystem including and compatible one to the ninth said conveyable computer system that derives, includes, and is compatible with a neural correlates of consciousness database stored as non-volatile cognitive memory in said computer subsystem that defines a taxonomy for said entity's perception of self and the environment;
  said first computer subsystem including and compatible with said neural correlates of consciousness database operated upon by at least one a biological neural network and artificial neural network that includes backpropagation processes that iteratively and adaptively derive logic-based outcomes that improve results or achieve desired outcomes that are decided by said entity and determine said entity's activity;
  said first computer subsystem including and compatible with said entity's sensor management that operates to record and store in non-volatile memory entity self-sensing systems and surrounding environment signatures, operates on non-volatile memory signatures to formulate a plan based on the entity's internal operations and the external surrounding environment, and acts with the intent to reach a goal based on the plan derived and shaped by the entity's overall design;
  said first computer subsystem operating on at least one neural network to derive neural correlates of consciousness from conscious percepts and subsequently to operate on those neural correlates of consciousness to make decisions as a self-reliant recipient system;
  a second computer subsystem including a support structure with an actuator and manipulator subsystem that operates with the mobility and dexterity akin to a human;
  a third computer subsystem including a rechargeable energy generation subsystem that operates akin to a human;
  said conveyable computer system and subsystems, energy generation, structural support with actuator and manipulator subsystems being in communicating relationship and once initiated operating as a cohesive system akin to a human;
 activating a life-cycle hybrid annuity financial management system for improving a predecessor and successor human-like self-reliant entity;
 operating a cognitive computer with machine learning capabilities to perform requirements-based automated correlation of at least one subscriber based artifacts and personal digital assistance information that designs an entity an entity by operating said cognitive computer with machine language capabilities that performs requirements-based capability design based on derived data using the Joint Capabilities Integration and Development System (JCIDS) guidance; said computer operating on said JCIDS methodology to determine the optimal capabilities to construct said human-like entity given key performance parameters and key system attributes that include intellectual, emotional, and physical requirements; determining said entity requirements of the entity by conducting statistically analysis of the sensing, measuring, and weighting of the neural activity of required by a human-like biomechatronic and mechatronic human-like entity that stimulates action potentials in at least one brain of a biomechatronic entity and of at least one artificial neural network of a biomechatronic entity and mechatronic system; said sensing, measuring, and weighting action potentials measured using a brain activity sensing system in a biomechatronic system and said sensing, measuring, and weighting action potentials at least one mimicked and enhanced in a biomechatronic and mechatronic entity attributes in in the artificial neural networks with backpropagation with firmware and hardware to facilitate learning and communication; said biological and electronic neural networks communicating together by brain to machine and machine to brain interface; said interface including image and pattern recognition systems that take sensed and telecommunicated data input for analysis by the entity from the surrounding environment about the entity; said input sources including input internal to the entity, from the immediate entity surrounding environments, and from entity remote databases to facilitate deep learning and communication sources including social media and search engines; said entity including a mobile telecommunication systems that receive local and remote wirelessly communicated surrounding environment information; said associated enterprise design, medical and engineering systems including the capability to test and validate the quality of said associated predecessor and successor biological, biomechatronic, mechatronic human-like self-reliant entity as an avatar in a virtual simulation or as a help-robot; said entity including the capability to remain an entity with at least one without hardware or firmware that at least one makes the entity not sentient or activates sentient; and
 incorporating key system attributes that include: a physical framework that includes Boston Dynamics® bipedal robot stabilization, guidance system, center of gravity, dexterity, and mobility; an intellectual framework of the collision avoidance and navigation and processing of at least one a Tesla® Dojo® Chip and Intel® 12$^{th}$ gen CPUs for incorporation in order to facilitate a general purpose entity; and an intellectual framework that includes an animatronic system like that of Erica, a Japanese chat robot, with natural looking human facial and other body features; and the emotional framework including computer systems and methods that uses data analytics to characterize joint statistical properties that distinguishes between the normal state of the system and variance of a predecessor and successor entity in order to facilitate the measuring and modifying the neural structure for self-governance of individual and cohorts in order to facilitate an optimal design solution for at least one a biomechatronic and mechatronic system occupying a required environment; wherein said hybrid annuity is initiated to optimize the ontogeny in the design of at least one human-like biomechatronic and mechatronic entity.

16. An enterprise system comprising:
 a business architecture that initiates and administers a life-cycle hybrid annuity instrument to transition, transform, and maintain at least one biological being, biomechatronic entity, and mechatronic entity at the behest of a subscriber of the enterprise;
 a business architecture to assist at least one a biological living being, biomechatronic entity, and mechatronic entity of the enterprise in collecting, logging, and processing at least one artifact for use in emulating at least one being, biomechatronic entity, and mechatronic entity at the behest of a subscriber of the enterprise;

a business architecture that assists a subscriber of the enterprise in transforming said biological being, biomechatronic entity, and mechatronic entity least one of said artifacts and personal digital assist are at least one modified and transformed into at least one a different or modified personal digital assistant device, biological system, simulated entity, biomechatronic system, and mechatronic system;

a business architecture including a hybrid life-cycle financial management system that administers a hybrid annuity instrument that sustains at least one different or modified predecessor or successor, being, digital assistant device, simulated entity, biomechatronic entity, and mechatronic entity at the behest of a subscriber or agent of the subscriber of the enterprise.

17. The enterprise system according to claim 16 wherein the hybrid life-cycle financial management system for sustaining at least one a predecessor and successor being, and entity comprises:

a life-cycle hybrid annuity instrument for transforming at least one biological being, biomechatronic, and mechatronic entity that consists of a hybrid insurance contract between at least one subscriber, subscribers annuitant, and enterprise system; wherein the enterprise is capable of functioning as the subscriber's annuitant and actualizing said hybrid annuity claim; said subscriber purchasing said hybrid annuity to pay said enterprise a single lump sum or a series of payments to at least one subscriber and enterprise system to interchangeably transform said subscriber electing to at least one maintain, modify, and change at least one predecessor and successor to at least one biological, biomechatronic, and mechatronic self-reliant entity state when said annuitant's claim is approved and actualized to at least one maintain, modify, and change said entity to a different biological, biomechatronic, and mechatronic self-reliant entity state; said annuitant and issuant being able transact said subscription and annuity claim over the internet or in person; and a enterprise system including a business architecture that includes the capability to operate upon said hybrid annuity to perpetuate a life-cycle financial management system to interchangeably transform said entity when at least one predecessor and successor of at least one biological, biomechatronic and mechatronic entity elects to activate said subscriber hybrid annuity claim and said annuitant approves and actualizes said claim; said annuitant and enterprise having an internet telecommunication system to transact assist in software and firmware updates of said hybrid annuity; said subscriber and annuitant including the capability to transport the subscriber to and from an enterprise medical treatment facility and engineering service facility when required for honoring said hybrid annuity claim; at least one said predecessor and successor procedure enabled by a business architecture with at least one medical treatment facility and engineering service facility required to actualize said hybrid annuity claim; implementing treatment and service to said subscriber for at least one care, diagnosis, design, testing, simulation, stimulation, replacement, repair, construction, production, installation, manufacturing, and evaluation using the medical and engineering facilities, systems, and procedures; and said facilities, systems, and procedures to at least one upload and download using at least one non-invasive and invasive medical procedure into at least one predecessor and successor of at least one biological, biomechatronic and mechatronic entity.

18. The enterprise system according to claim 16 wherein:

a "life-cycle" transform comprises a transposable transformation performed by said enterprise to perform at least one biological being, bio-mechatronic entity, and mechatronic entity transformation; said subscriber being or entity activating said life-cycle hybrid annuity within the context of said enterprise system; wherein said enterprise system operates the business architecture focuses equipment to process subscriber artifacts, personal digital assistant data, predecessor and successor raw, metadata, and processed data and information, act on subscriber desires, act within design and engineering parameters, capabilities, and constraints, and act within at least one legal and regulatory guidelines to complete at least one said being and entity transposable transformation.

19. An enterprise method comprising:

initiating business architecture that initiates and administers a life-cycle hybrid annuity instrument to transition, transform, and maintain at least one biological being, biomechatronic entity, and mechatronic entity at the behest of a subscriber of the enterprise;

operating business architecture to assists at least one a biological living being, biomechatronic entity, and mechatronic entity of the enterprise in collecting, logging, and processing at least one artifact for use in emulating at least one being, biomechatronic entity, and mechatronic entity at the behest of a subscriber of the enterprise;

operating a business architecture that assists a subscriber of the enterprise in transforming said biological being, biomechatronic entity, and mechatronic entity least one of said artifacts into at least one a different or modified personal digital assistant device, biological system, biomechatronic system, and mechatronic system;

operating a business architecture including a hybrid life-cycle financial management system that administers a life-cycle hybrid annuity instrument that transforms, sustains, and maintains at least one predecessor or successor digital assistant device, being, biomechatronic entity, and mechatronic entity at the behest of a subscriber of the enterprise.

20. The enterprise method according to claim 19 wherein the hybrid life-cycle financial management system to sustain a predecessor and successor of at least one being and entity comprises:

operating a hybrid annuity life-cycle instrument for a biological, biomechatronic, and mechatronic entity that comprises an hybrid insurance contract between at least one subscriber, subscribers annuitant, and enterprise system; wherein the enterprise is capable of functioning as the subscriber's annuitant and actualizing said hybrid annuity claim; said subscriber purchasing said hybrid annuity to pay said enterprise a single lump sum or a series of payments to at least one subscriber and enterprise system to interchangeably transform said subscriber electing to at least one maintain, modify, and change at least one predecessor and successor to at least one biological, biomechatronic, and mechatronic self-reliant entity state when said annuitant's claim is approved and actualized to at least one maintain, transform, and sustain at least one said being and entity to a different biological, biomechatronic, and mechatronic self-reliant entity state; said annuitant and issuant being able transact said subscription and annuity claim over the internet or in person; and operating a enterprise system including a business architecture that includes the capability to operate upon said hybrid annuity to perpetuate a life-cycle financial management system to interchangeably transform said entity when at least one predecessor and successor of at least one biological, biomechatronic and mechatronic entity elects to activate said subscriber hybrid annuity claim and said annuitant approves and actualizes said claim; said annuitant and enterprise having an internet telecommunication system to transact assist in software and firmware updates of said hybrid annuity; said subscriber and annuitant including the capability to transport the subscriber to and from an enterprise medical treatment facility and engineering service facility when required for honoring said hybrid annuity claim; at least one said predecessor and successor procedure enabled by a business architecture with at least one medical treatment facility and engineering service facility required to actualize said hybrid annuity claim; implementing treatment and service to said subscriber for at least one care, diagnosis, design, testing, simulation, stimulation, replacement, repair, construction, production, installation, manufacturing, and evaluation using the medical and engineering facilities, systems, and procedures; and said facilities, systems, and procedures to at least one upload and download using at least one non-invasive and invasive medical procedure into at least one predecessor and successor of at least one biological, biomechatronic and mechatronic entity.

\* \* \* \* \*